US006803186B2

(12) United States Patent
Davenport et al.

(10) Patent No.: US 6,803,186 B2
(45) Date of Patent: Oct. 12, 2004

(54) COMPOSITIONS AND METHODS FOR INCREASING AMINO ACID ABSORPTION IN MAMMALS

(75) Inventors: Gary Mitchell Davenport, Dayton, OH (US); Jamie Clyde Matthews, Danville, KY (US)

(73) Assignee: The IAMS Company, Dayton, OH (US)

( * ) Notice: Subject to any disclaimer, the term of this patent is extended or adjusted under 35 U.S.C. 154(b) by 207 days.

(21) Appl. No.: 10/087,402

(22) Filed: Mar. 1, 2002

(65) Prior Publication Data

US 2003/0170748 A1 Sep. 11, 2003

Related U.S. Application Data

(60) Provisional application No. 60/273,263, filed on Mar. 2, 2001, and provisional application No. 60/344,088, filed on Dec. 26, 2001.

(51) Int. Cl.[7] .......................... C12Q 1/00; C12Q 1/02; A61K 38/00; C07K 1/00

(52) U.S. Cl. .......................... 435/4; 435/29; 530/300; 530/350

(58) Field of Search ...................... 435/4, 29; 530/300, 530/350

(56) References Cited

U.S. PATENT DOCUMENTS

| | | | | |
|---|---|---|---|---|
| 4,873,192 A | | 10/1989 | Kunkel | 435/172.3 |
| 5,231,020 A | | 7/1993 | Jorgensen et al. | 435/172.3 |
| 6,204,291 B1 | * | 3/2001 | Sunvold et al. | 514/556 |
| 6,383,529 B2 | * | 5/2002 | Davenport et al. | 424/773 |
| 6,683,169 B2 | * | 1/2004 | Knipp et al. | 536/23.5 |

FOREIGN PATENT DOCUMENTS

WO WO 02/070658 A2 * 9/2002

OTHER PUBLICATIONS

Adibi, S.A., and E. L. Morse. 1971 Intestinal transport of dipeptides in man: relative importance of hydrolysis and intact absorption. J. Clin. Invest. 50:2266–2275.

Adibi, S.A. 1977. The oligopeptide transporter (Pept–1) in human intestine: biology and function. Gastroenterology 113:332–340.

Brandsch, M., V. Ganapathy, and F. H. Leibach. 1995 H(+)–peptide contransport in Madin–Darby canine kidney cells: expression and calmodulin–dependent regulation. Am. J. Physiol 268:F391–F397.

Fei, Y.J., Y. Kanai, S. Nussberger, V. Ganapathy, F.H. Leibach, M. F. Romero, S. K. Singh, W. F. Boron, and M. A. Hediger. 1994. Expression cloning of a mammalian proton-coupled oligopeptide transporter. Nature 368:563–566.

Ferraris, R.P., J. Diamond, and W. W. Kwan. 1988. Dietary regulation of intestinal transport of the dipeptide carnosine. Am. J. Physiol. 255:G143–G150.

Ganapathy, V., M. Brandsch, and F. H. Leibach. 1994. Intestinal transport of amino acids and peptides. In: Physiology of the Gastrointestinal Tract, Third ed., (Johnson, L.R., ed.), pp. 1773–1794. Raven Press, New York.

(List continued on next page.)

*Primary Examiner*—Louise N. Leary
(74) *Attorney, Agent, or Firm*—Kelly L. McDow-Dunham; Karen F. Clark

(57) ABSTRACT

The present invention provides novel isolated and purified nucleic acid (RNA or DNA) encoding, or complementary to, a canine PepT1 (cPepT1). The present invention also provide a method for determining canine PepT1-transportability of a peptide, or method for determining a peptide with beneficial nutritional property in an animal. The present invention further provides a dietary composition for an animal comprising a peptide identified by the method described above.

26 Claims, 15 Drawing Sheets

OTHER PUBLICATIONS

Kilberg, M.S. 1989. Measurement of amino acid transport by hepatocytes in suspension and monolayer culture. Methods Enzym. 173: 564–575.

Madin, S.H. and N.B. Darby. 1958. Established kidney cell line of normal adult bovine and ovine origin. Proc. Soc. Exp. Biol. 98:574–576.

Matthews, J.C. 2000. Amino acid and peptide transport systems. In: Farm Animal Metabolism and Nutrition, (J.P.F.D'mello, ed.), pp. 1773–1794. CABI, New York.

Matthews, J.C., E.A. Wong, P. K. Bender, J. R. Bloomquist, and K. E. Webb, Jr. 1996. Demonstration and characterization of dipeptide transport system activity in sheep omasal epithelium by expression of mRNA in Xenopus laavis oocytes. J. Anim. Sci. 74:1720–1727.

Newey, H., and D. H. Smith. 1959. The intestinal absorption of some dipeptides. J. Physiol. 145:48–56.

Ogihara, H., T. Suzuki, Y. Nagamachi, K. Inui, and K. Takata. 1999. Peptide transporter in the rat small intestine: ultrastructural localization and the effect of starvation and administration of amino acids. Histochem. J. 31:169–174.

Shiraga, T., K. Miyamoto, H. Tanaka, H. Yamanoto, Y. Taketani, K. Morita, I. Tamai, A. Tsuji, and E. Takeda. 1999. Cellular and molecular mechanisms of dietary regulation on rat intestinal H+/ Peptide transporter PepT1. Gastroenterology 116:354–362.

Terada, T., K. Sawada, M. Irie, H. Saito, Y. Hashimoto, and K. Inui. 2000. Structural requirements for determining the substrate affinity of peptide transporters PEPT1 and PEPT2. Pflugers. Arch 440:679–684.

Walker, D., D. T. Thwaites, N. L. Simmons, H. J. Gilbert, and B. H. Hirst. 1998. Substrate upregulation of the human small intestinal peptide transporter, hPepT1. J. Physiol. 507:697–706.

* cited by examiner

Figure 5.

TGGCTGGGGAAGTTCAAGACAATCGTGTCACTCTCCATTGTCTACACAATTGGACAG
GCGGTCACTGCAGTAAGCTCAATTAATGACCTCACAGACTATAACAAAGATGGAAC
TCCTGACAATCTGTCCGTGTATGTGGCACTGTCCATGATTGGCCTGGCCCTGATAGCT
CTGGGAACTGGAGGAATAAAGCCCTGTGTGTCTGCATTTGGTGGAGAGCAGTTTGAA
GAGGGCCAGGAAAAACAAAGAAACAGATTCTTTTCCATCTTTTATTTGGCCATTAAT
GCTGGAAGCTTGATTTCCACTATTGTCACTCCCATGCTCAGAGTTCACGAATGTGGA
ATTTACAGTCAGAAAGCTTGCTACCCACTGGCCTTTGGG

COMPOSITIONS AND METHODS FOR INCREASING AMINO ACID ABSORPTION IN MAMMALS

CROSS-REFERENCE TO RELATED APPLICATIONS

This application claims the benefit of U.S. Provisional Application Ser. No. 60/273,263, filed Mar. 2, 2001, under 35 U.S.C. 119(e) and U.S. Provisional Application Ser. No. 60/344,088, filed Dec. 26, 2001, under 35 U.S.C. 119(e).

BACKGROUND OF THE INVENTION

In dogs, it is thought that the ability to absorb essential amino acids such as tryptophan and leucine may be limiting to cellular metabolism. Recent research designed to characterize the amino acid absorption capacity of the brush border (lumen facing) membranes of dog enterocytes suggests that peptide absorption may be particularly important given the relatively low amount of free amino acid transport capacity that was observed. Buddington R K, Paulsen D B. Development of the Canine and Feline Gastrointestinal Tract. In: Reinhart G A, Carey D P, eds. *Recent Advances in Canine and Feline Nutrition, Vol. II:* 1998 *Iams Nutrition Symposium Proceedings*. Wilmington: Orange Frazer Press, 1998; 195–215. Data collected from studies designed to understand the quantitative importance of free versus peptide amino acids in other monogastric animals strongly indicates that peptide-bound amino acids account for the majority of amino acids absorbed by enterocytes from the intestinal lumen (Matthews, D M. *Protein Absorption, Development and Present State of the Subject*, New York: Wiley-Liss, 1991.) and that the rate of peptide-derived amino acid absorption is faster than that by equivalent amounts of free amino acids. Ohkohchi N, Andoh T, Ohi R, Mori S. Defined formula diets alter characteristics of the intestinal transport of amino acid and peptide in growing rats. *J Pediatr Gastroenterol Nutr* 1990 May; 10(4):490–6.

Two types of peptide transporters have been cloned from monogastric animals. Liang R, Fei Y J, Prasad P D, Ramamoorthy S, Han H, Yang-Feng T L, Hediger M A, Ganapathy V, Leibach F H. Human intestinal H+/peptide cotransporter. Cloning, functional expression, and chromosomal localization. *J Biol Chem* 1995 Mar. 24; 270(12):6456–63. Liu W, Liang R, Ramamoorthy S, Fei Y J, Ganapathy M E, Hediger M A, Ganapathy V, Leibach F H. Molecular cloning of PEPT 2, a new member of the H+/peptide cotransporter family, from human kidney. *Biochim Biophys Acta* 1995 May 4; 1235(2):461–6. PepT1 is an $H^+$-dependent, low-affinity (mM), high-velocity, transporter that is predominately localized primarily to the brush border membranes of mature enterocytes of intestinal villi. PepT2 is an $H^+$-dependent, high-affinity ($\mu$M), low-velocity, transporter that is expressed in the greatest abundance in the apical membranes of renal proximal tubular epithelial cells. An important feature of the peptide transporters is their ability to recognize and transport most di- and tripeptides, albeit with a range of relative affinities for different peptides. In addition, both transporters recognize the β-lactam antibiotics, and carboxyl-terminal modified free amino acids. The physiologic functions of these transporters are thought to be to absorb di- and tripeptides from the digesta and from the blood, respectively. Although molecular evidence has not been acquired, there is strong biochemical evidence for a different peptide transport protein that functions in the basolateral membrane of these cells. Saito H, Inui K I. Dipeptide transporters in apical and basolateral membranes of the human intestinal cell line Caco-2. *Am J Physiol* 1993 August; 265(2 Pt 1):G289–94. Thwaites D T, Brown C D, Hirst B H, Simmons N L. Transepithelial glycylsarcosine transport in intestinal Caco-2 cells mediated by the expression of $H^+$-coupled carriers at both the apical and basal membranes. *J Biol Chem* 1993 April 15; 268(11):7640–2.

Research with Caco-2 cells indicates that PepT1 transporter mRNA, protein, and activity increases in a manner consistent with a direct effect of increased extracellular substrate concentrations. Walker D, Thwaites D T, Simmons N L, Gilbert H J, Hirst B H. Substrate upregulation of the human small intestinal peptide transporter, hPepT1. *J Physiol* 1998 Mar. 15; 507(Pt 3):697–706. In contrast to mRNAs for essential amino acid transporters, intestinal studies show that the expression of peptide transporter mRNA increases in response to increased dietary protein. Erickson R H, Gum J R Jr, Lindstrom M M, McKean D, Kim Y S. Regional expression and dietary regulation of rat small intestinal peptide and amino acid transporter mRNAs. *Biochem Biophys Res Commun* 1995 Nov. 2; 216(1):249–57. Similarly, expression in intestinal mucosa of PepT1 mRNA and protein increases in response to tissue trauma, whereas the MRNA for essential amino acid transporters decreases. Tanaka H, Miyamoto K I, Morita K, Haga H, Segawa H, Shiraga T, Fujioka A, Kuoda T, Taketani Y, Hisano S, Fukui Y, Kitagawa K, Takeda E. Regulation of the PepT1 peptide transporter in the rat small intestine in response to 5-fluorouracil-induced injury. *Gastroenterology* 1998 April; 114(4):714–23.

Few studies have been conducted to evaluate the potential for the dog to absorb quantitatively significant amounts of essential amino acids in the form of small peptides, and whether this capacity can be regulated by substrate supply. Accordingly, there is still a need to evaluate the potential for the absorption of peptide-bound leucine and tryptophan by putative canine peptide transporters. It would thus be desirable to provide the nucleic acid sequence encoding canine PepT1. It would also be desirable to provide mRNA transcripts corresponding to cPepT1. It would further be desirable to characterize the function of cPepT1 by GlySar uptake and identify di- and tripeptides well recognized by cPepT1, as well as characterize the effect of supplemental peptide substrate on the transport capacity of canine PepT1 (cPepT1).

SUMMARY OF THE INVENTION

The present invention provides novel isolated and purified nucleic acids (RNA or DNA) encoding, or complementary to, canine PepT1 (cPepT1). The nucleic acid may be SEQ ID NO:7, SEQ ID NO:8, SEQ ID NO:9, or SEQ ID NO:20 or may be a nucleic acid that hybridizes under moderate or stringent hybridization conditions to any of these sequences. Also provided are peptides encoded by these nucleic acids, such as SEQ ID NO: 13 or SEQ ID NO:21.

The present invention also provides a method for determining canine PepT1-transportability of a peptide, or method for determining a peptide with beneficial nutritional property in an animal, comprising providing an immortalized kidney distal tubule epithelial (Madin-Darby Canine Kidney (MDCK)) cell and a peptide having 2 to 10 amino acids, and determining the amount of the peptide transported into the cell, wherein the amount correlates with the canine PepT1-transportability of the peptide. A peptide with beneficial nutritional properties in an animal is a peptide that contains at least one essential amino acid that is absorbed at a rate higher than the rate of the amino acid if it were free rather than in a peptide-bound form. The peptide may be a dipeptide, tripeptide, or tetrapeptide such as, for example, GlySar, GlyGly, AlaHis, β-AlaHis (carnosine), GlnGln, GlyMet, LeuMet, LeuTrp, MetLeu, MetMet, MetPhe, MetPro, TrpLeu, TrpTrp, GlnGlu, MetGlu, MetLys, TrpGly, MetGlyMetMet (SEQ ID NO:10), TrpGlyGly, LeuArg, ArgLeu, GlyLeu, or ArgTrp. The cell used in the method may be in medium at a pH of between about 5 and 8; or at a pH of about 5.5 to 7.5, or even at about 6 to 6.5. The peptide may be present at a concentration of about 10 nm to about 50 mM.

The characterization of GlySar uptake by immortalized MDCK cells demonstrates that MDCK cells express PepT1-like activity, confirming detection of PepT1 MRNA expression by MDCK cells and the use of MDCK cells as a model to characterize the biochemical function of canine PepT1.

The cPepT1 of the present invention is also capable of recognizing a variety of di- and tripeptides, including those that contain the essential amino acids leucine and tryptophan, considered to be of especial importance to canine nutrition. In addition, $H^+$-dependent peptide transport in cultured MDCK cells can be stimulated by at least two of PepT1 substrates, GlySar and carnosine. Moreover, $H^+$-dependent uptake of GlySar by MDCK is sensitive to nutrient deprivation and Insulin-like Growth factor I (IGF-I).

The present invention further provides a dietary composition with improved nutritional benefit for an animal comprising at least one peptide identified by the method described above.

The present invention provides a process for altering the absorption of essential amino acids in an animal, such as a dog, comprising the steps of feeding the animal a diet containing the dietary composition described above; and maintaining the animal on the diet for a sufficient period of time to allow the composition to be absorbed by the digestive system of the animal. The diet may comprise about 20 to about 30% crude protein, about 10 to about 20% fat, and about 3 to about 10% dietary fiber.

As used herein, the term "cPepT1" includes variants or biologically active or inactive fragments of this transport protein. A "variant" of the polypeptide is a cPepT1 protein that is not completely identical to a native cPepT1 protein. A variant cPepT1 protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 common amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains. Stryer, L. *Biochemistry* (2d edition) W. H. Freeman and Co. San Francisco (1981), p. 14–15; Lehninger, A. *Biochemistry* (2d ed., 1975), p. 73–75. It is known to those of skill in the art that transport of other, less common, amino acids such as hydroxylysine, or derivatives of any one of the 20 common amino acids listed above would also be within the scope of this invention.

It is known that variant polypeptides can be obtained based on substituting certain amino acids for other amino acids in the polypeptide structure in order to modify or improve biological activity. For example, through substitution of alternative amino acids, small conformational changes may be conferred upon a polypeptide that result in increased bioactivity. Alternatively, amino acid substitutions in certain polypeptides may be used to provide residues that may then be linked to other molecules to provide peptide-molecule conjugates that retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity. It is noted that substitutions can be made based on the hydrophilicity assigned to each amino acid. In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant cPepT1 protein comprises at least seven amino acid residues, preferably about 20 to about 700 residues, and more preferably about 50 to about 700 residues, wherein the variant cPepT1 protein has at least 50%, preferably at least about 80%, and more preferably at least about 90% but less than 100%, contiguous amino acid sequence homology or identity to the amino acid sequence of a corresponding native cPepT1 protein.

The amino acid sequence of the variant cPepT1 protein corresponds essentially to the native cPepT1 protein amino acid sequence. As used herein "correspond essentially to" refers to a polypeptide sequence that will elicit an absorption value substantially the same as the absorption stimulated by native cPepT1 protein. Such absorption may be at least 60% of the level generated by native cPepT1 protein, and may even be at least 80% of the level generated by native cPepT1 protein.

A variant of the invention may include amino acid residues not present in the corresponding native cPepT1 protein, or may include deletions relative to the corresponding native cPepT1 protein. A variant may also be a truncated "fragment" as compared to the corresponding native cPepT1 protein, i.e., only a portion of a full-length protein. cPepT1 protein variants also include peptides having at least one D-amino acid.

The cPepT1 protein of the present invention may be expressed from an isolated nucleic acid (DNA or RNA) sequence encoding the cPepT1 protein. Amino acid changes from the native to the variant cPepT1 protein may be achieved by changing the codons of the corresponding nucleic acid sequence. "Recombinant" is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence. The terms "protein," "peptide" and "polypeptide" are used interchangeably herein.

BRIEF DESCRIPTION OF THE FIGURES

FIG. 2A is a photograph of an agarose gel showing representative results of the PCR-based analyses of TA-clone 26. In particular, analyses of pCR®II/cPepT1-26 (TA-clone 26) are shown; lane 1, 1 DNA size standard; lane 2, minus endonuclease-restriction control (uncut pCR®II plasmid); lane 3, positive restriction control (Xho I restriction of empty pCR®II vector); lane 4, uncut pCR®II/cPepT1-26 (Clone 26); lane 5, Xho I- and Kpn I-restricted Clone 26. Note that empty pCR®II vector is 3.9 kb in size and that lane 5 contains a product of about 780 bp. FIG. 2B is a photograph of an agarose gel showing representative results of the PCR-based analyses of TA-clone 4 and 6. In particular, analyses of TA-clone 4 and 6 are shown; lane 1, DNA size standard; lane 2, uncut pCR®II/cPepT1-4 (TA-clone 4); lane 3, Xho I- and Kpn I-restricted pCR®II/cPepT1-4; lane 4, uncut pCR®II/cPepT1-6 (TA-clone 6); lane 5, Xho I- and Kpn I-restricted pCR®II/cPepT1-6. Note that empty pCR®II vector is 3.9 kb in size and that lane 3 does not contain a product of about 780 bp, whereas lane 5 does.

FIG. 3A is a photograph showing the Northern blot identification of $A^+$RNA (3 $\mu$g/lane) that was hybridized with [$^{32}$P]-cPepT1-26 cDNA. FIG. 3B is a photograph showing the Northern blot identification of total RNA (20 $\mu$g/lane) that was hybridized with [$^{32}$P]-cPepT1-6 cDNA.

FIG. 5 is the partial-length nucleic acid sequence of canine PepT1 cDNA of the present invention that was cloned from MDCK cells (SEQ ID NO:9). The 381 base pairs of TA clone PepT1-6R-20 shares 79% homology to base pairs 259 to 640 of rabbit PepT1 (GenBank acc no. 473375).

DEFINITIONS

Figure 1:
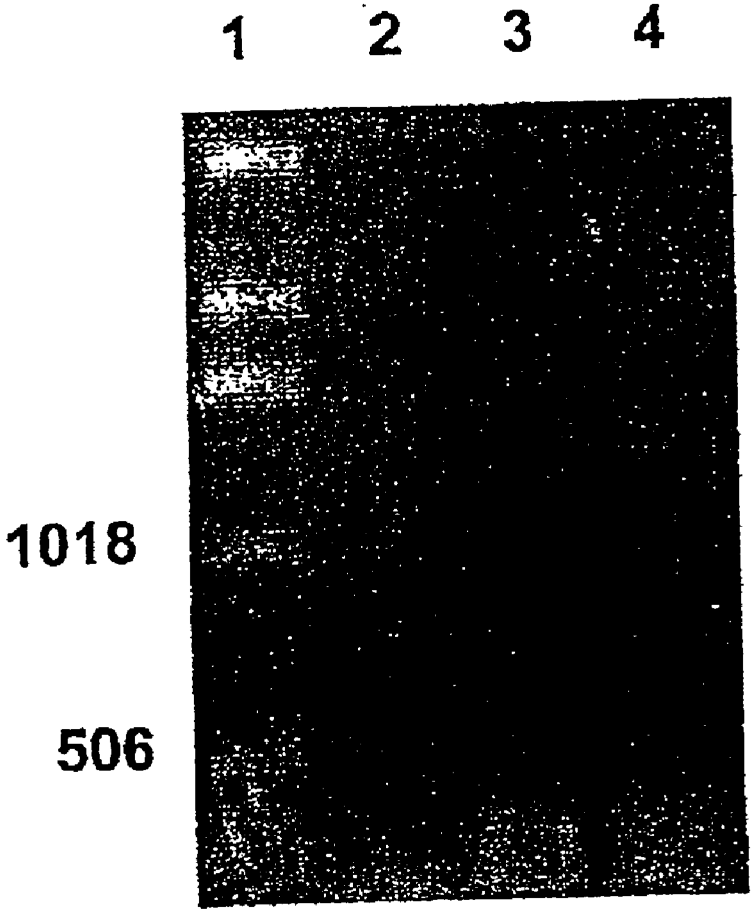
FIG. 1 is a photograph of an electrophoresis gel showing the partial length canine PepT1 cDNA reaction products generated by reverse transcription-polymerase chain reaction (RT-PCR) methodology. Partial length canine PepT1 (cPepT1, about 783 bp) cDNAs were generated by reverse transcription-polymerase chain reaction (RT-PCR) methodology. RT-PCR reaction products were generated using mRNA isolated from canine jejunal epithelium and two different PCR primer sets. Gel contents are as follows: lane 1, 1 Kb molecular weight DNA ladder; lane 2, negative control PCR reaction (lacks Taq polymerase); lane 3, PCR reaction products using primer set 4 (corresponding to base pairs 83 to 863 of rabbit PepT1); lane 4, PCR reaction products using primer set 10~780 bp cDNA product using primer set 10 (corresponding to base pairs 85 to 861 of rabbit PepT1). Note the reaction products in lanes 3 and 4 of about 780 base pairs.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The term "native gene" refers to gene that is present in the genome of an untransformed cell.

"Naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

A "marker gene" encodes a selectable or screenable trait.

The term "chimeric gene" refers to any gene that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, genes that are either heterologous or homologous to the genes of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

The terms "protein," "peptide" and "polypeptide" are used interchangeably herein.

Expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The transcriptional cassette will include in the 5'-3' direction of transcription, a transcriptional and translational initiation region, a DNA sequence of interest, and a transcriptional and translational termination region. The termination region may be native with the transcriptional initiation region, may be native with the DNA sequence of interest, or may be derived from another source.

An oligonucleotide for use in probing or amplification reactions may be about 30 or fewer nucleotides in length (e.g., 9, 12, 15, 18, 20, 21 or 24, or any number between 9 and 30). Generally specific primers are upwards of 14 nucleotides in length For optimum specificity and cost effectiveness, primers of 16–24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency. (Turner et al., *Molecular Biotechnology,* 3:225 (1995)).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5' ) of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

The term "intracellular localization sequence" refers to a nucleotide sequence that encodes an intracellular targeting signal. An "intracellular targeting signal" is an amino acid sequence that is translated in conjunction with a protein and directs it to a particular sub-cellular compartment. "Endoplasmic reticulum (ER) stop transit signal" refers to a carboxy-terminal extension of a polypeptide, which is translated in conjunction with the polypeptide and causes a protein that enters the secretory pathway to be retained in the ER. "ER stop transit sequence" refers to a nucleotide sequence that encodes the ER targeting signal.

"Promoter" refers to a nucleotide sequence, usually upstream (5') to its coding sequence, that controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Inducible promoter" refers to those regulated promoters that can be turned on in one or more cell types by an external stimulus, such as a chemical, light, hormone, stress, or a pathogen.

"Operably-linked" refers to the association of nucleic acid sequences on single nucleic acid fragment so that the function of one is affected by the other. For example, a regulatory DNA sequence is said to be “operably linked to” or “associated with” a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

“Expression” refers to the transcription and/or translation of an endogenous gene or a transgene in cells. For example, in the case of antisense constructs, expression may refer to the transcription of the antisense DNA only. In addition, expression refers to the transcription and stable accumulation of sense (mRNA) or functional RNA. Expression may also refer to the production of protein.

The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site (‘initiator’) plays an important role in determining the level of RNA expression directed by that specific promoter. This includes also part of the transcribed sequences. The direct fusion of promoter to reporter sequences would therefore lead to much suboptimal levels of transcription.

A commonly used procedure to analyze expression patterns and levels is through determination of the ‘steady state’ level of protein accumulation in a cell. Commonly used candidates for the reporter gene, known to those skilled in the art are 9-glucuronidase (GUS), growth hormone (GH), Chloramphenicol Acetyl Transferase (CAT) and proteins with fluorescent properties, such as Green Fluorescent Protein (GFP) from *Aequora victoria*. In principle, however, many more proteins are suitable for this purpose, provided the protein does not interfere with essential cell functions. For quantification and determination of localization a number of tools are suited. Detection systems can readily be created or are available which are based on e.g. immunochemical, enzymatic, fluorescent detection and quantification. Protein levels can be determined in cell extracts or in intact tissue using in situ analysis of protein expression.

Generally, individual transformed lines with one chimeric promoter reporter construct will vary in their levels of expression of the reporter gene. Also frequently observed is the phenomenon that such transformants do not express any detectable product (RNA or protein). The variability in expression is commonly ascribed to position effects, although the molecular mechanisms underlying this inactivity are usually not clear.

“Non-specific expression” refers to constitutive expression or low level, basal (‘leaky’) expression in nondesired cells or tissues from a ‘regulated promoter’.

“Antisense inhibition” refers to the production of antisense RNA transcripts capable of suppressing the expression of protein from an endogenous gene or a transgene.

“Co-suppression” and “transwitch” each refer to the production of sense RNA transcripts capable of suppressing the expression of identical or substantially similar transgene or endogenous genes (U.S. Pat. No. 5,231,020).

“Homologous to” refers to the similarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U.K.), or by the comparison of sequence similarity between two nucleic acids or proteins.

The term “substantially similar” refers to nucleotide and amino acid sequences that represent equivalents of the instant inventive sequences. For example, altered nucleotide sequences which simply reflect the degeneracy of the genetic code but nonetheless encode amino acid sequences that are identical to the inventive amino acid sequences are substantially similar to the inventive sequences. In addition, amino acid sequences that are substantially similar to the instant sequences are those wherein overall amino acid identity is 95% or greater to the instant sequences. Modifications to the instant invention that result in equivalent nucleotide or amino acid sequences is well within the routine skill in the art. Moreover, the skilled artisan recognizes that equivalent nucleotide sequences encompassed by this invention can also be defined by their ability to hybridize, under stringent conditions (0.1×SSC, 0.1% SDS, 65° C.), with the nucleotide sequences that are within the literal scope of the instant claims.

“Transgene activation system” refers to the expression system comprised of an inactive transgene and a chimeric site-specific recombinase gene, functioning together, to effect transgene expression in a regulated manner. The specificity of the recombination will be determined by the specificity of regulated promoters as well as the use of wild-type or mutant site-specific sequences. Both elements of the system can be chromosomally integrated and inherited independently.

“Target gene” refers to a gene on the replicon that expresses the desired target coding sequence, Functional RNA, or protein. The target gene is not essential for replicon replication. Additionally, target genes may comprise native non-viral genes inserted into a non-native organism, or chimeric genes, and will be under the control of suitable regulatory sequences. Thus, the regulatory sequences in the target gene may come from any source, including the virus.

“Transcription Stop Fragment” refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

“Translation Stop Fragment” refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

“Blocking fragment” refers to a DNA fragment that is flanked by site specific sequences that can block the transcription and/or the proper translation of a coding sequence resulting in an inactive transgene. When the blocking fragment contains polyadenylation signal sequences and other sequences encoding regulatory signals capable of terminating transcription, it can block the transcription of a coding sequence when placed in the 5' non-translated region, i.e., between the transcription start site and the ORF. When inserted in the coding sequence a blocking fragment can block proper translation by disrupting its open reading frame. DNA rearrangement by site-specific recombination can restore transcription and/or proper translatability. For example, excision of the blocking fragment by site-specific recombination leaves behind a site-specific sequence that allows transcription and/or proper translatability. A Transcription or Translational Stop Fragment will be considered a blocking fragment.

The terms "in cis" and "in trans" refer to the presence of DNA elements, such as the viral origin of replication and the replication protein(s) gene, on the same DNA molecule or on a different DNA molecule, respectively.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Cis-acting viral sequences" refers to viral sequences necessary for viral replication (such as the replication origin) and in cis orientation.

"Transactivating gene" refers to a gene encoding a transactivating protein. It can encode a viral replication protein(s) or a site-specific replicase. It can be a natural gene, for example, a viral replication gene, or a chimeric gene, for example, when regulatory sequences are operably-linked to the open reading frame of a site-specific recombinase or a viral replication protein. "Transactivating genes" may be chromosomally integrated or transiently expressed.

"Wild-type" refers to the normal gene, virus, or organism found in nature without any known mutation.

"Genome" refers to the complete genetic material of an organism. The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.,* 19, 5081 (1991); Ohtsuka et al., *J. Biol. Chem.,* 260, 2605 (1985); Rossolini et al., *Mol. Cell. Probes,* 8, 91 (1994)). A "nucleic acid fragment" is a fraction of a given nucleic acid molecule. In higher animals, deoxyribonucleic acid (DNA) is the genetic material while ribonucleic acid (RNA) is involved in the transfer of information contained within DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" is intended a portion of the nucleotide sequence or a portion of the amino acid sequence, and hence a portion of the polypeptide or protein, encoded thereby. Alternatively, fragments of a nucleotide sequence that are useful as hybridization probes generally do not encode fragment proteins retaining biological activity. Thus, fragments of a nucleotide sequence may range from at least about 9 nucleotides, about 12 nucleotides, about 20 nucleotides, about 50 nucleotides, about 100 nucleotides or more.

By "variants" is intended substantially similar sequences. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis which encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%–84%, at least 85%, e.g., 86%, 87%, 88%, 89%, 90%, 91%, 92%, 93%, 94%, 95%, 96%, 97%, to 98% sequence identity to the native nucleotide sequence.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, *Proc. Natl. Acad. Sci. USA,* 82, 488 (1985); Kunkel et al., *Methods in Enzymol.,* 154, 367 (1987); U.S. Pat. No. 4,873,192; Walker and Gaastra, eds., *Techniques in Molecular Biology*, MacMillan Publishing Company, New York (1983) and the references cited therein. Guidance as to appropriate amino acid substitutions that do not affect biological activity of the protein of interest may be found in the model of Dayhoff et al., *Atlas of Protein Sequence and Structure*, Natl. Biomed. Res. Found., Washington, C.D. (1978), herein incorporated by reference. Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass both naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

The proteins of the invention may be altered in various ways including amino acid substitutions, deletions, truncations, and insertions. Methods for such manipulations are generally known in the art. Methods for mutagenesis and nucleotide sequence alterations are well known in the art. See, for example, Kunkel, *Proc. Natl. Acad. Sci. USA,* 82:488–492 (1985); Kunkel et al., *Methods in Enzymol.* 154:367–382 (1987); U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoffet al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired disease resistance activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequence encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. Hybridization of such sequences may be carried out under stringent conditions.

"Stringent hybridization conditions" and "stringent hybridization wash conditions" in the context of nucleic acid hybridization experiments such as Southern and Northern hybridization are sequence dependent, and are different under different environmental parameters. Longer sequences hybridize specifically at higher temperatures. An extensive guide to the hybridization of nucleic acids is found in Tijssen, *Laboratory Techniques in Biochemistry and Molecular biology— Hybridization with Nucleic Acid Probes*, page 1, chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences. For example, by "stringent conditions" or "stringent hybridization conditions" is intended conditions under which a probe will hybridize to its target sequence to a detectably greater degree than to other sequences (e.g., at least 2- fold over background). By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl *Anal. Biochem.* 138:267–284 (1984); $T_m$81.5°C.+16.6 (log M) +0.41 (%GC) −0.61 (% form) −500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe.

Very stringent conditions are selected to be equal to the $T_m$ for a particular probe. An example of stringent hybridization conditions for hybridization of complementary nucleic acids which have more than 100 complementary residues on a filter in a Southern or Northern blot is 50% formamide with 1 mg of heparin at 42° C., with the hybridization being carried out overnight. An example of highly stringent conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of medium stringency for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other slats) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

$T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defied ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using these parameters, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology-Hybridization with Nucleic Acid Probes, Part 1, Chapter 2 (Elsevier, New York); and Ausubel et al., eds. (1995) Current Protocols in Molecular Biology, Chapter 2 (Greene Publishing and Wiley—Interscience, New York). See Sambrook et al. (1989) Molecular Cloning: A Laboratory Manual (2d ed., Cold Spring Harbor Laboratory Press, Plainview, N.Y.).

Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

"Vector" is defined to include, inter alia, any plasmid, cosmid, or phage in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eucaryotic (e.g. higher cell, mammalian, yeast or fungal cells).

Preferably the nucleic acid in the vector is under the control of, and operably linked to, an appropriate promoter or other regulatory elements for transcription in a host cell such as a microbial, e.g. bacterial, or animal cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Operably linked" means joined as part of the same nucleic acid molecule, suitably positioned and oriented for transcription to be initiated from the promoter. DNA operably linked to a promoter is "under transcriptional initiation regulation" of the promoter.

"Chimeric" is used to indicate that a DNA sequence, such as a vector or a gene, is comprised of more than one DNA sequences of distinct origin with are fused together by recombinant DNA techniques resulting in a DNA sequence, which does not occur naturally.

The terms "heterologous DNA sequence," "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, *CABIOS* 4:11–17 (1988); the local homology algorithm of Smith et al. *Adv. Appl. Math.* 2:482 (1981); the homology alignment algorithm of Needleman and Wunsch *J. Mol. Biol.* 48:443–453 (1970); the search-for-similarity-method of Pearson and Lipman *Proc. Natl. Acad. Sci.* 85:2444–2448 (1988); the algorithm of Karlin and Altschul, *Proc. Nath. Acad Sci. USA* 872264 (1990), modified as in Karlin and Altschul, *Proc. Nath. Acad. Sci. USA* 90:5873–5877 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. *Gene* 73:237 244 (1988); Higgins et al. *CABIOS* 5:151–153 (1989); Corpet et al. *Nucleic Acids Res.* 16:10881–90 (1988); Huang et al. *CABIOS* 8:155–65 (1992); and Pearson et al. *Meth. Mol. Biol.* 24:307–331 (1994). The ALIGN program is based on the algorithm of Myers and Miller, supra. The BLAST programs of Altschul et al., *J. Mol. Biol.* 215:403 (1990), are based on the algorithm of Karlin and Altschul supra. To obtain gapped alignments for comparison purposes, Gapped BLAST (in BLAST 2.0) can be utilized as described in Altschul et al. *Nucleic Acids Res.* 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA*. 89, 10915 (1989)). See http:/www.ncbi.n1m.nih.gov. Alignment may also be performed manually by inspection.

For purposes of the present invention, comparison of nucleotide sequences for determination of percent sequence identity disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch *J. Mol. Biol.* 48:443–453 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

DETAILED DESCRIPTION OF THE INVENTION

This invention relates to peptide amino acid absorption in the dog, and more particularly, to separate, whole or partial-length, complementary DNA encoding putative canine low-affinity, high-capacity $H^+$/peptide transport proteins (cPepT1), mRNA transcripts corresponding to cPepT1, characterization of cPepT1 by glycylsarcosine (GlySar) uptake, identification of dipeptides, tripeptides, and tetrapeptides well recognized by cPepT1, and the effect of supplemental peptide substrate on the transport capacity of cPepT1.

The invention also provides a pet food composition comprising at least one dipeptide, tripeptide, or tetrapeptide that provides enhanced uptake of amino acids by PepT1. A typical canine diet for use in the present invention may also, for example, contain about 20 to about 30% crude protein, about 10 to about 20% fat, and about 10% total dietary fiber. However, no specific ratios or percentages of these or other nutrients are required.

The inventors have discovered a method for identifying peptides (e.g. dipeptides, tripeptides, or tetrapeptides) that increase transport of amino acids by PepT1 using MDCK cells, particularly when incubated with lactalbumin hydrolysate and assayed at optimum time post-seeding, as indicated in Example 2.

In order that the invention may be more readily understood, reference is made to the following examples which are intended to illustrate the invention, but not limit the scope thereof.

EXAMPLE 1

Generation of Partial-length Canine PepT1 cDNA

Partial Cloning of Canine PepT1 (cPepT1) from Small Intestinal Epithelium

Figure 2:
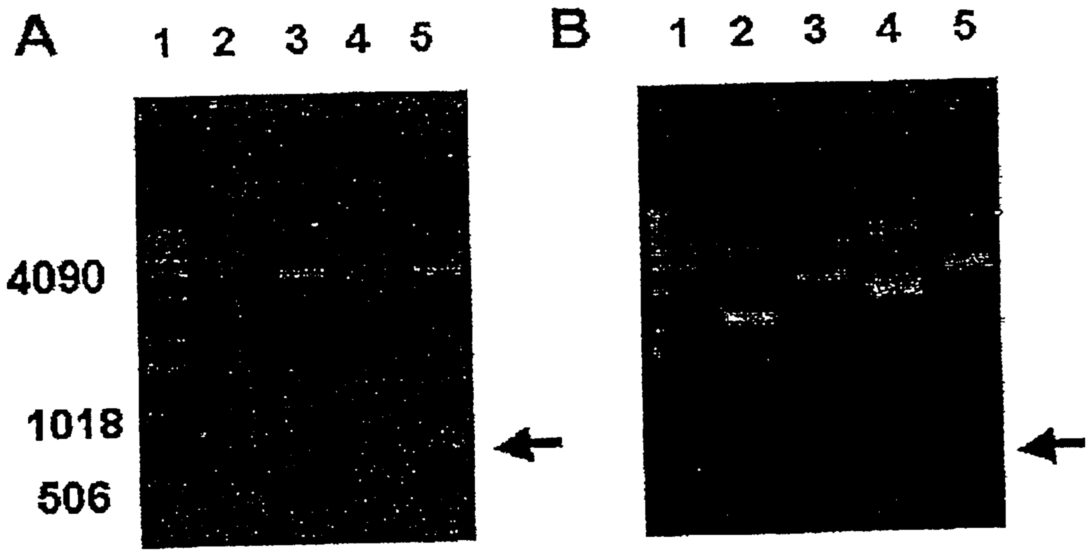
FIGS. 2A and 2B are photographs of agarose gels showing the representative results of restriction analyses of pCR®II/cPepT1 plasmids generated by TA-cloning of primer set 4derived RT-PCR cDNA. Restriction analyses of pCR®II/cPepT1 plasmids generated by TA-cloning of primer set 4-derived RT-PCR cDNA are shown in these figures. Data are representative of four cDNA-containing plasmids from a total of fifty-six "positive" bacterial colonies selected by blue/white screening. TA-clones were amplified, pCR®II/cDNA vectors isolated, and Xho I and Kpn I endonucleases restriction products size-separated through 1.2% agarose gels.

Initial attempts (over 150) to partially clone the putative canine PepT1 cDNA by reverse transcriptase-polymerase chain reaction (RT-PCR) methodology failed. The source of mRNA was canine liver tissue that had been frozen for about 6 months (supplied by Dr. Randal Buddington, Mississippi State University) and oligomer primers were based on the rabbit PepT1 sequence. Subsequently, frozen canine "mid" small intestine (jejunal) tissue segments became available (supplied by Dr. Buddington) and a partial length cDNA of about 780 base pairs (bp) was cloned by RT-PCR. Total RNA was isolated from jejunal epithelium scraped from intestinal sections using a standard acidic phenol-chloroform protocol. One μg of mRNA was isolated from total RNA using POLY A TRACT SYSTEM® (Promega, Madison, Wis.) and reversed transcribed using murine leukemia virus reverse transcriptase (Perkin Elmer, Foster City, Calif.) and oligo (dT) primers (Gibco BRL, Grand Island, N.Y.). Successful PCR reactions were 50 μL and contained 1 μM $MgCl_2$ and Taq polymerase (Perkin Elmer). Twenty-five thermal cycles of 94° C. for 1 min, 40° C. for 45 sec, and 72° C. for 1 min were used. The cycles were preceded by a 55 sec denaturization of the RT product at 95° C., followed by a 10 min extension of RT-PCR products at 72° C. More than 150 RT-PCR reactions testing ten different primer sets were required to achieve this protocol. The resulting cDNA using Primer Set 4 (FIG. 1) was TA-cloned into the pCR®II vector (Invitrogen, Carlsbad, Calif.), plasmid-containing colonies selected by blue/white screening, and amplified following instructions of the manufacturer. Restriction analyses of recovered pCR®II/cDNA plasmids revealed that four of fifty-six clones contained cDNA consistent with rabbit PepT1 cDNA (FIG. 2).

Northern Blot Analysis of cPepT1 Expression in Dog Tissue and MDCK Cells

Figure 3:
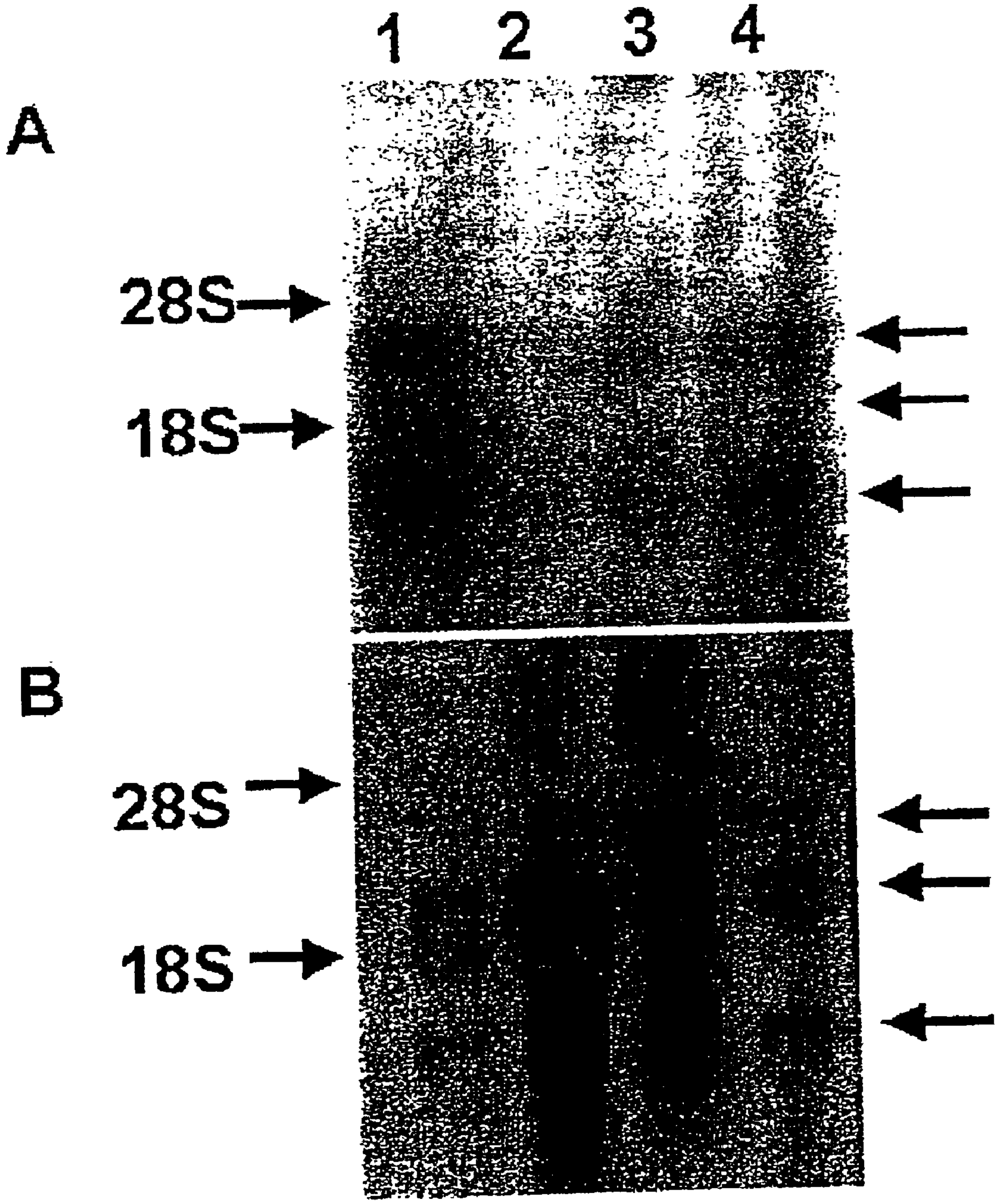
FIGS. 3A and 3B are photographs showing the representative results of Northern blot identification of cPepT1 mRNA expression by canine tissues and MDCK cells using canine intestinal epithelium-derived RT-PCR cDNA. Arrangement of RNA isolated from tissue or cell homogenates on both blots is as follows: lane 1, kidney (animal #1031A); lane 2, kidney (animal K-9-1); lane 3, MDCK cells; lane 4, jejunal epithelium (animal K-9-4).

The potential expression of cPepT1 mRNA by canine kidney, small intestinal epithelium, and immortalized kidney distal tubule epithelial cells (Madin-Darby Canine Kidney, MDCK) was evaluated by Northern analyses using cDNA derived from canine jejunal epithelium (FIG. 3). RNA were subjected to 1% gel electrophoresis in the presence of 0.02 M formaldehyde, transferred by downward capillary action to 0.45-μm nylon membranes (Hybond-N, Amersham, Arlington Heights, Ill.), and covalently cross-linked by ultra-violet light. cDNA were randomly labeled with [$^{32}$P]-CTP using a kit (Gibco BRL), purified through Sephadex-50 columns (Amersham Pharmacia, Piscataway, N.J.), and hybridized with blots at 56° C. for 18 h. The blots were then washed 2 times at 56° C. for 15 min and once at 57° C. for 10 min. Autoradiographs were exposed to blots at 80° C. for 24 h and the size of the transcript determined by regression of hybridized bands against the migration distance of 18S (1.9 kb) and 28S (4.9 kb) RNA.

Each canine tissue-derived cDNA (TA-clone 26, FIG. 3A; TA-clone 6, FIG. 3B) hybridized to three mRNA species in dog kidney, dog small intestinal epithelium, and MDCK cells. To confirm identification of PepT1 mRNA by these canine cDNAs, RNA isolated from dog kidney and liver tissues were probed for expression of PepT1 mRNA using a full-length rabbit PepT1 cDNA (FIG. 4; rabbit PepT1 cDNA supplied by Drs. F. Leibach and V. Ganapathy, Medical College of Georgia). The results also demonstrated the expression of the same three PepT1 mRNA species by dog tissues, indicating that the full-length rabbit PepT1 cDNA and the cDNA derived from canine tissue in the present study identified the same transcripts. The mean/SD of transcript sizes calculated from these three blots were 4.2/0.22, 2.75/0.26, and 1.46/0.42 kb, respectively. Collectively, these data indicate that liver, intestinal epithelial, and MDCK cells express the same size and number of PepT1 transcripts. In comparison, various tissues of chicken, sheep, cow, pig, rabbit, rat, human, and Caco2 cells are reported to express a single transcript, with the principle difference in size being between chicken (1.9) and mammalian species (2.8, 2.8, 2.9, 2.9, 3.0, 3.1, 2.9, respectively Partial Cloning and Sequence Identification of Canine PepT1 (cPepT1) cDNA from MDCK Cells To confirm the positive Northern analysis, identification of PepT1 mRNA expression using cDNA generated from dog small intestinal epithelium, RT-PCR methodologies were used to generate a PepT1 cDNA from MDCK cells. The target cDNA region was a subset of the cDNA generated by RT-PCR from canine small intestine (bp 83 to 887 of rabbit PepT1). Accordingly, PCR primers that corresponded to bp 259 to 619 of rabbit PepT1 (GenBank acc. no. U06467) were used to generate a partial-length "canine PepT1" (cPepT1) cDNA from mRNA isolated from MDCK cells. RNA was collected from cells that were plated at 30,000 cm$^2$ on rat tail collagen-coated dishes and cultured for 3 days in 10% fetal calf serum/DMEM. Reverse transcription of 5 μg of total RNA by SUPERSCRIPT®II reverse transcriptase (Gibco-BRL) was performed using random and oligo(dT) primers, per instructions of the manufacturer (Gibco-BRL). All PCR reactions contained 2 mM $MgCl_2$ and thermal cycling using Taq polymerase included 30 cycles at 94° C. for 2 min, 55° C. for 1 min, and 72° C. for 2 min. The cycles were preceded by a 10 min denaturization of the RT product at 94° C., followed by a 10 min extension of RT-PCR products at 72° C. More than one hundred RT-PCR reactions were required to achieve this protocol.

The resulting cDNA of about 380 bp was TA-cloned, into the site of pCR®II vector (as described above), amplified, bacterial colonies evaluated by blue/white screening, and pCR®II/cDNA plasmids evaluated for cDNA by Eco RI/Pst I restriction analysis (as described above). Restriction analyses of recovered plasmids revealed that six of thirty-six clones contained cDNA consistent with rabbit PepT1 cDNA. Two of the confirmed plasmids were amplified in bacteria, recovered, and sent for sequencing by the University of Florida DNA Sequencing Core Facility (Gainesville). Sequence comparisons of this 380 bp cDNA (FIG. 5) to PepT1 sequences of other species using BLAST 2.0.14. software (blast@ncbi.nlm.nih.gov) revealed that the canine sequence shares sequence homology of 79% to rabbit (bp 259 to 640; GenBank acc. no. 473375), 83% to rat (bp 213 to 593; GenBank acc. no. D50664.1), 83% to mouse (bp 213 to 589; GenBank acc. no. AF205540), and 87% to human (bp 285 to 665; GenBank acc. no. 473375 and U13173) PepT1 sequences.

Demonstration of PepT1-like Transport Activity in MDCK Cells

As seen in FIGS. 3 and 5, MDCK cells express a canine homolog of mammalian PepT1 mRNA. Potential expression of PepT1 transport activity ($H^+$-dependent, dipeptide inhibitable, low-affinity dipeptide transport) by confluent MDCK cells was evaluated using whole-cell transport techniques and glycylsarcosine (GlySar) as a model dipeptide substrate. Cells were seeded at 60,000 cells/cm$^2$ into 24-well trays that had been coated with rat tail collagen or poly-L-lysine and cultured (95%$O_2$:5% $CO_2$ at 37° C.) for 3 d in media consisting of Dulbecco's Modified Eagle Medium/10% fetal calf serum/1% antimicrobial antibacterial medium. Absorption (pmols/mg protein) of [$^3$H]-glycyl-L-sarcosine (GlySar, 6 mCi/mL, Moravek Biochemicals, Brea, Calif.) was determined using the 24-well cluster tray method and representative scintillation counting. Before transport, cells were incubated at 37° C. for 30 min in 25 mM Hepes/Tris (pH 7.5), 140 mM NaCl, 5.4 mM KCl, 1.8 mM $CaCl_2$, 0.8 mM $MgSO_4$, and 5 mM glucose (uptake buffer) to normalize intracellular amino acid and peptide pools. Transport was initiated by the addition of 0.25 mL of uptake buffer that contained 2.88 μm GlySar. After 30 min of uptake at 37° C., transport was terminated by rapid washing of cells with 4×2 mL 4° C. uptake buffer. Cellular protein was precipitated with 10% trichloroacetic acid and the supernatant recovered and counted to determine radioactivity ($^3H$) content. Cellular protein was then solubilized in 0.2 N NaOH and 0.2% SDS and quantified by the Lowry procedure, using bovine serum albumin as a standard. The amount of $H^+$-dependent GlySar absorbed was calculated as the difference between uptake in pH 6.0 and pH 7.5 uptake buffers. The amount of competitor substrate-inhibitable GlySar uptake was calculated as the quotient of GlySar uptake in the absence and presence of 10 mM competitor substrate (dipeptide or amino acid) multiplied by 100%.

GlySar uptake in the presence of an intracellularly $H^+$ gradient (extracellular pH of 6.0) was 2.3-fold higher in cells plated on collagen, and 1.7-fold higher when grown on poly-L-lysine, than uptake in pH 7.5 medium (Table 1). $H^+$-dependent uptake of GlySar by MDCK cells was inhibited by 88 or 92% by the presence of 10 mM LeuTrp or TrpLeu when grown on collagen, and 87 or 92% when grown on poly-lysine, respectively (Table 1).

TABLE 1

Influence of extracellular pH and competitor substrates on uptake of [$^3H$]-glycylsarcosine by MDCK cells cultured on collagen- or poly-L-lysine-coated trays.
Cells were cultured as described in text and uptake compared in pH 7.5 or 6.0 media that contained 2.88 [$^3H$]-glycylsarcosine for 30 min.

| n | Extracellular pH | Competitor substrate (mM) | Glysylsarcosine uptake pmol 30 $min^{-1}$ $mg^{-1}$ protein | % inhibition of pH 6.0 uptake |
|---|---|---|---|---|
| Collagen-coated | | | | |
| 5 | 7.5 | none | 19.9 ± 2.80 | na[1] |
| 5 | 6.0 | none | 65.3 ± 7.95 | 100 |
| 5 | 6.0 | LeuTrp (10) | 7.68 ± 1.37 | 11.7 |
| 5 | 6.0 | TrpLeu (10) | 5.21 ± 0.39 | 8.0 |
| 4 | 6.0 | Leucine (10) | 63.0 ± 4.00 | 96.3 |
| Poly-L-lysine-coated | | | | |
| 4 | 7.5 | none | 15.52 ± 1.06 | na |
| 5 | 6.0 | none | 42.31 ± 4.03 | 100 |
| 5 | 6.0 | LeuTrp (10) | 5.50 ± 0.58 | 13.0 |
| 5 | 6.0 | TrpLeu (10) | 3.44 ± 0.27 | 8.1 |
| 4 | 6.0 | Leucine (10) | 41.93 ± 2.70 | 100 |

[1]na, not applicable

Figure 4:
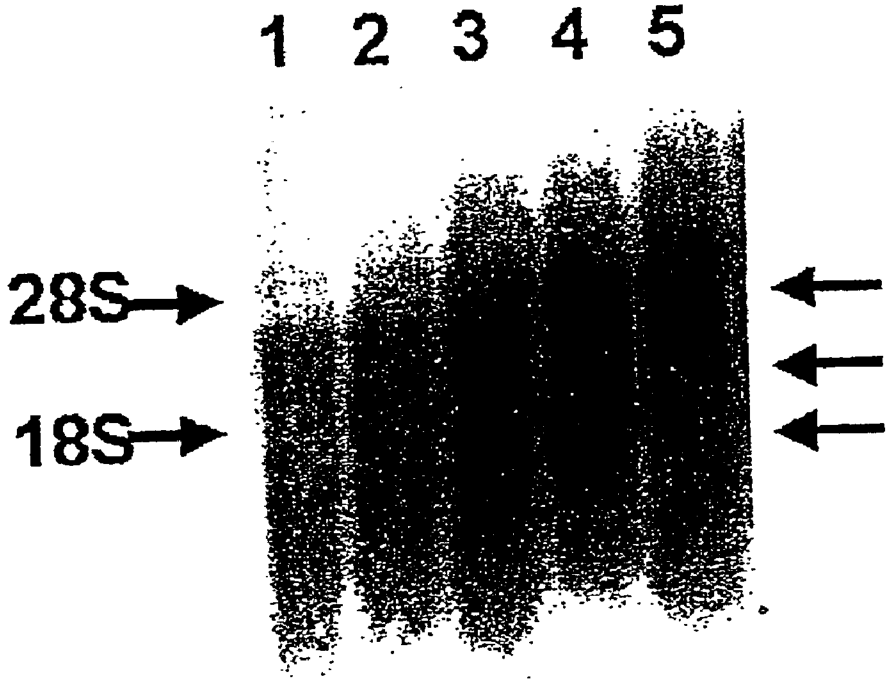
FIG. 4 is a photograph showing the representative results of Northern blot identification of cPepT1 mRNA expression in canine tissues using full-length rabbit PepT1 cDNA. Ten $\mu$g total RNA (lane 1) or 6 $\mu$g $A^+$RNA (lanes 2 to 5) were isolated from liver and kidney tissues from three animals. Lane 1, liver (animal #1042A); lane 2, liver (animal #1008A); lane 3, kidney (animal #1008A); lane 4, liver (animal #1031A); lane 5, kidney (animal #1031A).
Figure 6:
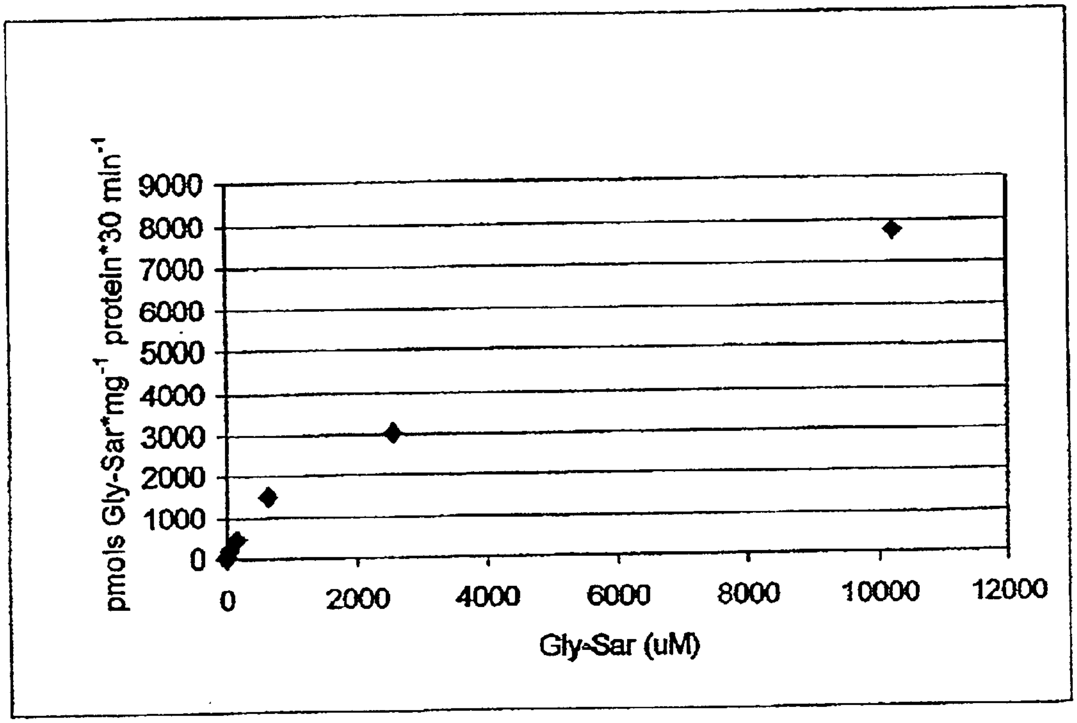
FIG. 6 is a graph illustrating the influence of extracellular GlySar concentrations on GlySar uptake by confluent MDCK cells in pH 6.0 media. By graphical evaluation, an apparent $K_m$ of about 4 mM was demonstrated. Each data point is the mean of 5 to 6 observations and all coefficients of variation were less than 15%.

To preliminarily characterize the kinetic parameters of peptide transport by MDCK cells, the uptake of GlySar in media that contained pH 6.0 and 0.00064, 0.0025, 0.010, 0.04, 0.160, 0.640, 2.56, or 10.2 mM of GlySar was measured (FIG. 6). Total GlySar uptake was by a relatively low-affinity mechanism (apparent $K_m$ of about 4.0 mM) and high uptake velocity. Collectively, these characteristics of GlySar uptake are consistent with functional activity of PepT1 expressed by other species, as opposed to high-affinity, $H^+$-dependent uptake by PepT2 (μm $K_m$). Accordingly, it is concluded that MDCK cells possess PepT1-like activity, consistent with detection of PepT1 mRNA by RT-PCR (FIGS. 1, 2, 5) and Northern blot analyses (FIGS. 3, 4).

Summary of Example 1

Separate partial-length canine PepT1 cDNAs (cPepT1) were generated by RT-PCR analyses from dog small intestinal epithelium (n=2; FIGS. 1, 2) and immortalized canine kidney cells (MDCK cells, n=1). The MDCK cDNA was sequenced (FIG. 5) and found to share 79 to 87% sequence identity with PepT1 mRNA expressed by other mammalian species. Northern blot analyses using the intestinal epithelium-derived RT-PCR cDNA confirmed expression of canine PepT1 (cPepT1) by dog tissues (liver, n=3; kidney, n=3; small intestine n=1) and MDCK cells (n=2). The identification of mRNA transcripts corresponding to PepT1 using partial-length canine-derived PepT1 cDNA (FIG. 3) was confirmed by hybridization to full-length rabbit cDNA (FIG. 4). Characterization of GlySar uptake by MDCK cells demonstrated that MDCK cells express PepT1-like activity (Table 1, FIG. 5), confirming detection of PepT1 mRNA expression by MDCK cells and use of MDCK cells as a model to characterize the function of canine PepT1.

EXAMPLE 2

Experimental Model of MDCK Cells for Evaluating the Effects of Various Peptide and Drug Substrates, and Hormones and/or Growth Factors, on the Expression of PepT1 Activity Example 1 above showed that (1) a canine homolog of PepT1 (cPepT1) mRNA cloned from epithelia of the mid small intestine (jejunum) shares high sequence identity with PepT1 expressed by several other species, (2) canine liver, kidney, and jejunal epithelium express a similar pattern of cPepT1 mRNA, and (3) MDCK cells are capable of $H^+$-dependent peptide uptake. Accordingly, MDCK cells are an appropriate model to evaluate the biochemical characteristics of cPepT1. The specific goals of this research were to (1) characterize the functional activity of low-affinity $H^+$-dependent GlySar uptake (PepT1 activity) by MDCK cells and (2) identify di- and tripeptides that are well recognized by cPepT1 (cPepT1), especially those that contain tryptophan and leucine.

Figure 7:
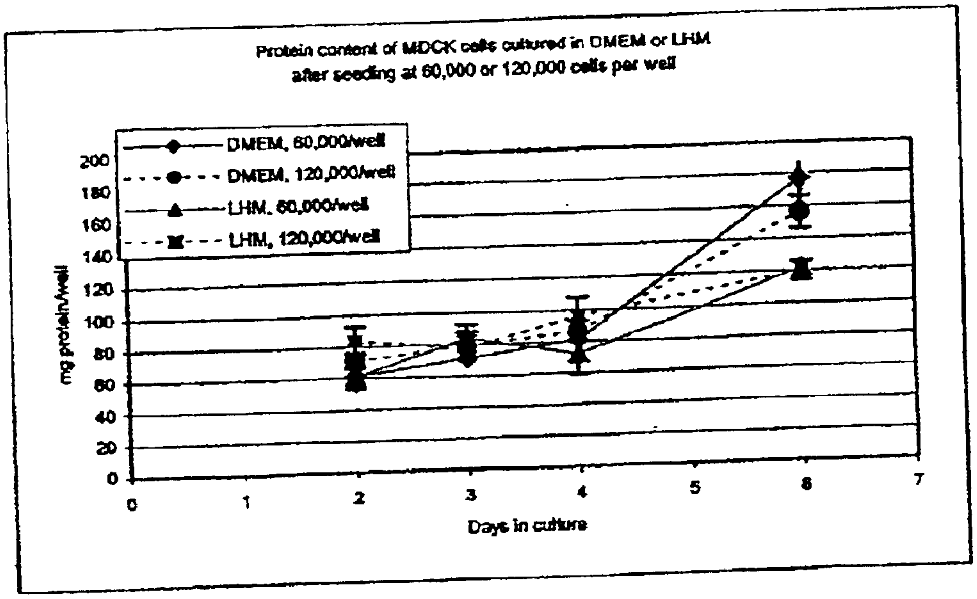
FIG. 7 is a graph illustrating the protein content of MDCK cells cultured in DMEM or LHM. Values are the means±SD of protein content of wells (n=12) of MDCK cells after seeding at 60,000 or 120,000 cells/well, culture for 1 d in DMEM, and then culture in DMEM or LHM for 1, 2, 3, or 5 d (Days 2, 3, 4 and 6, respectively). Protein content was determined by the method of Lowry, using bovine serum albumin as the standard.

Previous research (Brandsch et al., 1994, Biochem J. 299:253–260) briefly reported that $H^+$-dependent peptide uptake by MDCK cells was greater when cells were grown in a medium that contained lactalbumin hydrolysate (LHM) versus one that contained free amino acids (DMEM). Therefore, in an attempt to establish the most sensitive model possible for evaluating peptide transport systems in MDCK cells, the potential influences of LHM (peptide-containing) versus DMEM (peptide-lacking) media, and subconfluent versus confluent initial cell plating densities were compared. MDCK cells were seeded at either 60,000 cells/well (subconfluent) or 120,000 cells/well (confluent) in DMEM and, after 1 d, cultured in DMEM or LHM media for 1, 2, 3, or 5 d. The amount of protein (index of cell growth) and GlySar uptake (index of peptide uptake capacity) expressed by each well of cells was then determined. As seen in FIG. 7, the amount of cellular protein increased ($P<0.05$) for both seeding densities and media with time of culture. A time×media interaction was observed, which reflects the greater protein content of cells grown in DMEM at day 6, as compared to those grown in LHM. At days 2, 3, or 4, however, no difference in protein content was observed.

Figure 8:
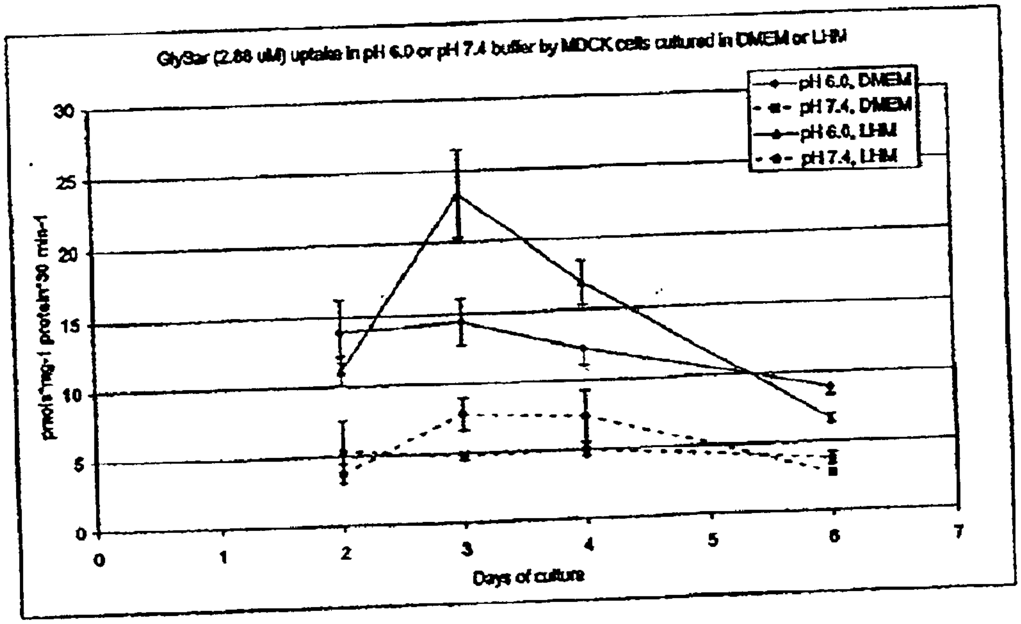
FIG. 8 is a graph illustrating GlySar (2.88 $\mu$M) uptake in pH 6.0 or pH 7.4 buffer by MDCK cells cultured in DMEM or LHM. Uptake was measured in the absence (pH 7.4) or presence (pH 6.0) of an extracellular-to-intracellular $H^+$ gradient.

The uptake of [$^3H$]-GlySar (2.88 μM, 5 μCi/mL) by the MDCK cells described in FIG. 7 was measured in the presence (pH 6.0 uptake buffer) and absence (pH 7.4 uptake buffer) of an extracellular-to-intercellular $H^+$ (proton) gradient. A representative graph (FIG. 8) compares the uptake of GlySar by cells seeded at 60,000/well and cultured in the LHM or DMEM. For both culture media, GlySar uptake in the presence of pH 6.0 was greater ($P<0.01$) than that in pH 7.4 buffer and displayed a quadratic (P<0.01) response to length of culture, reflecting a buffer×day of culture interaction (P<0.01). DMEM-cultured cells seeded at 120,000/well displayed almost identical uptake characteristics as just described for cells seeded at 60,000/well. In contrast, GlySar uptake in the presence of pH 6.0 buffer at day 3 by LHM-cultured cells was only 28% larger (quantitatively) than that observed by DMEM-cultured cells seeded at 60,000/well.

Figure 9:
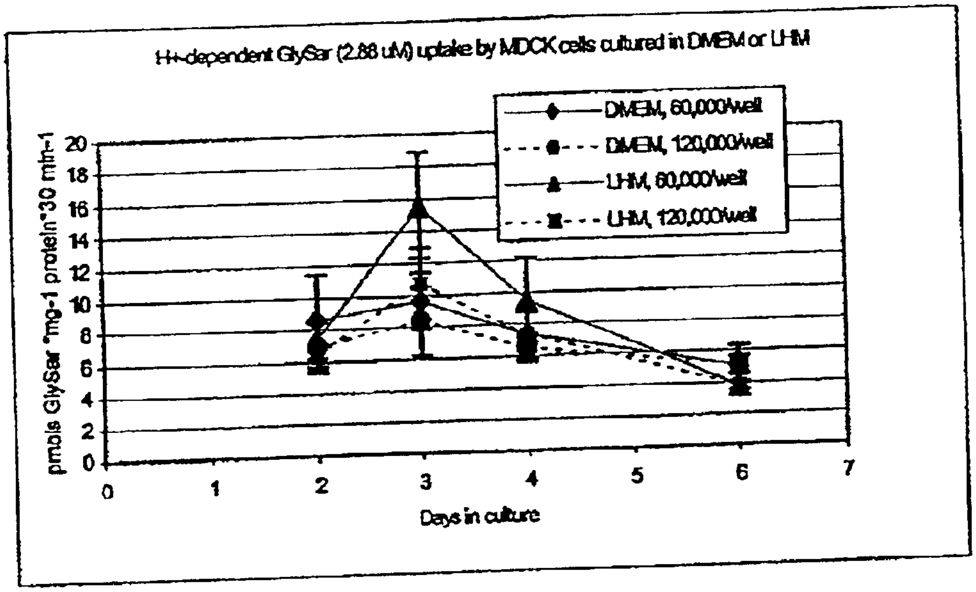
FIG. 9 is a graph illustrating $H^+$-dependent [$^3$H]-GlySar (2.88 $\mu$M) uptake by MDCK cells cultured in DMEM or LHM. Values were calculated as the difference in GlySar uptake in the presence (pH 6.0 uptake buffer) and absence (pH 7.4 uptake buffer) of an extracellular-to-intercellular $H^+$ proton gradient.

To further refine the analysis of media influence on the peptide transport capacity of MDCK cells plated at 60,000 or 120,000 cells per well, the $H^+$-dependent GlySar uptake was calculated as the arithmetic difference between uptake in pH 6.0 and pH 7.4 buffers (FIG. 9). Despite the comparable protein contents of cells observed at day 3 (FIG. 7), cells seeded at 60,000 and grown in LHM media demonstrated about 60% greater capacity for GlySar uptake as did cells grown in DMEM (FIG. 9; day×media interaction, P<0.01). For all cells, the capacity for GlySar uptake per mg of cellular protein was decreased at day 6. This difference was the result of a lesser uptake at pH 6.0 by the LHM-cultured cells, and not the result of a larger pH 7.4 uptake.

The results of this experiment indicate that culturing cells in media that contains peptides does not increase growth rate but does increase the capacity for peptide uptake if cells are seeded at 60,000/well and cultured for 2 days in LHM. As such, these data are consistent with the induction of PepT1 expression by culture peptide-containing medium and describe an optimal set of culture conditions for characterizing $H^+$-dependent peptide transport activity of the canine PepT1 transporter. These data also confirm, and more thoroughly describe, the stimulating effect of LHM versus DMEM media on peptide transport proteins that was initially reported by Brandsch et al. (1994).

Figure 10:
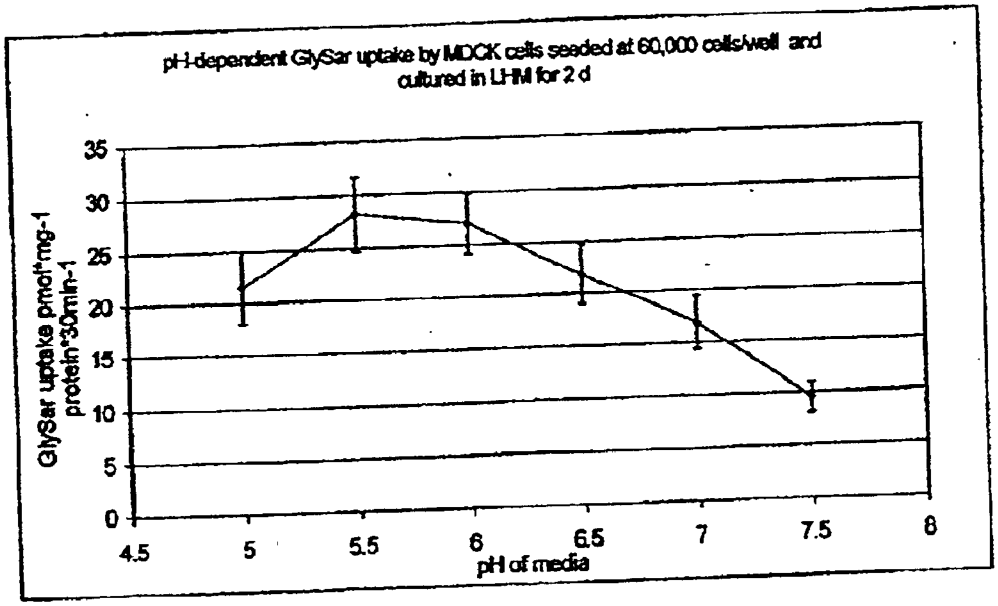
FIG. 10 is a graph illustrating pH-dependent GlySar uptake by MDCK cells seeded at 60,000 cells/well and cultured in LHM for 2 days. pH-dependent GlySar (2.88 uM) uptake by MDCK cells cultured with standard conditions. Values represent the $H^+$-dependent GlySar uptake means±SD of wells (n=16) of MDCK cells, calculated as the difference from GlySar uptake in the presence of pH 6.0 or 7.4 buffers.

Using the maximal uptake-stimulating culture parameters determined in Experiment 3, the effect of an extracellular-to-intracellular pH gradient on GlySar uptake was further evaluated to determine a pH level at which maximal GlySar uptake could be achieved, but which would replicate physiologic conditions (FIG. 10). As expected, the presence of a pH gradient stimulated (P<0.001) $H^+$-dependent GlySar uptake, in a quadratic (P<0.01) fashion. Uptake at pH 5.5 or 6.0 was about 2.7 times greater than that achieved at pH 7.5. These results are consistent with the data in FIGS. 8 and 9 and known $H^+$-dependence of mammalian peptide transport proteins. Accordingly, the use pH 6.0 buffers for the characterization of $H^+$-dependent GlySar uptake was incorporated into the standard experimental conditions.

Figure 11:
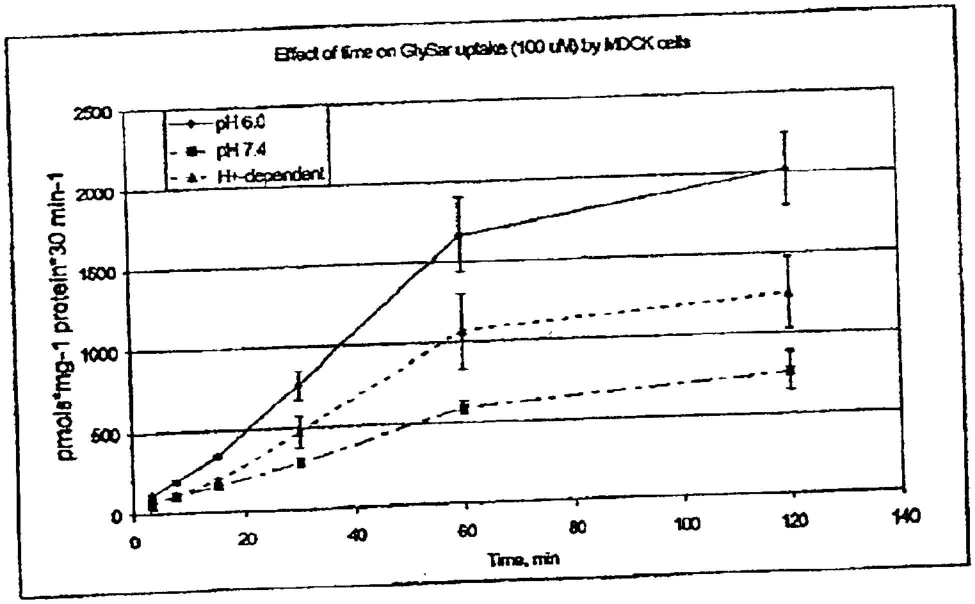
FIG. 11 is a graph illustrating the effect of time on GlySar uptake (100 $\mu$M) by MDCK cells. By-minute time course for GlySar (uptake by MDCK cells cultured with standard conditions. Mean±SD GlySar uptake wells of cells (n=6) were assayed at 3.75, 7.5, 15, 30, 60, or 120 min.

To determine the appropriate time period to measure initial (linear) rates of GlySar uptake, a by-minute time-course experiment was performed. As seen in FIG. 11, $H^+$-dependent GlySar (100 uM) uptake increased linearly for 1 h and then slowed (quadratic response, P<0.01). GlySar uptake in pH 6.0 buffer at 3.75, 7.5, 15, 30, 60 and 120 min was about 2, 2.1, 2.25, 2.65, 2.79, and 2.62 times more (P<0.001), respectively, than uptake from pH 7.4 buffer. Because uptake was proportional to time of uptake through 1 h, future experiments were conducted using a 30-min time period.

Figure 12:
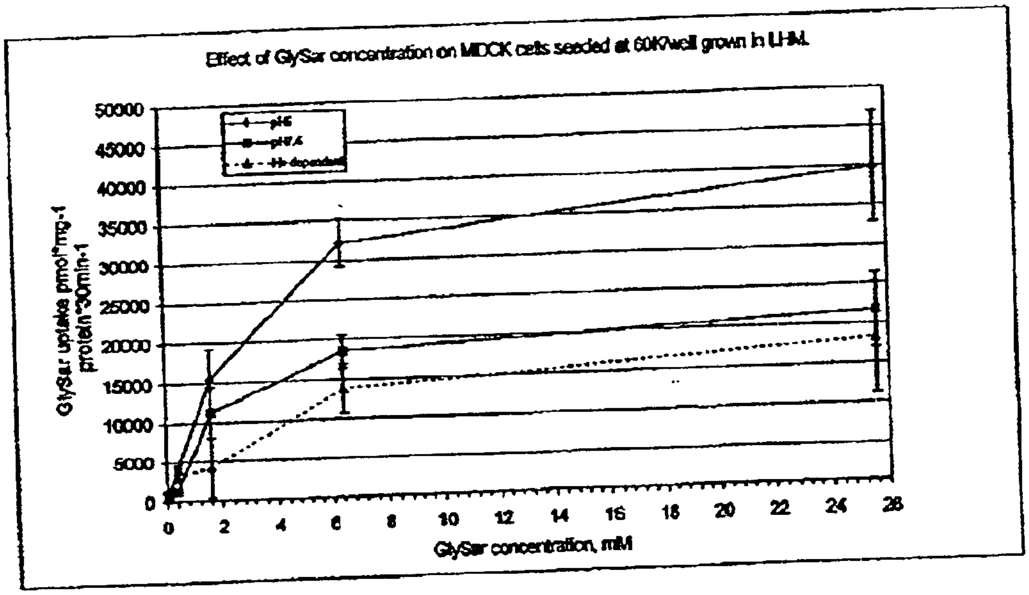
FIG. 12 is a graph illustrating the effect of GlySar concentration on MDCK cells seeded at 60K/well grown in LHM. The graph indicates the $K_m$ characterization (1.0 mM) of $H^+$-dependent GlySar uptake by MDCK cells. Each value represents the mean±SD uptake of GlySar by wells (n=8) of MDCK cells cultured using standard conditions.

To confirm that $H^+$-dependent GlySar uptake was saturable, and therefore mediated, the uptake of GlySar from pH 6.0 and 7.4 uptake buffers containing 0.025, 0.1, 0.4, 1.6, 6.4, or 25.6 mM GlySar was evaluated (FIG. 12). Uptake of GlySar was greatest (P<0.001) from the pH 6.0 buffers, at all concentrations. $H^+$-dependent GlySar uptake was saturable, consistent with an apparent $K_m$ for GlySar of about 1.1 mM. These values are consistent with our preliminary trials that estimated a $K_m$ of 1.1 mM for GlySar uptake by MDCK cells using only pH 6.0 uptake buffer and indicate that $H^+$-dependent GlySar uptake is predominately, if not completely, a result of low affinity (mM) $H^+$/peptide cotransporter activity (PepT1). As a comparative value, the reported $K_m$ of for GlySar uptake by the PepT1-expressing Caco-2 cells also is 1.1 mM. It is of interest also to note that GlySar uptake in the absence of a pH gradient (pH 7.4 buffers) also displayed linear (P<0.01) and quadratic (P<0.001) components, (1) reflects that the pH "7.4" buffer was in fact slightly acidic, (2) represents the activity of the putative basalateral peptide transporter running in "reverse", or (3) indicates the presence of a non-characterized peptide transport system. As a result of this experiment, subsequent $H^+$-dependent peptide transport trials were conducted using 100 $\mu$M GlySar, a value well below the $K_m$ but one that will result in increased transport activity, and thus, sensitivity.

Figure 13:
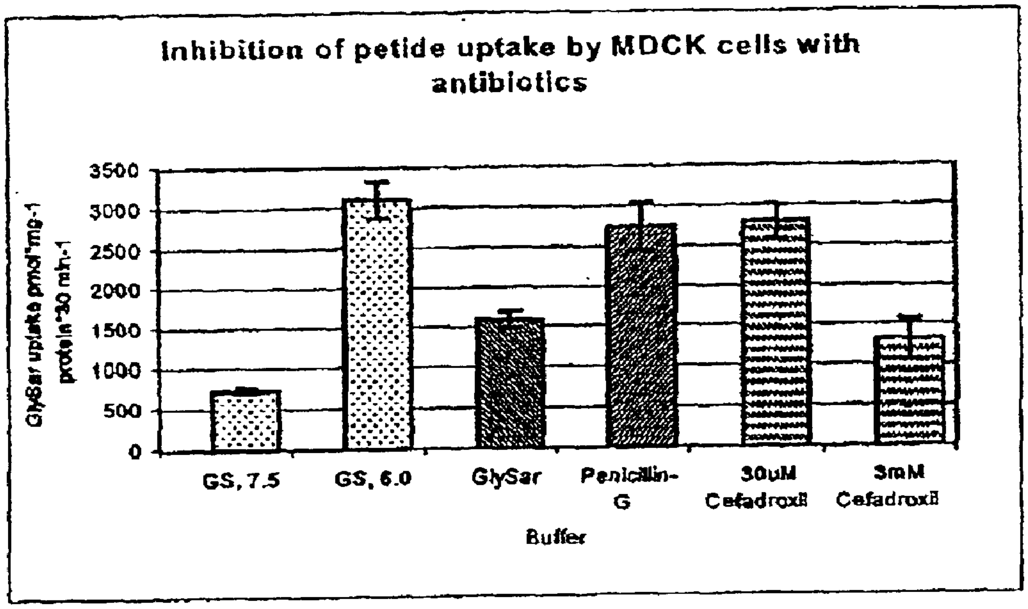
FIG. 13 is a graph illustrating the inhibition of peptide uptake by MDCK cells with antibiotics. The mean±SD are the uptake of GlySar by wells (n=5–8) of MDCK cells in the absence or presence of GlySar (1 mM) Penicillin-G (3 mM), cefadroxil (30 $\mu$M), or cefadroxil (3 mM).

Characteristic hallmarks of low affinity $H^+$/peptide cotransport activity, classically defined using membrane vesicles of several species, and more recently by functional expression studies using human, rat, and rabbit PepT1 cDNA, is the recognition of some, but not all, β-lactam antibiotics. In addition, PepT1 recognition of cefadroxil is low (the $K_i$ of cefadroxil inhibition of GlySar uptake by PepT1 is 3 mM), whereas recognition of cefadroxil by PepT2 is high (the $K_i$ of cefadroxil inhibition of PepT2 transport of GlySar is 30 $\mu$M). To determine whether MDCK cPepT1 activity shared these functional features, the uptake of 100 $\mu$M GlySar in the absence and presence of pH 7.5 and pH 6.0 buffer, and, in pH 6.0 buffers, the presence of 1 mM additional GlySar (self-inhibitor control), 3 mM Penicillin-G, 30 $\mu$M cefadroxil, or 3 mM cefadroxil was compared (FIG. 13). $H^+$-dependent GlySar uptake was not inhibited by penicillin-G or 30 $\mu$M cefadroxil, but was inhibited about 76% by 3 mM cefadroxil. As expected, the presence of 1 mM GlySar self-inhibited 100 $\mu$M GlySar uptake by 64%. These results indicate that H+-dependent uptake of GlySar by MDCK cells is by PepT1 activity.

Figure 14:
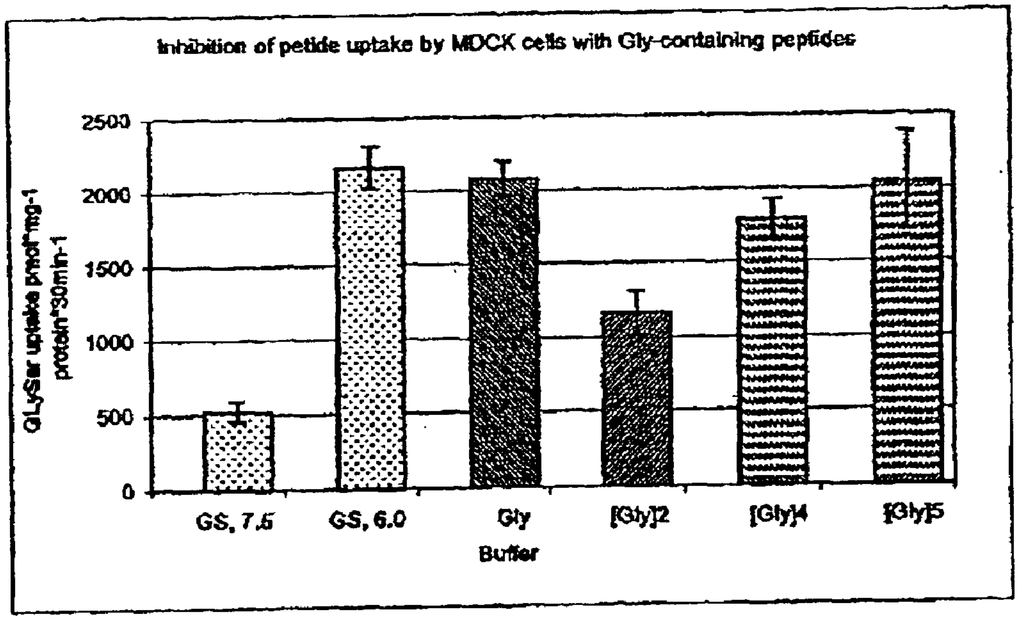
FIG. 14 is a graph illustrating the inhibition of peptide uptake by MDCK cells with Gly-containing peptides. The mean±SD uptake of GlySar by wells (n=7–8) of MDCK cells in the absence or presence of indicated competitor substrates (1 mM).

Other hallmarks of PepT1 function are the decreased ability of Gly-containing peptides to inhibit GlySar, in proportion to their length, and sensitivity to inhibition by carnosine (β-Ala-His). To determine if cPepT1 activity behaves as reported for other PepT1 activities, the relative abilities of 1 mM Gly ([$^3$H]-Gly free amino acid control), GlyGly, $[Gly]_4$, or $[Gly]_5$ to inhibit $H^+$-dependent 100 $\mu$M GlySar was determined (FIG. 14). Gly (5.0%) and $[Gly]_5$ (7.3%) did not influence uptake, whereas GlyGly inhibited and $[Gly]_4$ tended to inhibit uptake by 63 and 23%, respectively. This pattern of Gly-containing peptides to inhibit GlySar uptake in an inverse proportion to the number of glycyl residues in the canine MDCK cell model is consistent with PepT1 activities reported for other species. Similarly, GlySar uptake was inhibited 50% by 1 mM carnosine (data not shown but listed in Table 2 below).

Together with the molecular identification of PepT1 mRNA expression in MDCK cells using full-length rabbit cDNA and our canine RT-PCR product (See Example 1 data), the above biochemical characterization data indicate that $H^+$-dependent GlySar uptake activity in MDCK cells is consistent with the low-affinity, high-capacity of the PepT1 transport protein. Collectively, the above experiments resulted in the generation of an experimental regimen for the culture and determination of $H^+$-dependent peptide transport activity in MDCK cells, with which to evaluate the relative substrate preferences of canine PepT1 (cPepT1).

Accordingly, the following general regimen was used to perform a series of experiments that evaluated the relative abilities of candidate di-(primarily) and tri-peptides to inhibit GlySar uptake by endogenously expressed cPepT1 in MDCK cells:

1. Sixty thousand cells/well were plated into collagen-coated 24-well trays and cultured at 37° C. in an atmosphere of 95% air/5% $CO_2$ in DMEM/10% FCS that contained antibiotics for 1 day.
2. The media was removed and cells were cultured in LHM/10% FCS/antibiotics for 1 day.
3. The media was removed and cells cultured in LHM/10% FCS (no antibiotics) for 20 h.
4. The media was removed and cells cultured for 30 min in air at 37° C. in depletion medium (25 mM Hepes/Tris (pH 7.5), 140 mM NaCl, 5.4 mM KCl, 1.8 mM CaCl2, 0.8 mM MgSO4, and 5 mM glucose, to normalize intracellular nutrient pools.
5. Transport was initiated by replacing depletion medium with uptake medium (depletion medium adjusted to pH 6.0 or kept at pH 7.4) that contained 100 μM GlySar (at a specific activity of 5 μCi/mL, with [$^3$H]-GlySar supplying 2.88% of total GlySar substrate) and (or) 1 mM of inhibiting peptide.

An inhibitory substrate concentration of 1 mM was selected because the literature indicates that typical $K_m$ values for PepT1 ranges from 0.5 to 5 mM. Therefore, by selecting an inhibitor concentration of 1 mM (not expected to completely inhibit uptake), our goal was to more finely delineate the relative abilities of candidate inhibitors than if the typical 5 mM inhibitor concentration (expected to achieve close to 100% inhibition of GlySar uptake) was used. Candidate peptides were selected based on their containing Trp, Leu, Met, and (or) Arg, substrates. In total, 23 inhibitory peptides and 2 drug compounds were screened using this protocol.

Figure 15:
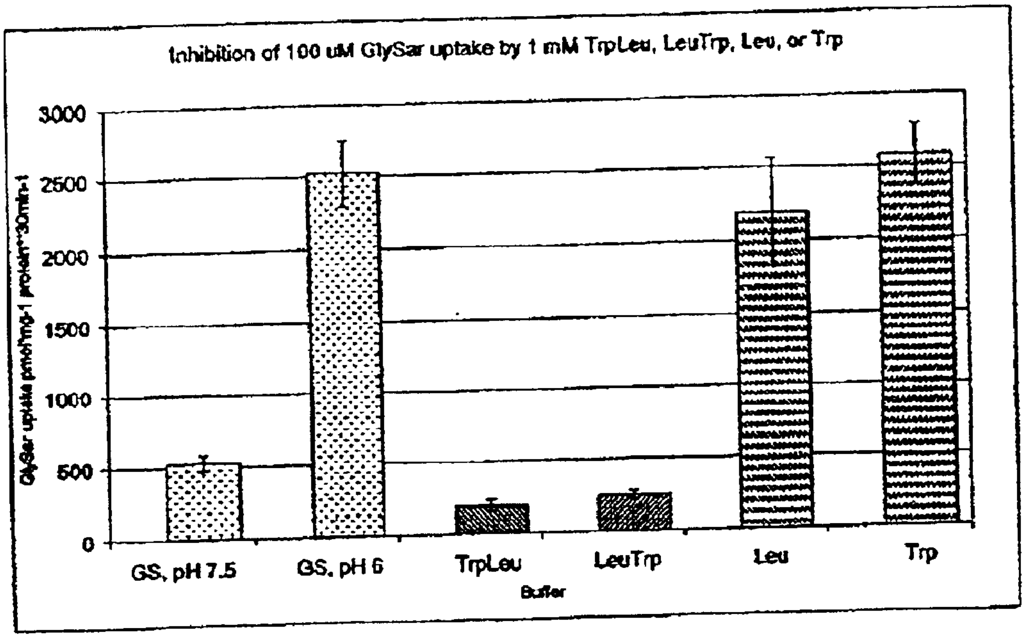
FIG. 15 is a graph illustrating the inhibition of 100 $\mu$M GlySar uptake by 1 mM TrpLeu, LeuTrp, Leu, or Trp in the absence (pH 7.5) and presence (no pH designation) of a proton gradient and 1 mM of indicated substrates. Values are the mean±SD uptake of GlySar by wells (n=7–8) of MDCK cells.

To determine the potential of Trp and Leu absorption as dipeptides by cPepT1, the ability of TrpLeu versus LeuTrp dipeptides to inhibit 100 μM GlySar uptake was evaluated (FIG. 15). The presence of either TrpLeu or LeuTrp in the pH 6.0 uptake buffer abolished $H^+$-dependent GlySar uptake by 117% or 114%, respectively. In contrast, neither Leu nor Trp significantly influenced $H^+$-dependent GlySar uptake. These results indicate that a lesser concentration of inhibitor would be required to delineate the relative recognition of TrpLeu and LeuTrp by cPepT1. With regard to the mechanism of $H^+$-independent GlySar uptake observed throughout these experiments, it is of interest to note that TrpLeu and LeuTrp inhibited $H^+$-independent GlySar uptake by 36% and 46%, respectively.

Figure 16:
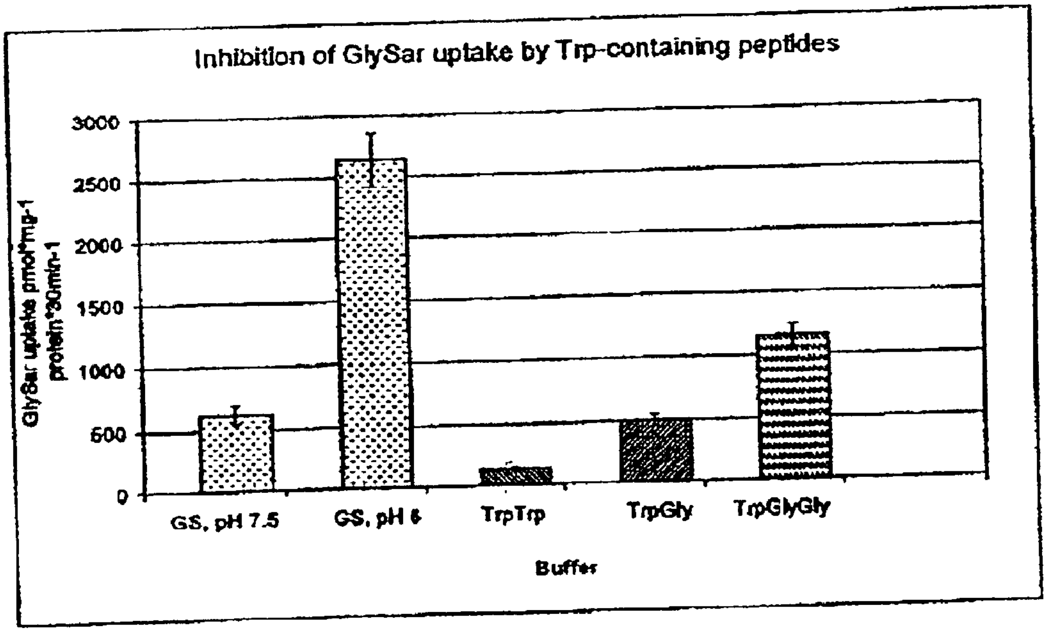
FIG. 16 is a graph illustrating the inhibition of 100 $\mu$M GlySar uptake by MDCK cells in the absence (pH 7.5) and presence (no pH designation) of a proton gradient and 1 mM of Trp-containing peptides. Values are the mean±SD uptake of GlySar by wells (n=7–8) of MDCK cells.

To further evaluate the potential of Trp to be absorbed in the form of peptides by cPepT1, the ability of TrpTrp, TrpGly, and TrpGlyGly to inhibit GlySar uptake was compared (FIG. 16). As observed for TrpLeu (FIG. 15), TrpTrp abolished $H^+$-dependent GlySar uptake and inhibited $H^+$-independent uptake by about 22%. TrpGly abolished $H^+$-dependent GlySar uptake but did not influence $H^+$-independent uptake. The tripeptide TrpGlyGly also significantly inhibited GlySar uptake, but to a lesser extent (73%) than did TrpTrp or TrpGly.

To determine the relative potential of other amino acids (Met, Arg, Lys, Phe, for example) to be absorbed in the peptide-bound form, additional GlySar competitive inhibition experiments were conducted using the above-described regimen and a variety candidate peptides at 1 mM. The results of these experiments are summarized in Table 2, which also includes those experiments described in FIGS. 13, 14, 15, and 16 for comparative purposes.

TABLE 2

Influence of 1 mM extracellular peptides and antibiotics on 100 μM glycylsarcosine (GlySar) uptake[1] by MDCK cells.

| Extracellular Substrate (1 mM) | % inhibition of $H^+$-dependent GlySar uptake[4] | n |
|---|---|---|
| Positive control (model) substrates | | |
| GlyGly | 89 | 8 |
| $[Gly]_4$ | 19 | 8 |
| $[Gly]_5$ | 9 | 8 |
| Carnosine (β-AlaHis) | 50 | 8 |
| Penicillin-G | 0 | 8 |
| Cefadroxil[2] | 0 | 6 |
| Cefadroxil[3] | 59 | 5 |
| Treatment substrates 100% inhibition | | |
| GlnGln | 100 | 8 |
| GlyLeu | 115 | 8 |
| GlyMet | 114 | 8 |
| LeuMet | 114 | 8 |
| LeuTrp | 113 | 8 |
| MetLeu | 122 | 8 |
| MetMet | 100 | 8 |
| MetPhe | 100 | 8 |
| MetPro | 100 | 8 |
| TrpLeu | 116 | 8 |
| TrpTrp | 119 | 7 |
| <100% inhibition | | |
| GlnGlu | 83 | 8 |
| MetGlu | 93 | 8 |
| MetLys | 88 | 8 |
| TrpGly | 88 | 7 |
| MetGlyMetMet (SEQ ID NO:10) | 50 | 8 |
| TrpGlyGly | 33 | 7 |
| LeuArg | 32 | 8 |
| ArgLeu | 32 | 8 |

[1] pmol $mg^{-1}$ protein 30 $min^{-1}$
[2] 30 μM
[3] 3 mM
[4] That portion of the % inhibition value that exceeds 100, likely represents the ability to inhibit $H^+$-independent GlySar uptake.

The inhibitors are listed within groupings in order of their relative ability to inhibit 100 μM of GlySar uptake. In addition to the listed peptides, the constituent free amino acids were tested within the appropriate experiment to evaluate whether the peptide-bound or free amino acid was responsible for any affect on GlySar uptake. As expected, the presence of 1 mM constituent free amino acid did not influence GlySar uptake. Inhibition percentages of 50% indicate that the inhibitor substrate was recognized at least as well as was GlySar, given that the $K_m$ of GlySar was determined to be about 1 mM (FIG. 12) and that the substrate was present at 1 mM. Of the 19 treatment peptides evaluated, eleven abolished $H^+$-dependent GlySar uptake, with seven of these also displaying the ability to inhibit $H^+$-independent GlySar uptake. Of the remaining eight peptides tested, four displayed greater than 80% inhibition while four inhibited GlySar uptake by 50% or less. These results indicate that a wide variety of peptides of nutritionally important constituent amino acids are recognized by cPepT1.

Figure 17:
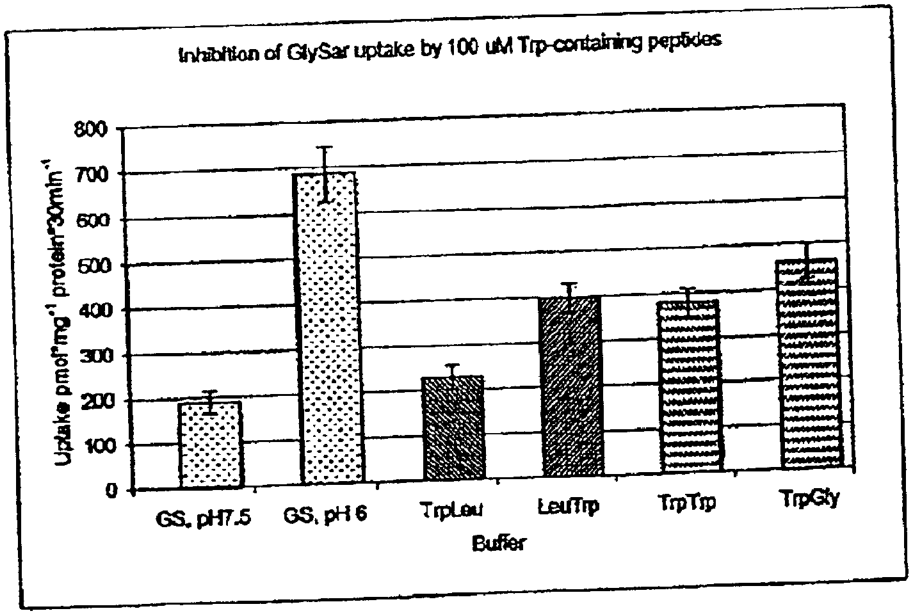
FIG. 17 is a graph illustrating the inhibition of 100 $\mu$M GlySar uptake by MDCK cells in the absence (pH 7.5) and presence (no pH designation) of a proton gradient and 100 $\mu$M of Trp-containing peptides. Values are the mean±SD uptake of GlySar by wells (n=8) of MDCK cells.

Overall, the observation that cPepT1 activity was sensitive to a number of substrates is typical of PepT1 function. However, what was surprising was the large number of peptides that completely inhibited GlySar uptake. To establish a more sensitive relative inhibitory order among peptides that inhibited GlySar uptake by more than 80%, and, therefore, a more accurate potential for recognition, fourteen peptides were re-screened for their ability to inhibit 100 μM GlySar uptake using the same cell culture and transport regimen but using only 10% of the previous inhibitor concentration (100 μM). The data from an experiment to directly compare the ability of 100 μM Trp-containing peptides are shown in FIG. 17. All Trp-containing peptides inhibited $H^+$-dependent GlySar uptake. However, TrpLeu inhibited more (92%) than did LeuTrp (58%), TrpTrp (62%), or TrpGly (45%). These values and the results of other experiments comparing the relative ability of Leu-, Met-, and Arg-containing peptides are listed in Table 3.

TABLE 3

Influence of 100 μM extracellular peptides on 100 μM glycylsarcosine (GlySar) uptake[1] by MDCK cells.

| Extracellular substrate (100 μM)[2] | % inhibition of $H^+$-dependent GlySar uptake | n |
|---|---|---|
| Trp-containing peptides | | |
| TrpLeu | 92 | 8 |
| TrpTrp | 62 | 8 |
| LeuTrp | 58 | 8 |
| TrpGly | 45 | 8 |
| Leu-containing peptides | | |
| TrpLeu | 94 | 8 |
| LeuMet | 80 | 8 |
| MetLeu | 77 | 8 |
| GlyLeu | 65 | 8 |
| Met-containing peptides | | |
| MetMet | 85 | 8 |
| MetPhe | 84 | 8 |
| MetGlu | 31 | 8 |
| MetLys | 30 | 8 |
| Arg-containing peptides | | |
| ArgLeu | 49 | 8 |
| LeuArg | 8.9 | 8 |
| ArgTrp | 8.9 | 8 |

[1]pmol $mg^{-1}$ protein 30 $min^{-1}$
[2]Data are grouped by experiment

Overall, four of the peptides inhibited GlySar uptake by at least 80%, six by more than 40%, and four less than 40%, thus establishing a relative ranking for recognition by cPepT1. Among the five Trp-containing peptides (FIG. 17, Table 3), TrpLeu demonstrated the greatest ability to inhibit GlySar uptake. TrpLeu also demonstrated the greatest ability to inhibit GlySar uptake (94%) among the Leu-containing peptides. Among the Met-containing substrates that were directly compared within the same experiment, the neutral peptides, MetMet and MetPhe, inhibited more GlySar uptake than did the anionic (MetGlu) or cationic (MetLys) carboxyl residues. Interestingly, as a group the Arg peptides demonstrated the least inhibitory ability, seemingly in keeping with the apparent lesser recognition by PepT1 of substrates with charged residues. However, it is of interest to note that 100 μM ArgLeu demonstrated a much greater ability to inhibit GlySar uptake than did LeuArg (49 versus 8.9%).

Figure 18:
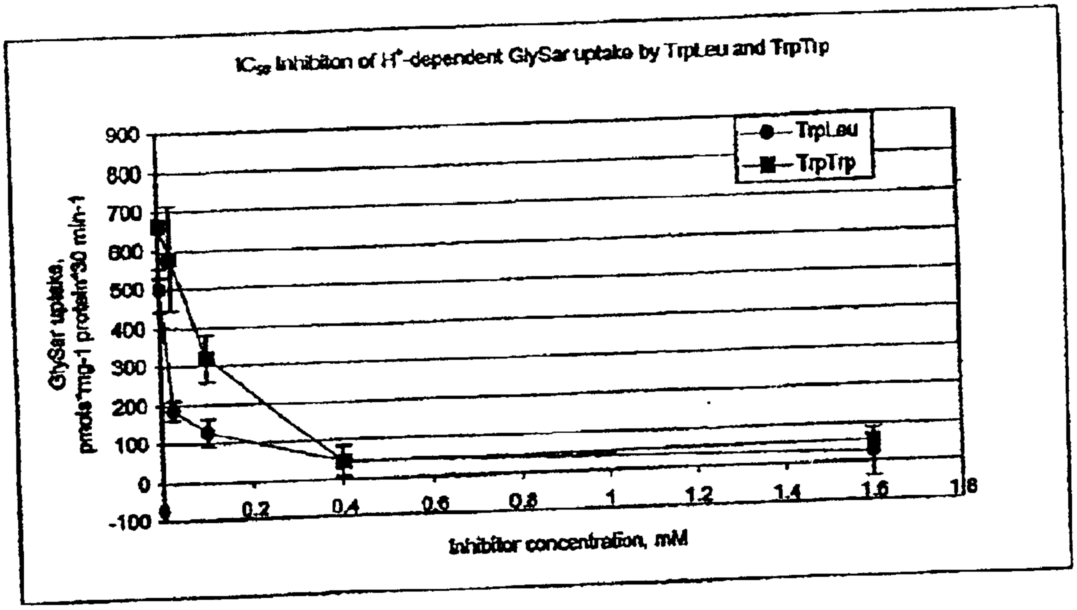
FIG. 18 is a graph illustrating the $IC_{50}$ inhibition of $H^+$-dependent GlySar uptake by TrpLeu and TrpTrp. K, values were determined for inhibition of $H^+$-dependent 100 $\mu$M GlySar uptake by MDCK cells in the presence of 0, 0.025, 0.1, 0.4, or 1.6 mM TrpTrp or TrpLeu. Values are the mean±SD uptake of GlySar by wells (n=6–8) of MDCK cells.

To confirm the relative ranking of TrpLeu>TrpTrp inhibition of GlySar (Tables 2 and 3), Michaelis-Menton constants for substrate inhibition ($K_i$) of GlySar uptake by TrpLeu and TrpTrp were generated by graphical analyses of $IC_{50}$ experiments (FIG. 18). In keeping with the results achieved in the 100 μM-inhibition studies, TrpLeu inhibited GlySar uptake at lower concentrations than did TrpTrp ($K_i$=0.2 versus 0.75 μM, respectively).

Collectively, the results of cPepT1 competitive inhibition trials using MDCK cells indicate that TrpLeu is better recognized by cPepT1 than any other tested peptide. The results also indicate that a number of Trp-, Leu, and Met-containing peptides also are well recognized by cPepT 1. Ultimately, in the intestinal environment, it is the combination of recognition by the transporter and relative resistance of the peptide to luminal and membrane-bound peptidases that will determine how much of a given peptide will be absorbed. In this regard, there is some evidence to suggest that Gly-X peptides are more resistant than other peptides, especially by blood and renal peptidases. If so, then GlyLeu may be a better candidate substrate than TrpLeu to supply Leu. Similarly, tripeptides, as a group, are thought to be relatively resistant to hydrolysis. Thus, more TrpGlyGly may prove to be absorbed in larger amounts by the intestine than TrpLeu.

An important result of this set of experiments was the establishment of a sensitive experimental regimen/model to evaluate potential affecters of peptide transport capacity. Accordingly, this experimental model of MDCK cells grown in LHM affords an opportunity to evaluate the effects of various peptide and drug substrates, and hormones and (or) growth factors, on the expression of PepT1.

Thus, the culture of MDCK cells in LHM versus DMEM results in an increase of $H^+$-dependent GlySar uptake ($K_m$=1.1 mM) that is consistent with mammalian PepT1-like activity. Using this stimulated model, the ability of twenty-three di- and tripeptides at 1 mM, and fourteen at 100 μM, extracellular concentrations were screened for their ability to inhibit 100 μM GlySar uptake, as an indicator of recognition by PepT1. Of the Trp- and (or) Leu-containing peptides evaluated, TrpLeu ($K_i$=0.2 μM) and LeuTrp ($K_i$=0.75 μM) demonstrated the greatest ability to inhibit GlySar uptake, with TrpLeu demonstrating a relatively higher affinity (lower $K_i$) for PepT1. Of the Met-containing peptides evaluated, four (MetMet, MetPhe, LeuMet, MetLeu) appear particularly well recognized by PepT1. In contrast, as a group, Arg-containing peptides displayed the least inhibition of PepT1 activity. Overall, these results indicate that ePepT1 is capable of recognizing a variety of di- and tripeptides, including, for example, those that contain leucine and tryptophan.

EXAMPLE 3

Experimental Model to Determine whether the $H^+$/peptide Transport Capacity Expressed by MDCK Cells Is Sensitive to Substrate Regulation Trial 1

Examples 1 and 2 above demonstrated that Madin-Darby canine kidney (MDCK) cells express PepT1 mRNA and characterized $H^+$-dependent biochemical properties. Therefore, MDCK cells were chosen as the experimental model to determine whether the $H^+$/peptide transport capacity expressed by MDCK cells is sensitive to substrate regulation. Research from Example 2 demonstrated that MDCK cells grown in lactalbumin hydrolysate medium (LHM) had elevated levels of peptide uptake capacity. Accordingly, to avoid potential confounding effects of the peptide-containing LHM and individual treatment peptides, DMEM (contains no peptides) and not LHM was selected as the appropriate medium to test the influence of extracellular peptides on canine PepT1 functional capacity of MDCK cells. GlyPhe was selected as a substrate because it has been reported to increase brush border membrane content of PepT1, (Shiraga T, Miyamoto K, Tanaka H, Yamamoto H, Taketani Y, Morita K, Tamai I, Tsuji A, Takada E. Cellular and molecular mechanisms of dietary regulation on rat intestinal H+/peptide transporter PepT1. *Gastroenterology*

1999; 116:354–362), whereas Phe and Gly were tested as constituent free amino acid treatment controls. Carnosine was selected because of its high content in meat-based diets.

Cell culture.

All cells were plated (60,000/2 $cm^2$ well) and cultured (95% air/5% $CO_2$, 37° C.) for 24 h in Dulbecco's Modified Eagle Media/10% fetal calf serum (FCS)/1%Antibiotic/Antimicrobial solution (ABAM) (DMEM media). Following these initial common culture conditions, cells then were cultured in DMEM, or DMEM that contained 10 mM of Camosine, GlyPhe, Phe, or Gly. Media were changed every 24 h. Media treatments (n=8) were as follows:

DMEM

DMEM+10 mM Carnosine

DMEM+10 mM GlyPhe

DMEM+10 mM Phe

DMEM+1mM G1

Uptake measurements.

The measurement of [$^3$H]Glysarcosine uptake was performed by using a 24-well cluster tray method (Kilberg M S. Measurement of amino acid transport by hepatocytes in suspension and monolayer culture. *Methods Enzym* 1989; 173:564–575. Matthews J C, Aslanian A, McDonald K K, Yang W, Malandro M S, Novak D A, Kilberg M S. An expression system for mammalian amino acid transport using a stably maintained episomal vector. *Anal Biochem* 1997; 254:208–214), and used in Examples 1 and 2. Cells were cultured for 30 min in air at 37° C. in depletion medium (25 mM Hepes/Tris (pH 7.5), 140 mM NaCl, 5.4 mM KCl, 1.8 mM CaCl2, 0.8 mM $MgSO_4$, and 5 mM glucose), to normalize intracellular nutrient pools before transport. The transport assays are initiated by replacing depletion medium with uptake medium (Depletion medium adjusted to pH 6.0) that contained 100 $\mu$M GlySar (5 $\mu$Ci/mL, with [$^3$H]-GlySar supplying 2.88% of total GlySar). After a 30 minute incubation period, transport was terminated with four rinses of 4° C. depletion medium (pH 7.5). Two hundred and twenty $\mu$L of 10% trichloroacetic acid was added to each well, and the radioactivity of the supernatant quantified by liquid scintillation counting. The cells of each well are solubilized in 0.2 N NaOH/0.2% SDS and the protein quantified by using the modified Lowry assay, using bovine serum as a standard. Id. Peptide uptake will be reported as pmol* $mg^{-1}$ protein* 30 $min^{-1}$. Uptake measurements were taken after 24, 48, and 72 hours of culture in treatment media.

Results.

Figure 19:
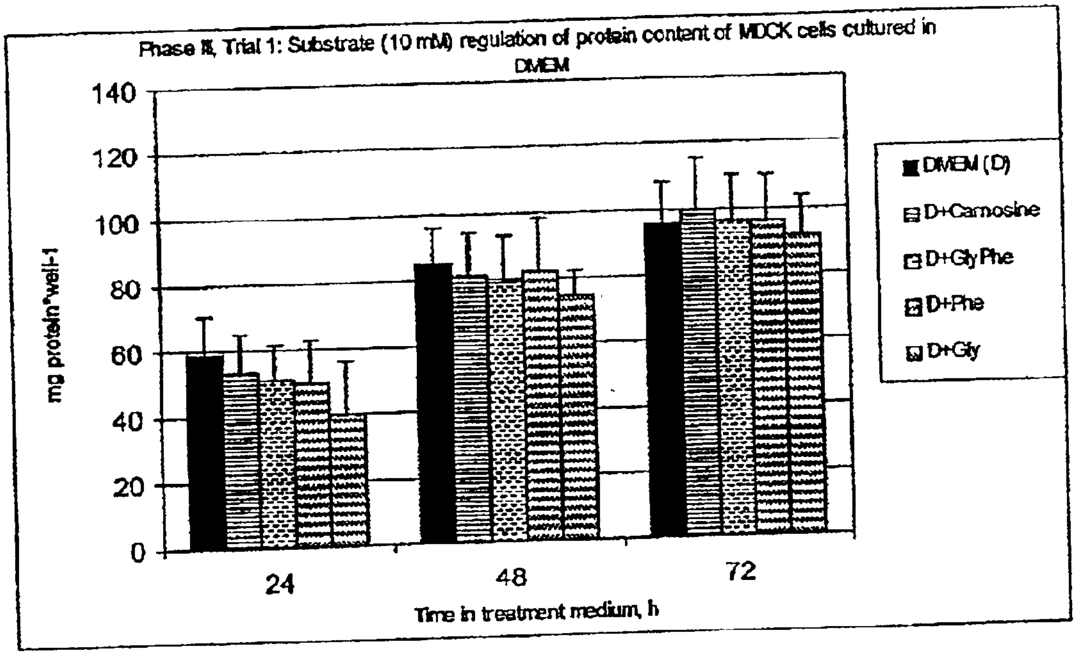
FIG. 19 is a graph illustrating substrate (10 mM) regulation of protein content of MDCK cells cultured in DMEM. In particular, the influence of 10 mM carnosine, glycylphenylalanine (GlyPhe), Phe, or Gly supplementation of DMEM on protein content of MDCK cells was measured.
Figure 20:
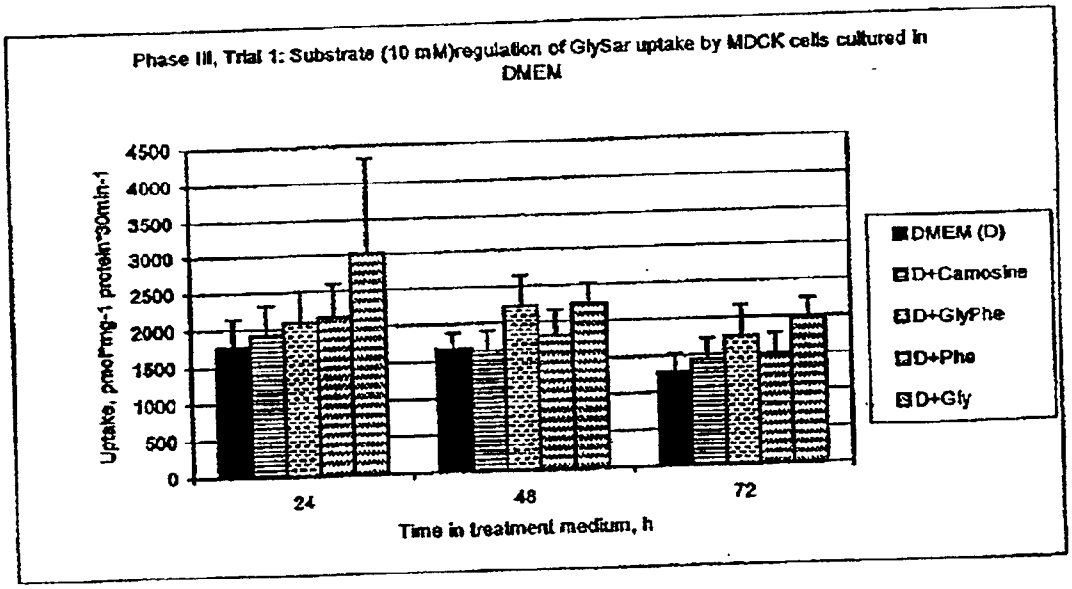
FIG. 20 is a graph illustrating substrate (10 mM) regulation of GlySar uptake by MDCK cells cultured in DMEM. In particular, the influence of 10 mM carnosine, glycylphenylalanine (GlyPhe), Phe, or Gly supplementation of DMEM on $H^+$-dependent uptake of [$^3$H]Glycylsarcosine (GlySar) by MDCK cells was measured.

The previous research characterizing $H^+$-dependent peptide transport by MDCK cells (Example 2 above) clearly showed that transport velocity is dependent on protein content. Therefore, to make a valid comparison of various treatment parameters on GlySar uptake, the protein content of compared treatment groups must not differ. Accordingly, the influence of culture media on MDCK cellular protein was evaluated (FIG. 19). All media treatments supported cellular growth from 1 to 3 d and no difference in protein content among treatments was observed. Similarly, no difference in uptake velocity (capacity) was observed among treatment groups, for any culture period (FIG. 20).

Trial 2

The results from Trial 1 suggest that either canine PepT1 is not sensitive to substrate regulation or that the substrates and(or) stimulation time were inadequate to influence $H^+$-dependent peptide uptake in MDCK cells. Again, DMEM was selected as the basal medium to allow the effect of individual peptides on peptide transport activity to be evaluated. To evaluate the latter two possibilities, a second trial was conducted that included a culture period of 9 d. GlySar was added as another potential affecter of $H^+$-dependent peptide transport capacity because 10 mM GlySar it is reported capable of stimulating increased PepT1 activity (Adibi S. The oligopeptide transporter PepT1 in human intestine: biology and function. *Gastroenterology* 1997; 113:332–340) in Caco-2 cells. GlyPro was added as a treatment because of its high content in muscle tissue, thus is likely to be abundant in meat-based diets.

Cell culture.

The MDCK cell line was maintained as described previously in the Methods section of Trial 1. Following initial and common culture conditions, cells were cultured in DMEM, or DMEM that contained 10 mM GlySar, GlyPro, GlyPhe, or Carnosine. Media were changed every 24 h. Media treatments (n=8) were as follows:

DMEM

DMEM+10 mM GlySar

DMEM+10 mM GlyPro

DMEM+10 mM GlyPhe

DMEM+10 mM Carnosine

Uptake measurements.

The measurement of [$^3$H]Glysarcosine uptake was performed by using the 24-well cluster tray method as previously described in the Methods section of Trial 1. Peptide uptake will be reported as pmol* $mg^{-1}$ protein* 30 $min^{-1}$. Uptake measurements were taken after 4, 12, 24, 36, 72, 120, 168, and 216 hours of culture in treatment media.

Results.

Figure 21:
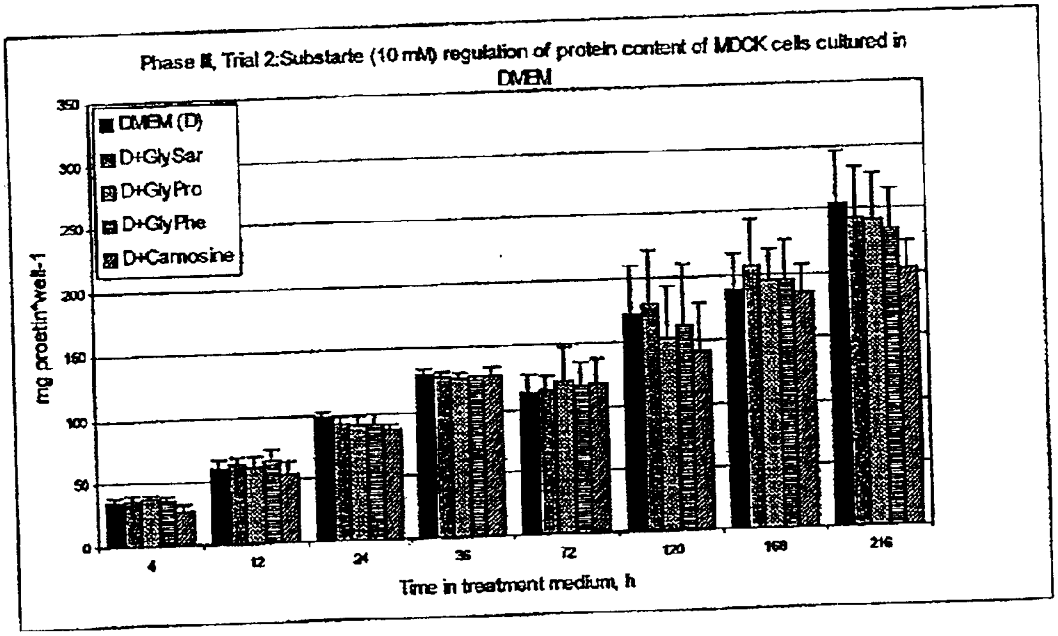
FIG. 21 is a graph illustrating substrate (10 mM) regulation of protein content of MDCK cells cultured in DMEM. In particular, the influence of 10 mM glycylsarcosine (GlySar), glycylproline (GlyPro), glycylphenylalanine (GlyPhe), or carnosine of DMEM on protein content of MDCK cells was measured.
Figure 22:
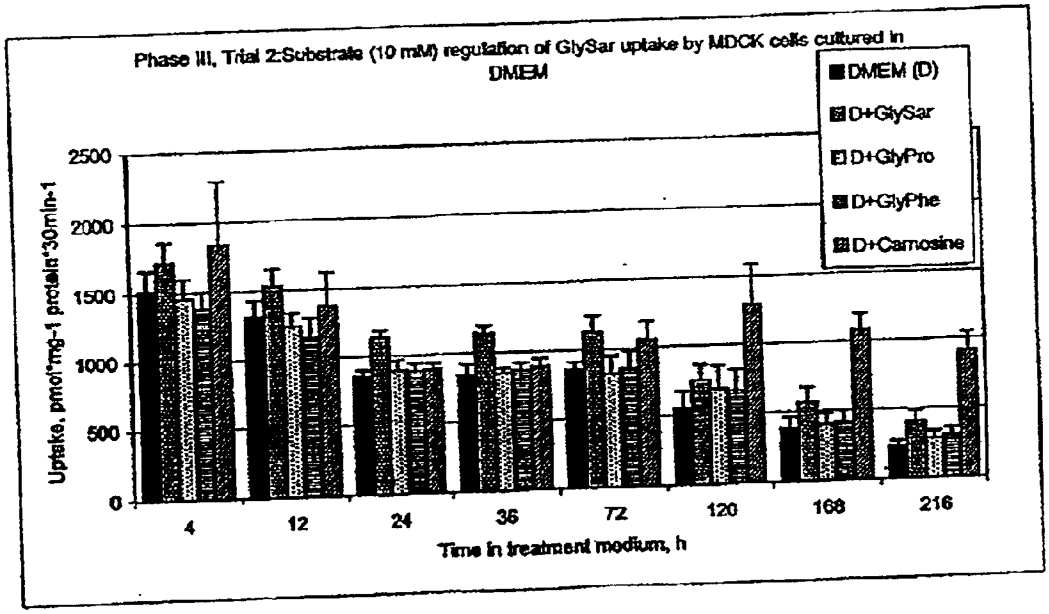
FIG. 22 is a graph illustrating substrate (10 mM) regulation of GlySar uptake by MDCK cells cultured in DMEM. In particular, the influence of 10 mM glycylsarcosine (GlySar), glycylproline (GlyPro), glycylphenylalanine (GlyPhe), or carnosine on $H^+$-dependent uptake of [$^3$H] Glycylsarcosine (GlySar) by MDCK cells was measured.

Protein content in all treatment groups increased linearly from 4 to 216 h (9 d) of culture, for all treatment groups (FIG. 21). However, within a culture period, protein contents of treatment groups did not differ. Over the 216-h culture period, protein increased about 4.5 times, from about 40 to 220 $\mu$g/well. In contrast to Trial 1 results, media treatment did influence GlySar uptake capacity (FIG. 22). In addition, a treatment×time effect was observed that represents differences in the time of culture required for GlySar and carnosine treatment stimulation of GlySar uptake capacity. Specifically, GlySar containing DMEM culture treatment resulted in an increase in GlySar uptake capacity of about 30% over DMEM control media by 24 h of culture time. This level of increase was maintained through 216 h. In contrast, culture in carnosine-containing media did not result in a significant (23%) increase of GlySar uptake capacity over that by DMEM-cultured cells until 72 h of culture. This stimulation then steadily increased to 291% over 216 h of culture. The nature of stimulated uptake between the two peptide substrates also differed. That is, the magnitude of carnosine-stimulated GlySar uptake was essentially constant from 72 to 216 h, whereas that for GlySar culture decreased during this period. Collectively, these data indicate that $H^+$-dependent peptide transport in cultured MDCK cells can be stimulated by at least two of PepT1 substrates, GlySar and carnosine.

Trial 3

The data from Trial 2 indicate that $H^+$-dependent GlySar uptake capacity by fed MDCK cells can be upregulated by the inclusion of 10 mM GlySar for at least 24 h and 10 mM carnosine for at least 72 h. It is of equal interest to understand if $H^+$-dependent GlySar uptake capacity is sensitive to nutrient deprivation and(or) stimulation by glucocorticoids. A preliminary study indicates that fasting increases the expression of PepT1 in rat small intestine epithelia. Thamotharan M, Bawani S, Zhou X, Adibi S. Functional and molecular expression of intestinal oligopeptide transporter (PepT1) after a brief fast. *Metabolism* 1999; 48:681–684.

To initiate investigation of potential influence of fasting and glucocorticoids on MDCK cells expression of GlySar uptake capacity, the $H^+$-dependent uptake of GlySar was evaluated over a 72 period of nutrient deprived or fed and cultured with dexamethasone (Dex) and compared to that by cells cultured in DMEM or DMEM that contained insulin (negative control) (Trial 3A). The “nutrient deprived” treatment actually contained 5 mM glucose and appropriate salts to ensure adequate basal metabolic conditions.

Although recruitment of PepT1 protein and activity appears sensitive to insulin-stimulated recruitment from cytosolic vesicles in Caco-2 cells (Thamotharan M, Bawani S, Zhou X, Adibi S. Hormonal regulation of oligopeptide transporter PepT1 after a brief fast. *Am J Physiol* 1999; 276:C821–826, MDCK cells are reported to be insensitive to insulin, likely as an inability to express the insulin receptor. Hofmann C, Crettaz M, Bruns P, Hessel P, Hadawi G. Cellular responses elicited by insulin mimickers in cells lacking detectable plasma membrane insulin receptors. *J Cell Biol* 1985; 27:401–414. In contrast to the lack of insulin sensitivity, IGF-I is known to stimulate DNA synthesis and cell proliferation in MDCK cells. Sukegawa I, Hizuka N, Takano K, Asakawa K, Shizume K. Characterization of IGF-1 receptors on MDCK cell line. *Endocrinol Japan* 1987; 34(3):339–346. Mouzon S H, Kahn R. Insulin-like growth factor-mediated phosphorylation and proto-ontogeny induction in MDCK cells. *Mol Endocrinol* 1991; 5:51–60. The understanding that MDCK cells are apparently insensitive to insulin stimulation yet are sensitive to IGF-I stimulation appears to be a paradox given that the supra-physiologic levels of both substrates employed in the perspective studies and the known ability of insulin to cross react with the IGF-I receptor. Accordingly, another trial (Trial 3B) was conducted to evaluate the influence of increasing IGF-I concentrations on $H^+$-dependent GlySar uptake by MDCK of the same plating stock.

Trial 3A

Cell culture.

MDCK cells were maintained as described in Trial 1, except that cells were cultured for only 1 d before transport trials were performed. Following initial and common culture conditions, cells were cultured in a “nutrient depleted” buffer (Hepes/Tris (pH 7.5),140 mM NaCl, 5.4 mM KCl, 1.8 mM $CaCl_2$, 0.8 mM $MgSO_4$) that contained 5 mM glucose as an energy source, but that lacked amino acid or vitamin sources. In contrast, cells cultured in DMEM, or DMEM that contained 5 nM Dex, 500 nM Dex, 5 nM insulin, or 500 nM insulin, were adequately nourished. Media treatments (n=4) were as follows:

Nutrient Depleted

DHEM

DMEM+5 nM Dex

DMEM+500 nM Dex

DMEM+5 nM Insulin

DMM+500 nM Insulin

Uptake measurements.

The measurement of [$^3$H]Glysarcosine uptake was performed by using the 24-well cluster tray method as previously described in the Methods section of Trial 1. Peptide uptake is reported as pmol* $mg^{-1}$ protein*30 $min^{-1}$. Uptake measurements were taken after 30 min and 4 h of culture in treatment media.

Trial 3B

Trial 3B was conducted in the same manner as described for Trail 3A, except that cells were cultured in DMEM or DMEM that contained 1 nM IGF-1, 5 nM IGF-1, 25 nM IGF-1, or 100 nM IGF-1. Uptake measurements were taken after 30 min and 4 h of culture time. Media treatments (n=4) were as follows:

DMEM (pH 6 measurement)

DMEM (pH 7.5 measurement)

DMEM+1 nM IGF-1

DMEM+5 nM IGF-1

DMEM+25 nM IGF-1

DMEM+100 nM IGF-1

Results.

Figure 23:
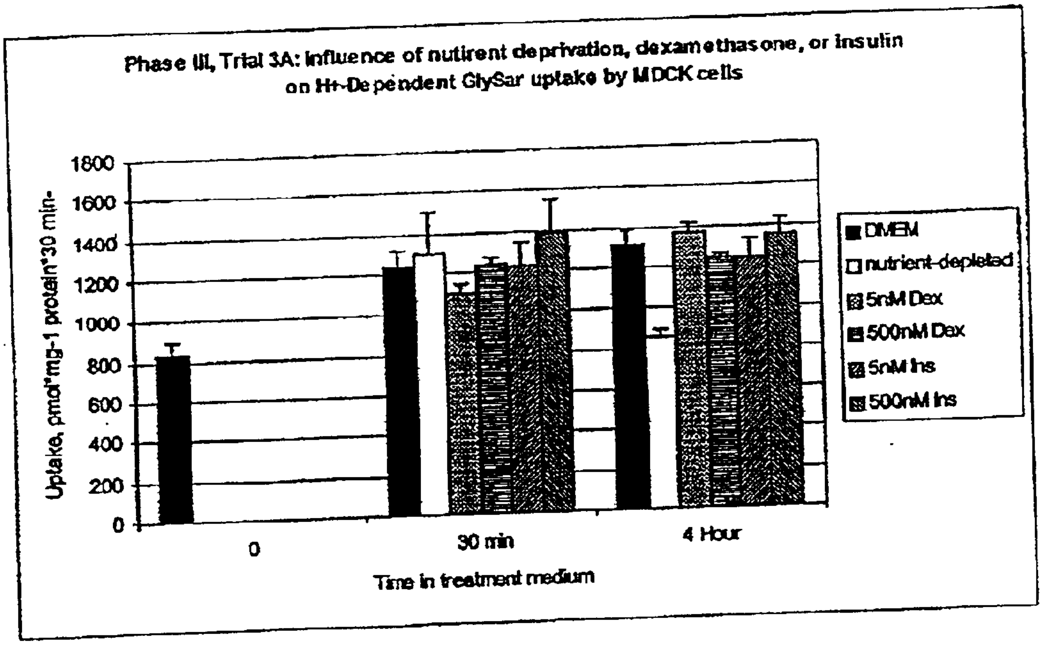
FIG. 23 is a graph illustrating the influence of DMEM, nutrient depleted, dexamethasone (Dex), or insulin (ins) on $H^+$-dependent uptake of [$^3$H]Glycylsarcosine (GlySar) by MDCK cells.
Figure 24:
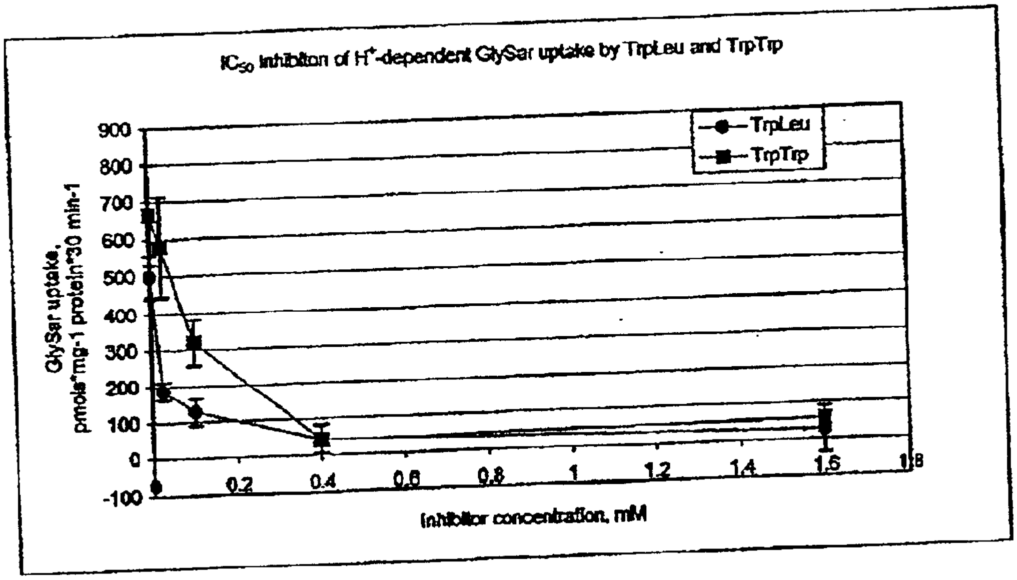
FIG. 24 is a graph illustrating influence of IGF-I on $H^+$-dependent uptake of [$^3$H]Glycylsarcosine (GlySar) by MDCK cells.

Protein content of the treatments within Trails 3A or 3B did not differ. After 4 h of culture, however, the capacity for $H^+$-dependent peptide uptake was reduced 35% in cells deprived of nutrients but adequate in energy (FIG. 23). In contrast, dexamethasone had no effect on GlySar uptake. As expected, and consistent with the concept that MDCK cells are insulin-insensitive, the presence of insulin for 4 h had no effect on GlySar uptake capacity. Similarly, culture of cells with increasing amounts of IGF-I elicited no significant stimulation of $H^+$-dependent GlySar uptake (FIG. 24). Quantitatively, however, 1 to 25 nM of IGF-I tended to increase GlySar uptake capacity by 10 to 15%.

Given the noted restrictions of Trail 3, and the low number of observations (n=4) results from trial 3A and 3B suggest that $H^+$-dependent uptake of GlySar by MDCK is sensitive to nutrient deprivation and, perhaps, IGF-I.

EXAMPLE 4

PepT1 Sequence

Clone12 ($5^{th}$ Round; SEQ ID NO:11) Primer Pair is GSP3-4; GSP3-1R Using Regular RT-PCR catcttcttcatcgtggtcaatgagttctgtgaaaga ttttcctactatggaatgagagcactc-ctgattctgtacttcagacg gttcatcgggtgggacgataatctgtccacgg ccatctaccacacgtttgtggctctgt-gctacctgacgccgatcctcgg cgcactgatcgcagactcctggctgggaaagttcaa gacaatcgtgtcactctccattgtcta-cacaattggacaggcggt cactgcagtaagctcaattaatgacctcacagactat aacaaagatggaactcctgacaatct-gtccgtgcatgtggcact gtccatgattggcctggccctgatagctctgggaa ctggaggaataaagccctgtgtgtctg-catttggtggagaccagtt tgaagagggccaggaaaaacaaagaaacagattc ttttccatcttttatttggccattaat-gctggaagcttgatttccactat tgtcactcccatgctcagagttcacgaatgt ggaatttacagtcagaaagcttgttac-ccactggcatttggggttcctgctg ctctcatggccgtatctctgattgtatt tgtcattggcagtggaatgtacaagaagttt cagc-cccagggtaatgtcatgggt aaagttgtcaagtgcattggttttgccct caaaaataggtttaggcaccggagtaag-cagtttcccaagagggagcactgg ctggactgggctaaagagaaatac gatgagcggctcatctctcaaattaa-gatggtcacaaaagtgatgttcttgtacatcc cactcccaatgttctgggccctgtttgacc agcagggctccaggtggacactgcaag-caacagctatgagtgggaaaatt ggacttcttgaagttcagccagatcagat gcagactgtgaatgccatcttgat-tgtcgtcatggtccccatcatggatgccg tggtgtaccctctgattgcaaaatgt ggcttcaatttcacctccttgaagag-gatgacagttggaatgttcctggcttccatgg ccttcgtgatggcggcgattgttcagctgg aaattgataaaactcttccagtcttcccc aaa-caaaatgaagtccaaatcaa agtactgaatataggaaatggtgccat gaatgtatcttttcctggagcggtggtgacag ttagc-caaatgagtcaatcagat ggatttatgacttttgatgtagacaaac tgacaagtataaacatttcttccactg-gatcaccagtcattccagtgacttataact ttgagcagggccatcgccatacccttctagtatgggcccccaataattac-cgagtggtaaaggatggccttaaccagaa gccagaaaaagggag Amplification Conditions

| | Initiale Denaturat | Denatur-ation | An-nealing | Amplifi-cation | Extension | Cooling |
|---|---|---|---|---|---|---|
| Temp | 94° C. | 94° C. | 55° C. | 72° C. | 72° C. | 4° C. |
| Min. | 10 min | 2 min | 1.5 min | 2 min | 10 min | inf. |
| Cycle | 1 | | 35 | | 1 | |

Clone37 Beginning (6$^{th}$ Round; SEQ ID NO:12) Primer Pair Is GSP3-9; AUAP Using 3'RACE Protocol gccatcgccatacccttctagtatgggccccc aataattaccgagtggtaaag-gatggcc ttaaccagaagccagaaaa aggagaaaatggaatcagatttataaat-agtctt aatgagagcctcaacatcaccatgggcgacaaagtttatgtgaatgtc accagtcacaatgccagcgagtatcagttctttt ctttgggcacaaaaaacatta-caataagttcaacacaacagatctcac aaaattgtacaaaagttctccaatcatc-caaccttgaa tttggtagtgcatatacctatgtaatcggaacgcagagcactggc tgccctgaatgcatatgtttgaagatattcaccc aacacagttaacatggctctgca-gatcccgcagtacttcctcatcacc tgcggcgaggtggttttctctgtcacaggact ggagttctcatattctcaggccccctccaacatgaagtcggtgcttcagg cgg-gatggctgctgacagtggcttgttggcaa catcattgtgctcattgtggcaggag-caggccagttcagtgaacagtg ggctgaatacatcctatttgcggcattgctt ctg-gttgtctgtgtaatatttgccat catggccccggttttacacttacgtcaatc cagcagagattg Amplification Conditions

| | Initiale Denaturat | Denatur-ation | An-nealing | Amplifi-cation | Extension | Cooling |
|---|---|---|---|---|---|---|
| Temp | 94° C. | 94° C. | 52° C. | 72° C. | 72° C. | 4° C. |
| Min. | 10 | 2 min | 1.5 min | 2 | 10 | inf. |
| Cycle | 1 | | 30 | | 1 | |

Merge Sequence (SEQ ID NO:8) Is catcttcttcatcgtggtcaatgagttgt gaaagattttcctactatggaatgagagca ctcctgattctgtacttcagacgg ttcatcgggtgggacgataatctgtccacgg rcatctaccacacgtttgtggctctgt gctacctgacgccgatcctcggc gcact-gatcgcagactcctggctgggaaag ttcaagacaatcgtgtcactctccat-tgtctacacaattggacaggcggtc actgcagtaagctcaattaatgacctc aca-gactataacaaagatggaactcc tgacaatctgtccgtgcatgtggcactgt ccatgattggcctggccctgatagctct gggaactggaggaataaagccctgtg tgtctgcatttgtggagaccagtttg aagagggccaggaaaaacaaagaaacag attcttttccatcttttantggccatt aatgctggaagcttgatttccactattg tcactc-ccatgctcagagttcacgaatgt ggaatttacagtcagaaagcttgtta cccactg-gcatttggggttcctgctgct ctcatggccgtatctctgattgtatttgtca ttg-gcagtggaatgtacaagaagtttcag ccccagggtaatgtcatgggtaa agttgtcaagtgcattggttttgccctc aaaaataggtttaggcaccggagt aag-cagtttcccaagagggagcactggct ggactgggctaaagagaaatacgatgag cggctcatctctcaaattaagatggtcac aaaagtgatgttcttgtacatccc actc-ccaatgttctgggccctgtttgacc agcagggctccaggtggacactgcaagc aacagctatgagtgggaaaattg gacttcttgaagttcagccagatcagat gca-gactgtgaatgccatcttgattgtc gtcatggtccccatcatggatgccgt ggtg-taccctctgattgcaaaatgtggc ttcaatttcacctccttgaagaggatg acagt-tggaatgttcctggcttccatgg ccttcgtgatggcggcgattgttcagct ggaaattgataaaactcttccagtctt ccccaaacaaaatgaagtccaaatcaa agtactgaatataggaaatggtgccatg aatgtatcttttcctggagcggtggtg acagttagccaaatgagtcaatcagat ggatttatgacttttgatgtagacaaac tgacaagtataaacatttcttccact ggatcaccagtcattccagtgacttataact ttgagcagggccatcgccatacccftctag tatgggcccccaataattaccgag tggtaaaggatggccttaaccagaa gccagaaaaaggagaaaatggaatcaga tttataaatagtcttaatgagag cctcaacatcaccatgggcgacaaagttt atgt-gaatgtcaccagtcacaatgcc agcgagtatcagttcttttcttt gggca-caaaaaacattacaataagttcaacacaa cagatctcacaaaattgtacaaaagt-tct ccaatcatccaaccttgaatttgg tagtgcatatacctatgtaatcggaacgca gagcactggctgccctgaattgcatat gtttgaagatatttcacccaacacag ttaa-catggctctgcagatcccgcagtac ttcctcatcacctgcggcgaggtggttttct ctgtcacaggactggagttctcatattct caggccccctccaacatgaagtc ggt-gcttcaggcgggatggctgctgacagtggct tgttggcaacatcattgtgctcattgtggcaggagcaggccagtt cagtgaaacagtgggctgaatacatcctatttgcggcattgcttct ggttgtctgtgtaatatttgccatcatggccccggtttt acacttacgtcaatccagcagagattg Multiple Alignment of Nucleotide Full Length Sequences

```
Sequence 1: XM_007063Homosapiens      3045 bp

Sequence 2: AY027496Ovis              2829 bp

Sequence 3: D50306Rat                 2900 bp

Sequence 4: NM_053079Musmusculus      3128 bp

Sequence 5: U13707Oryctolaguscunic    2709 bp

Sequence 6: AY029615Gallusgallus      2914 bp

Sequence 7: SequencetosubmitGenbak    1840 bp

Start of Pairwise alignments

Aligning . . .

Sequences (4:5) Aligned. Score: 65

Sequences (1:2) Aligned. Score: 65

Sequences (2:3) Aligned. Score: 66
```

-continued

Sequences (3:4) Aligned. Score: 88

Sequences (4:6) Aligned. Score: 48

Sequences (2:4) Aligned. Score: 64

Sequences (1:3) Aligned. Score: 67

Sequences (3:5) Aligned. Score: 66

Sequences (4:7) Aligned. Score: 80

Sequences (2:5) Aligned. Score: 77

Sequences (3:6) Aligned. Score: 48

Sequences (5:6) Aligned. Score: 51

Sequences (1:4) Aligned. Score: 76

Sequences (3:7) Aligned. Score: 81

Sequences (5:7) Aligned. Score: 79

Sequences (2:6) Aligned. Score: 50

Sequences (6:7) Aligned. Score: 70

Sequences (1:5) Aligned. Score: 67

Sequences (2:7) Aligned. Score: 83

Sequences (1:6) Aligned. Score: 49

Sequences (1:7) Aligned. Score: 85

Guide tree file created:

[/net/nfs0/vol1/production/w3nobody/tmp/999267.834538-239427.dnd]

Start of Multiple Alignment

There are 6 groups

Aligning . . .

Group 1: Sequences: 2 Score: 48218

Group 2: Sequences: 3 Score: 43200

Group 3: Sequences: 2 Score: 42027

Group 4: Sequences: 5 Score: 39817

Group 5: Sequences: 6 Score: 30418

Group 6: Sequences: 7 Score: 33857

Alignment Score 249395

CLUSTAL-Alignment file created

[/net/nfs0/vol1/production/w3nobody/tmp/999267.834538-239427.aln]

Your Multiple Sequence Alignment:

999267.834538-239427.aln

CLUSTAL W (1.81) multiple sequence alignment

```
D50306Rat               -----------------------------------CTGAACTCCTGCTTG    15 (SEQ ID NO:3)
NM_053079Musmusculus    --------------------------------------------------       (SEQ ID NO:4)
XM_007063Homosapiens    --------------------------------------------------       (SEQ ID NO:1)
AY027496Ovis            -----GAAACAACATCTTTAGCACGGATTCCTCCCACCTGGACTCCTCGC    45 (SEQ ID NO:2)
U13707Oryctolaguscunic  --------------------------------------------------       (SEQ ID NO:5)
```

-continued

```
SequencetosubmitGenbak      --------------------------------------------------        (SEQ ID NO:7)

AY029615Gallusgallus        GCTCTCTGTCCGTCCCTCGGTCCCTCCGTCCCTCCGTCCCCGCGCGGCCG    50  (SEQ ID NO:6)

D50306Rat                   CCAGTCGCCGGTCAGGAGCCTCGGAGCCGCCACAATGGGGATGTCCAAGT    65
NM_053079Musmusculus        ---GTCGCCCGTCCGGAGCCTTGGAGCCACCACAATGGGGATGTCCAAGT    47
XM_007063Homosapiens        ---------------------------------------GAATGTCCAAAT    12
AY027496Ovis                TCGCCAGTCGCAGGGAGCCCTCGGAGCCGCCAGCATGGGAATGTCCGTGC    95
U13707Oryctolaguscunic      -------------------------------CACCATGGGAATGTCTAAGT    20
SequencetosubmitGenbak      --------------------------------------------------
AY029615Gallusgallus        CCAGCAGCGTGCCGGCCCCATGGCTGCAAAAAGTAAGAGTAAGGGCCGAT    100

D50306Rat                   CT---CGGGGTTGCTTTGGCTACCCATTGAGCATCTTCTTCATCGTGGTC    112
NM_053079Musmusculus        CT---CGGGGTTGCTTCGGTTACCCGTTGAGCATCTTCTTCATCGTGGTC    94
XM_007063Homosapiens        CA---CACAGTTTCTTTGGTTATCCCCTGAGCATCTTCTTCATCGTGGTC    59
AY027496Ovis                CG---AAGAGCTGCTTCGGTTACCCCTTAAGCATCTTCTTCATCGTGGTC    142
U13707Oryctolaguscunic      CA---CTGAGCTGCTTCGGCTATCCCCTGAGCATCTTCTTCATCGTGGTC    67
SequencetosubmitGenbak      -------------------------------CATCTTCTTCATCGTGGTC    19
AY029615Gallusgallus        CAGTGCCGAACTGCTTTGGCTACCCCTTGAGCATCTTCTTCATCGTCATC    150
                                                           ***************  **

D50306Rat                   AATGAATTCTGTGAAAGATTCTCCTACTATGGGATGCGAGCTCTCCTGGT    162
NM_053079Musmusculus        AATGAATTCTGTGAAAGATTCTCCTACTATGGCATGCGAGCACTCCTGGT    144
XM_007063Homosapiens        AATGAGTTTTGCGAAAGATTTTCCTACTATGGAATGCGAGCAATCCTGAT    109
AY027496Ovis                AATGAGTTCTGCGAAAGGTTCTCTTACTATGGAATGAGAGCACTCCTGAT    192
U13707Oryctolaguscunic      AATGAGTTCTGCGAAAGGTTCTCCTACTATGGGATGAGAGCACTCCTGAT    117
SequencetosubmitGenbak      AATGAGTTCTGTGAAAGATTTCCTACTATGGAATGCGAGCAATCCTGAT    69
AY029615Gallusgallus        AATGAGTTCTGCGAGAGGTTCTCCTACTATGGCATGCGAGCAATGCTCGT    200
                            ***** ** ** ** ** ** ** ******** *** ****  * **  *

D50306Rat                   TCTGTACTTCAGGAACTTCCTTGGCTGGGATGATGACCTCTCCACGGCCA    212
NM_053079Musmusculus        TCTGTACTTCAGGAACTTCCTCGGCTGGGACGACAATCTCTCCACGGCCA    194
XM_007063Homosapiens        TCTGTACTTCACAAATTTCATCAGCTGGGATGATAACCTGTCCACCGCCA    159
AY027496Ovis                CCTGTACTTCCAACGTTTCCTGGGCTGGAACGACAACCTGGGCACCGCCA    242
U13707Oryctolaguscunic      TCTGTACTTCAGAAACTTCATCGGCTGGGACGACAACCTGTCCACGGTCA    167
SequencetosubmitGenbak      TCTGTACTTCAGACGGTTCATCGGGTGGGACGATAATCTGTCCACGGCCA    119
AY029615Gallusgallus        ATTGTATTTCAAGTACTTCCTGCGGTGGGATGACAACTTTTCTACAGCCA    250
                              **** ***      *** *  * *** * **  *  *    ** * **

D50306Rat                   TCTACCATACGTTTGTTGCCCTCTGCTACCTGACTCCAATTCTTGGAGCT    262
NM_053079Musmusculus        TTTACCATACGTTCGTTGCCCTCTGCTACCTGACTCCAATTCTTGGAGCT    244
XM_007063Homosapiens        TCTACCATACGTTTGTGGCTCTGTGCTACCTGACGCCAATTCTCGGAGCT    209
AY027496Ovis                TCTATCACACGTTCGTCGCCCTGTGCTACCTGACGCCCATCCTCGGAGCT    292
U13707Oryctolaguscunic      TCTACCACACGTTCGTCGCGCTGTGCTACCTCACGCCCATTCTCGGAGCT    217
SequencetosubmitGenbak      TCTACCACACGTTTGTGGCTCTGTGCTACCTGACGCCGATCCTCGGCGCA    169
AY029615Gallusgallus        TCTACCACACGTTTGTTGCTCTGTGCTACTTGACGCCCATCCTGGGAGCG    300
                            * ** ** ***** ** ** ** ****** * ** ** ** ** ** **

D50306Rat                   CTGATCGCAGACTCGTGGCTGGGGAAGTTCAAGACAATTGTCTCACTATC    312
NM_053079Musmusculus        CTGATCGCAGACTCGTGGCTGGGGAAGTTCAAGACAATTGTTTCACTATC    294
XM_007063Homosapiens        CTTATCGCCGACTCGTGGCTGGGAAAGTTCAAGACCATTGTGTCGCTCTC    259
AY027496Ovis                CTCATCGCCGACTCCTGGCTGGGGAAGTTCAAGACGATCGTGTCGCTGTC    342
U13707Oryctolaguscunic      CTCATCGCCGACGCGTGGCTGGGGAAGTTCAAGACCATCGTGTGGCTGTC    267
SequencetosubmitGenbak      CTGATCGCAGACTCCTGGCTGGGAAAGTTCAAGACAATCGTGTCACTCTC    219
AY029615Gallusgallus        CTCATTGCAGACTCATGGCTGGGAAAGTTTAAGACCATTGTCTCCCTGTC    350
                            ** ** ** *** * ******** ***** ***** ** ** *  ** **

D50306Rat                   CATCGTCTACACGATCGGACAGGCCGTCATCTCAGTGAGCTCAATTAATG    362
NM_053079Musmusculus        CATCGTCTACACGATTGGACAAGCAGTCATCTCGGTGAGCTCAATTAATG    344
XM_007063Homosapiens        CATTGTCTACACAATTGGACAAGCAGTCACCTCAGTAAGCTCCATTAATG    309
AY027496Ovis                CATCGTCTACACCATTGGGCAGGTAGTCATCGCTGTGAGCTCAATTAATG    392
U13707Oryctolaguscunic      CATCGTCTACACCATCGGACAAGCAGTCACCTCCCTCAGCTCCGTCAATG    317
SequencetosubmitGenbak      CATTGTCTACACAATTGGACAGGCGGTCACTGCAGTAAGCTCAATTAATG    269
AY029615Gallusgallus        CATTGTCTATACAATTGGGCAGGCAGTCATGGCTGTAAGCTCCATAAACG    400
                            *** ***** ** ** ** ** *  ****   *  * *****  * ** *

D50306Rat                   ACCTTACAGACCATGACCACGACGGCAGTCCTAACAACCTTCCTTTGCAC    412
NM_053079Musmusculus        ACCTCACAGACCACGACCACAATGGCAGTCCTGACAGCCTTCCCGTGCAC    394
XM_007063Homosapiens        ACCTCACAGACCACAACCATGATGGCACCCCCGACAGCCTTCCTGTGCAC    359
AY027496Ovis                ACCTCACTGACTTCAACCATGATGGAACCCCAAACAATATTTCTGTGCAC    442
U13707Oryctolaguscunic      AGCTCACAGACAACAACCATGACGGGACCCCCGACAGCCTCCCTGTGCAC    367
SequencetosubmitGenbak      ACCTCACAGACTATAACAAAGATGGAACTCCTGACAATCTGTCCGTGCAT    319
AY029615Gallusgallus        ACATGACAGATCAAAACAGAGATGGCAATCCTGATAATATTGCGGTGCAC    450
                            *  * ** **     **    * ** *  **  * *   *  *  ****

D50306Rat                   GTAGCACTGTCCATGATCGGCCTGGCCCTGATAGCCCTTGGTACAGGAGG    462
NM_053079Musmusculus        GTAGCACTGTCCATGGTTGGCCTGGCCCTGATAGCCCTTGGTACAGGAGG    444
XM_007063Homosapiens        GTGGTGCTGTCCTTGATCGGCCTGGCCCTGATAGCTCTCGGGACTGGAGG    409
AY0274696Ovis               GTGGCACTCTCCATGATTGGCCTGGTCCTGATAGCTCTGGGTACCGGAGG    492
U13707Oryctolaguscunic      GTGGCGGTGTGCATGATCGGCCTGCTCCTGATAGCCCTCGGGACAGGAGG    417
```

-continued

```
SequencetosubmitGenbak        GTGGCACTGTCCATGATTGGCCTGGCCCTGATAGCTCTGGGAACTGGAGG    369
AY029615Gallusgallus          ATTGCCCTGTCTATGACTGGCTTGATTCTCATCGCGCTTGGAACTGGTGG    500
                               * *   * *   **   *** **   ** ** ** ** ** ** ** **

D50306Rat                     AATCAAGCCCTGTGTGTCTGCATTTGGTGGCGATCAGTTTGAAGAGGGTC    512
NM_053079Musmusculus          AATCAAGCCCTGTGTGTCTGCGTTTGGTGGCGATCAGTTTGAAGAGGGTC    494
XM_007063Homosapiens          AATCAAACCCTGTGTGTCTGCGTTTGGTGGAGATCAGTTTGAAGAGGGCC    459
AY027496Ovis                  GATAAAGCCTTGCGTGTCTGCATTTGGCGGAGATCAGTTTGAAGAGGGCC    542
U13707Oryctolaguscunic        AATCAAGCCCTGTGTGTCTGCCTTTGGCGGCGATCAGTTTGAGGAGGGCC    467
SequencetosubmitGenbak        AATAAAGCCCTGTGTGTCTGCATTTGGTGGAGACCAGTTTGAAGAGGGCC    419
AY029615Gallusgallus          GATCAAACCTTGTGTCTCAGCATTTGGTGGGGATCAGTTTGAAGAACATC    550
                               ** ** ** ** ** ** ** ***** ** ** ******** **     *

D50306Rat                     AGGAAAAACAGCGAAACCGGTTCTTTTCCATCTTTTATTTGGCTATCAAC    562
NM_053079Musmusculus          AGGAAAAACAGCGAAACCGGTTCTTTTCCATCTTTTATTTGGCTATCAAC    544
XM_007063Homosapiens          AGGAGAAACAAAGAAACAGATTTTTTTCCATCTTTTACTTGGCTATTAAT    509
AY027496Ovis                  AGGAAAAGCAAAGGAACAGATTTTTTTCCATCTTTTATTTGGCCATTAAT    592
U13707Oryctolaguscunic        AGGAAAAGCAAAGAAACCGGTTTTTTTCCATCTTTTACTTGGCCATTAAC    517
SequencetosubmitGenbak        AGGAAAAACAAAGAAACAGATTCTTTTCCATCTTTTATTTGGCCATTAAT    469
AY029615Gallusgallus          AGGAAAAACAAAGAAGTAGATTCTTCTCTATCTTTTATTTGTCCATTAAT    600
                              **** ** **  * *   * ** ** ** ******** *** * ** **

D50306Rat                     GCAGGAAGCCTGCTCTCCACGATCATCACTCCCATACTCAGAGTTCAGCA    612
NM_053079Musmusculus          GGGGGAAGCCTGCTCTCCACGATCATCACTCCCATACTCAGAGTTCAACA    594
XM_007063Homosapiens          GCTGGAAGTTTGCTTTCCACAATCATCACACCCATGCTCAGAGTTCAACA    559
AY027496Ovis                  GCTGGAAGTTTGCTTTCTACTATCATCACCCCCATGCTCAGAGTTCAGGT    642
U13707Oryctolaguscunic        GCTGGGAGTCTGCTGTCCACAATCATCACCCCCATGGTCAGAGTTCAACA    567
SequencetosubmitGenbak        GCTGGAAGCTTGATTTCCACTATTGTCACTCCCATGCTCAGAGTTCACGA    519
AY029615Gallusgallus          GCTGGAAGTCTCATATCCACTATAATCACCCCAATTCTCAGAGCTCAAGA    650
                              *  ** **  *  * ** ** **  **** ** **  ****** ***

D50306Rat                     GTGCGGAATCCACAGCCAACAAGCTTGTTACCCACTGGCCTTTGGGGTTC    662
NM_053079Musmusculus          GTGCGGAATCCACAGTCAACAAGCTTGTTACCCACTGGCCTTCGGGGTTC    644
XM_007063Homosapiens          ATGTGGAATTCACAGTAAACAAGCTTGTTACCCACTGGCCTTTGGGGTTC    609
AY027496Ovis                  ATGCGGAATTCACAGTAAGCAAGCTTGTTACCCCCTGGCCTTTGGGGTTC    692
U13707Oryctolaguscunic        ATGTGGAATTCACGTTAAACAAGCTTGCTACCCACTGGCCTTTGGGATTC    617
SequencetosubmitGenbak        ATGTGGAATTTACAGTCAGAAAGCTTGTTACCCACTGGCATTTGGGGTTC    569
AY029615Gallusgallus          ATGTGGCATTCACAGCAGACAGCAGTGCTACCCGCTGGCATTTGGAGTTC    700
                               ** ** **  **       *     ** ***** ***** ** **  ***

D50306Rat                     CGGCAGCTCTCATGGCTGTTGCCCTAATTGTGTTTGTCCTCGGCAGTGGA    712
NM_053079Musmusculus          CAGCGGCTCTCATGGCTGTTGCCCTAATTGTGTTTGTCCTTGGCAGTGGA    694
XM_007063Homosapiens          CTGCTGCTCTCATGGCTGTAGCCCTGATTGTGTTTGTCCTTGGCAGTGGG    659
AY027496Ovis                  CTGCTGCACTCATGGCTGTATCTCTGATCGTGTTTGTCATTGGCAGTGGA    742
U13707Oryctolaguscunic        CTGCTATCCTCATGGCTGTATCCCTGATCGTGTTCATCATCGGCAGTGGG    667
SequencetosubmitGenbak        CTGCTGCTCTCATGGCCGTATCTCTGATTGTATTTGTCATTGGCAGTGGA    619
AY029615Gallusgallus          CCGCTGCCCTCATGGCTGTTTCATTAGTTGTGTTCATAGCTGGAAGTGGA    750
                              * **     ******** **  *  *  * ** **  *     ** *****

D50306Rat                     ATGTACAAGAAGTTTCAGCCCCAGGGCAACATCATGGGCAAAGTGGCCAA    762
NM_053079Musmusculus          ATGTACAAGAAGTTCCAGCCCCAGGGCAACATCATGGGCAAAGTGGCCAA    744
XM_007063Homosapiens          ATGTACAAGAAGTTCAAGCCACAGGGCAACATCATGGGTAAAGTGGCCAA    709
AY027496Ovis                  ATGTACAAGAAGGTCCAGCCCCAGGGTAACATCATGTCTAAAGTTGCCAG    792
U13707Oryctolaguscunic        ATGTACAAGAAGTTCAAGCCGCAGGGGAACATCCTGAGCAAAGTGGTGAA    717
SequencetosubmitGenbak        ATGTACAAGAAGTTTCAGCCCCAGGGTAATGTCATGGGTAAAGTTGTCAA    669
AY029615Gallusgallus          ATGTACAAAAAAAGTTCAACCGCAAGGCAATATAATGGTTCGAGTTTGTAA    800
                              ******** **  *  * ** ** ** **  *  **      ***    *

D50306Rat                     GTGCATTGGCTTTGCCATCAAAAACAGGTTTCGGCACCGAAGTAAGGCAT    812
NM_053079Musmusculus          GTGCATTGGTTTTGCCATCAAAAACAGGTTTCGGCACCGAAGTAAGGCAT    794
XM_007063Homosapiens          GTGCATCGGTTTTGCCATCAAAAATAGATTTAGGCATCGGAGTAAGGCAT    759
AY027496Ovis                  GTGCATTGGGTTTGCCATCAAAAATAGGATTAGCCATCGGAGTAAGAAAT    842
U13707Oryctolaguscunic        GTGCATCTGCTTTGCCATCAAAAATAGGTTTAGGCACCGCAGTAAGCAGT    767
SequencetosubmitGenbak        GTGCATTGGTTTTGCCCTCAAAAATAGGTTTAGGCACCGGAGTAAGCAGT    719
AY029615Gallusgallus          ATGCATTGGATTTGCCATTAAAAACAGGTTTCGGCATCGCAGCAAAGAGT    850
                               *****  * ****** * ***** **  ** * ** ** ** **     *

D50306Rat                     TTCCCAAGAGGGAACACTGGCTGGACTGGGCTAAAGAGAAATACGATGAG    862
NM_053079Musmusculus          ATCCCAAGAGGGAGCACTGGCTGGACTGGGCTAAAGAGAAATACGACGAG    844
XM_007063Homosapiens          TTCCCAAGAGGGAGCACTGGCTGGACTGGGCTAAAGAGAAATACGATGAG    809
AY027496Ovis                  TTCCTAAGAGGGAGCACTGGCTGGACTGGGCTAGCGAGAAATATGATGAG    892
U13707Oryctolaguscunic        TTCCCAAGAGGGCGCACTGGCTGGACTGGGCTAAGGAGAAATACGACGAG    817
SequencetosubmitGenbak        TTCCCAAGAGGGAGCACTGGCTGGACTGGGCTAAAGAGAAATACGATGAG    769
AY029615Gallusgallus          ATCCCAAAAGAGAGCACTGGCTAGACTGGGCAAGCGAGAAGTATGATAAA    900
                               *** ** ** *  ******** ******** *  ***** ** **  *

D50306Rat                     AGGCTCATCTCGCAGATTAAGATGGTGACGAAGGTGATGTTCCTGTACAT    912
NM_053079Musmusculus          CGGCTCATCTCACAGATTAAGATGGTCACGAAGGTGATGTTCCTGTTCAT    894
XM_007063Homosapiens          CGGCTCATCTCCCAAATTAAGATGGTTACGAGGGTGATGTTCCTGTATAT    859
AY027496Ovis                  CGGCTCATCTCTCAAATTAAGATGGTTACAAGGGTGATGTTCCTGTACAT    942
```

-continued

```
U13707Oryctolaguscunic        CGGCTTATCGCGCAGATCAAGATGGTTACGAGGGTGCTGTTCCTGTACAT      867
SequencetosubmitGenbak        CGGCTCATCTCTCAAATTAAGATGGTCACAAAAGTGATGTTCTTGTACAT      819
AY029615Gallusgallus          CGACTGATTGCTCAGACCAAGATGGTGTTGAAGGTGCTTTTCCTTTACAT      950
                               * ** **  * ** *  ********    *  *** * *** * *  **

D50306Rat                     TCCCCTCCCCATGTTTTGGGCCTTGTTTGACCAGCAGGGTTCCAGGTGGA      962
NM_053079Musmusculus          CCCACTCCCCATGTTCTGGGGCCTGTTTGACCAACAAGGGTCCAGATGGA      944
XM_007063Homosapiens          TCCACTCCCAATGTTCTGGGCCTTGTTTGACCAGCAGGGCTCCAGGTGGA      909
AY027496Ovis                  TCCTCTCCCCATGTTCTGGGCCTTGTTTGATCAGCAGGGCTCCAGGTGGA      992
U13707Oryctolaguscunic        CCCACTCCCCATGTTCTGGGCCTTGTTTGATCAGCAGGGTTCCAGATGGA      917
SequencetosubmitGenbak        CCCACTCCCAATGTTCTGGGCCCTGTTTGACCAGCAGGGCTCCAGGTGGA      869
AY029615Gallusgallus          CCCTCTCCCGATGTTCTGGGCACTTTTTGACCAGCAGGGATCGAGATGGA     1000
                               ** ***** ***** ****   * ***** ** ** ** ** ** ****

D50306Rat                     CACTGCAAGCAACGACCATGACTGGGAAAATTGGAACAATTGAGATTCAG     1012
NM_053079Musmusculus          CACTGCAAGCAACGACCATGAATGGGAAAATTGGAGCAAATGAAATTCAG      994
XM_007063Homosapiens          CACTGCAGGCAACAACTATGTCCGGGAAAATCGGAGCTCTTGAAATTCAG      959
AY027496Ovis                  CACTGCAAGCAACGACCATGAGTGGGAAGATTGGAATCATTGAAATCCAG     1042
U13707Oryctolaguscunic        CGCTGCAAGCGACGACCATGTCCGGGAGAATTGGAATCCTTGAAATTCAG      967
SequencetosubmitGenbak        CACTGCAAGCAACAGCTATGAGTGGGAAAATTGGACTTCTTGAAGTTCAG      919
AY029615Gallusgallus          CACTGCAAGCCACAACTATGGATGGGGACTTTGGAGCTATGCAGATTCAG     1050
                              * ***** ** **  * ***   ***    * ***        *  * ***

D50306Rat                     CCGGACCAGATGCAGACGGTGAACGCCATCTTGATTGTCATCATGGTCCC     1062
NM_053079Musmusculus          CCGGACCAGATGCAGACGGTGAATGCCATCCTGAATGTCAACAATGGCCC     1044
XM_007063Homosapiens          CCCGATCAGATGCAGACCGTGAACGCCATCCTGATCGTGATCATGGTCCC     1009
AY027496Ovis                  CCGGATCAGATGCAGACGGTGAACGCCATCCTGATCGTCGTCATGGTCCC     1092
U13707Oryctolaguscunic        CCGGATCAGATGCAGACTGTGAACACCATCTTGATTATTATCCTGGTCCC     1017
SequencetosubmitGenbak        CCAGATCAGATGCAGACTGTGAATGCCATCTTGATTGTCGTCATGGTCCC      969
AY029615Gallusgallus          CCAGACCAAATGCAGACTGTCAATCCAATCCTGATTATAATAATGGTCCC     1100
                              ** ** ** ******** ** **  * *** ***   *       * ***

D50306Rat                     CATTGTGGACGCCGTGGTGTATCCGCTCATTGCAAAATGTGGTTTCAACT     1112
NM_053079Musmusculus          CAATGTGGACGCCGTTGTGTACCGCTCAATTGCAAAATGTGGTTTCAACT     1094
XM_007063Homosapiens          GATCTTCGATGCTGTGCTGTACCCTCTCATTGCAAAATGTGGCTTCAATT     1059
AY027496Ovis                  CATCGTGGATGCCGTGGTATATCCTCTGATCGCAAAGTGTGGTTTAAATT     1142
U13707Oryctolaguscunic        CATCATGGACGCCGTGGTGTATCCTCTGATTGCAAAGTGTGGCCTCAACT     1067
SequencetosubmitGenbak        CATCATGGATGCCGTGGTGTACCCTCTGATTGCAAAATGTGGCTTCAATT     1019
AY029615Gallusgallus          AGTTGTAGATGCTGTGATTTATCCTTTAATCCAGAAATGCAAGATCAATT     1150
                                   * ** ** **  * ** *     **    ** **     * ** *

D50306Rat                     TCACCTCCCTGAAGAAGATGACCGTTGGGATGTTCCTGGCATCCATGGCC     1162
NM_053079Musmusculus          TCACATCCCTGAAGAAGATGACTGTTGGGATGTTCCTGGCGTCCATGGCC     1144
XM_007063Homosapiens          TCACCTCCTTGAAGAAGATGGCAGTTGGCATGGTCCTGGCCTCCATGGCC     1109
AY027496Ovis                  TCACCTCCCTGAAGAAGATGACCGTCGGCATGTTTCTGGCCTCCATGGCT     1192
U13707Oryctolaguscunic        TCACCTCTCTGAAGAAGATGACGATTGGGATGTTCCTGGCTTCCATGGCC     1117
SequencetosubmitGenbak        TCACCTCCTTGAAGAGGATGACAGTTGGAATGTTCCTGGCTTCCATGGCC     1069
AY029615Gallusgallus          TTACGCCCCTGAGGAGGATCACTGTTGGCATGTTCCTTGCTGGTCTGGCT     1200
                              * **  *  *** ** ***  *  * ** *** * ** **     ****

D50306Rat                     TTTGTGGTGGCTGCAATTGTGCAGGTGGAAATCGATAAAACTCTTCCAGT     1212
NM_053079Musmusculus          TTTGTGGTGGCTGCAATTGTGCAGGTGGAAATCGATAAAACTCTTCCAGT     1194
XM_007063Homosapiens          TTTGTGGTGGCTGCCATCGTGCAGGTGGAAATCGATAAAACTCTTCCAGT     1159
AY027496Ovis                  TTCGTGGCAGCTGCCATCGTGCAGGTGGACATTGACAAAACTCTGCCCGT     1242
U13707Oryctolaguscunic        TTCGTGGCAGCTGCAATCCTGCAGGTGGAAATCGATAAAACTCTTCCTGT     1167
SequencetosubmitGenbak        TTCGTGATGGCGGCGATTGTTCAGCTGGAAATTGATAAAACTCTTCCAGT     1119
AY029615Gallusgallus          TTCGTTGCTGCTGCTCTTTTGCAAGTGCAAATAGATAAAACTCTTCCAGT     1250
                              ** **    ** **  *  * **  ** * ** ** ******** ** **

D50306Rat                     CTTCCCCAGCGGAAATCAAGTTCAAATTAAGGTCTTGAACATTGGAAACA     1262
NM_053079Musmusculus          CTTCCCTGGTGGAAATCAAGTCCAAATTAAGGTCTTGAACATCGGAAACA     1244
XM_007063Homosapiens          CTTCCCCAAAGGAAACGAAGTCCAAATTAAAGTTTTGAATATAGGAAACA     1209
AY027496Ovis                  CTTCCCCAAAGGAAATGAAGTCCAAATCAAAGTCCTGAATATAGGAAATA     1292
U13707Oryctolaguscunic        CTTCCCCAAAGCCAATGAAGTCCAAATTAAAGTTCTGAATGTAGGAAGTG     1217
SequencetosubmitGenbak        CTTCCCCAAACAAAATGAAGTCCAAATCAAAGTACTGAATATAGGAAATG     1169
AY029615Gallusgallus          TTTCCCTGCAGCTGGACAGGCCCAAATCAAAATAATAAATCTAGGTGATA     1300
                               *****           * *  ***** **  *  * **  * **

D50306Rat                     ATGACATGGCCGTGTATTTTCCTGGAAAGAATGTGACAGTTGCCCAAATG     1312
NM_053079Musmusculus          ATAACATGACCGTGCATTTTCCTGGAAATAGTGTGACGCTTGCCCAAATG     1294
XM_007063Homosapiens          ATACCATGAATATATCTCTTCCTGGAGAGATGGTGACACTTGGCCCAATG     1259
AY027496Ovis                  ATAGCATGACCGTGTCTTTTCCCGGAACGACAGTGACATGTGACCAGATG     1342
U13707Oryctolaguscunic        AGAACATGATCATCTCTCTTCCTGGGCAGACGGTGACGCTCAACCAGATG     1267
SequencetosubmitGenbak        GTGCCATGAATGTATCTTTTCCTGGAGCGGTGGTGACAGTTAGCCAAATG     1219
AY029615Gallusgallus          GCAATGCGAATGT-TACATTTCTGCCTAATCTTCAGAACGTGACTGTCCT     1349
                                     *    *     ** * *                   *

D50306Rat                     TCTCA---GACAGACACATT-CATGACTTTCGATGTAGACCAGCTGACAA     1358
NM_053079Musmusculus          TCTCA---GACAGACACGTT-CATGACTTTCGATATAGACAAGCTGACAA     1340
XM_007063Homosapiens          TCTCA---AACAAATGCATT-TATGACTTTTGATGTAAACAAACTGACAA     1305
```

-continued

```
AY027496Ovis                    TCTCA---AACAAACGGATT-TCTGACTTTCAACGTAGACAACCT---AA    1385
U13797Oryctolaguscunic          TCTCA---AACGAATGAATT-CATGACTTTCAATGAAGACACACTGACAA    1313
SequencetosubmitGenbak          AGTCA---ATCAGATGGATT-TATGACTTTTGATGTAGACAAACTGACAA    1265
AY029615Gallusgallus            TCCCATGGAGTCAACAGGCTACAGGATGTTTGAGTCTTCCCAGCTAAAAT    1399
                                   **        *     *    **  **  *      *   **   *

D50306Rat                       GCATAAACGTGTCTTCTCCCGG-ATCTCCAGGCGTCACCACGGTAGCTCA    1407
NM_053079Musmusculus            GCATAAACATATCTTCCTCTGG-ATCCCCAGGAGTCACCACAGTAGCTCA    1389
XM_007063Homosapiens            GGATAAACATTTCTTCTCCTGG-ATCACCAG---TCACTGCTGTAACTGA    1351
AY027496Ovis                    GTATAAACATTTCTTCTACTGG-AACACCAG---TCACTCCAGTAACTCA    1431
U13707Oryctolaguscunic          GCATAAACATCACTTCC---GG-ATCACAAG---TCACCATGATCACACC    1356
SequencetosubmitGenbak          GTATAAACATTTCTTCCACTGG-ATCACCAG---TCATTCCAGTGACTTA    1311
AY029615Gallusgallus            CTGTAATGGTAAATTTTGGGAGTGAGAGTAGAAGTGAAAATATCGACTCA    1449
                                   ***   *   **      *       **   * *         *

D50306Rat                       -TGAGTTTGAGCCGGGTCACCGGCACACCCTTCTAGTGTGGGGCCCCAAT    1456
NM_053079Musmusculus            -TGATTTTGAGCAGGGTCACCGGCACAACCTTCTAGTGTGGGAACCCAGT    1438
XM_007063Homosapiens            -CGACTTCAAGCAGGGCCAACGCCACACGCTTCTAGTGTGGGCCCCCAAT    1400
AY027496Ovis                    -TAACTTTGAGTCCGGCCATCGCCATACCCTTCTCGTCTGGGCCCCAAGT    1480
U13707Oryctolaguscunic          -CAGCCTTGAGGCAGGCCAGCGCCACACCCTGCTGGTGTGGGCCCCCAAT    1405
SequencetosubmitGenbak          -TAACTTTGAGCAGGGCCATCGCCATACCCTTCTAGTATGGGCCCCCAAT    1360
AY029615Gallusgallus            ATAAGCAGCAATACGCATACTGTCACCATCAAGAATGCAGCAGCCGGCAT    1499
                                         *    *   *  * **    *         *    *    *

D50306Rat                       CTATACCGTGTGGTAAA-AGACGGTCTTAACCAAAAGCCAGAGAAAGGGG    1505
NM_053079Musmusculus            CAATACCGTGTGGTAAA-AGATGGTCCTAACCAAAAGCCAGAGAAAGGGG    1487
XM_007063Homosapiens            CACTACCAGGTGGTAAA-GGATGGTCTTAACCAGAAGCCAGAAAAAGGGG    1449
AY027496Ovis                    AACTACCAAGTGGTAAA-AGATGGCCTTAACCAGAAGCCAGAAAAAGGGA    1529
U13707Oryctolaguscunic          AACTACCGAGTGGTCAA-TGACGGCCTGACCCAGAAGTCAGACAAAGGAG    1454
SequencetosubmitGenbak          AATTACCGAGTGGTAAA-GGATGGCCTTAACCAGAAGCCAGAAAAAGGAG    1409
AY029615Gallusgallus            TGTTTCTAGCTTGCGGTCTGATAATTTCACATCAAAACCAGAAGAAGGAA    1549
                                   * *    * *      **       *    **  ****  ****

D50306Rat                       AGAACGGAATCAGATTCGTCAGCACCCTTAACGAGATGATCACCATCAAA    1555
NM_053079Musmusculus            AGAACGGAATCAGGTTTGTCAACACCCTTAACGAGATGGTCACCAACAAA    1537
XM_007063Homosapiens            AAAATGGAATCAGATTTGTAAATACTTTTAACGAGCTCATCACCATCACA    1499
AY027496Ovis                    GAAATGGAATCAGATTCGTTAATGCTTTTGGCGAGAGCTTCGGCGTCACA    1579
U13707Oryctolaguscunic          AAAATGGAATCAGGTTTGTGAACACTTACAGCCAGCCCATCAACGTCACG    1504
SequencetosubmitGenbak          AAAATGGAATCAGATTTATAAATAGTCTTAATGAGAGCCTCAACATCACC    1459
AY029615Gallusgallus            AGAATCTAGTCAGGTTTGTAAATAATTTGCCTCAGACAGTCAACATCACT    1599
                                  **   * **** **  * *            **    **  *  **

D50306Rat                       ATGAGTGGAAAAGTGTACGAAAATGTCACCAGTCACAG-CGCCAGCAACT    1604
NM_053079Musmusculus            ATGAGTGGGAAAGTATATGAAAAATTCACAAGTCACAA-CGCCAGCGGCT    1586
XM_007063Homosapiens            ATGAGTGGGAAAGTTTATGCAAACATCAGCAGCTACAA-TGCCAGCACAT    1548
AY027496Ovis                    ATGGATGGGGAAGTTTACAACAATGTCTCCGGTCACAA-TGCCAGTGAAT    1628
U13707Oryctolaguscunic          ATGAGCGGGAAAGTTTACGAACACATCGCCAGCTACAA-TGCCAGCGAGT    1553
SequencetosubmitGenbak          ATGGGCGACAAAGTTTATGTGAATGTCACCAGTCACAA-TGCCAGCGAGT    1508
AY029G15Gallusgallus            ATGGGTGACACGACTTTTG-GAATACTGGAAGAGACAAGTATCAGTAATT    1648
                                ***   *        *      *        *  ***     ***    *

D50306Rat                       ATCAGTTTTTCCCTTCTGGCCAAAAAGACTACACAATAAACACCACAGA-    1653
NM_053079Musmusculus            ACAAGTTCCTCCCTTCTGGCGAAAAGCAGTACACAATAAACACCACGGC-    1635
XM_007063Homosapiens            ACCAGTTTTTTCCTTCTGGCATAAAAGGCTTCACAATAAGCTCAACAGA-    1597
AY027496Ovis                    ATCTTTTTTTCTCTTCTGGCGTAAAGAGCTTCACAATAAACTCACCAGA-    1677
U13707Oryctolaguscunic          ATCAGTTTTCACTTCTGGAGTAAAGGGCTTCACCGTCAGCTCGGCAGG-    1602
SequencetosubmitGenbak          ATCAGTTCTTTTCTTTGGGCACAAAAAACATTACAATAAGTTCAACACAA    1558
AY029615Gallusgallus            ACAGTCCGTTCTCAGGAGGAAGAACATATGATATAGTGATAACTGCAGG-    1697
                                *        *  *    **   **        *   * *   *  *

D50306Rat                       --GATTGCACCAAACTGTTCATCTGATTTTAAATCTTCCAACCTTGACTT    1701
NM_053079Musmusculus            --GGTGGCACCAACCTGTCTAACTGATTTTAAATCTTCCAACCTTGACTT    1683
XM_007063Homosapiens            --GATTCCGCCACAATGTCAACCTAATTTCAATACTTTCTACCTTGAATT    1645
AY027496Ovis                    --GATTTCACAACAGTGTGAAAAACAGTTCAAAACATCCTACCTTGAATT    1725
U13707Oryctolaguscunic          --CATCTCGGAGCAGTGCAGGCGGGACTTTGAGTCTCCGTACCTGGAGTT    1650
SequencetosubmitGenbak          CAGATCTCACAAAATTGTACAAAAGTTCTCCAATCATCCAACCTTGAATT    1608
AY029615Gallusgallus            -----TTCAACTAATTGCAAACC-AACTTCAGAG-----AAATTAGGATA    1736
                                       *       **           *           *  * *  *

D50306Rat                       CGGCAGCGCGTACACCTACGTGATCAGAAGTAGGGCGAGTGATGGCTGCC    1751
NM_053079Musmusculus            TGGCAGCGCGTATACCTACGTGATCCGA---AGGGCGAGTGATGGCTGCC    1730
XM_007063Homosapiens            TGGTAGTGCTTATACCTATATAGTCCAA---AGGAAGAATGACAGCTGCC    1692
AY027496Ovis                    TGGTAGTGCGTTTACCTATGTAATCAGC---AGAAAGAGTGACGGTTGCC    1772
U13707Oryctolaguscunic          TGGCAGCGCGTACACGTACCTGATCACG---AGCCAGGCTACTGGCTGCC    1697
SequencetosubmitGenbak          TGGTAGTGCATATACCTATGTAATCGGA---ACGCAGAGCACTGGCTGCC    1655
AY029615Gallusgallus            TGGTGGTGCTTATACGATCGTAATTAAT---GAGTGTTCTGGAGATGTGA    1783
                                 **  * ** *  **     *  *

D50306Rat                       TGGAAGTGAAGGAATTCGAAGACATCCCACCCAACACGGTGAACATGGCC    1801
NM_053079Musmusculus            TGGAAGTGAAGGAATTTGAAGACATCCCACCCAACACTGTGAACATGGCT    1780
```

-continued

```
XM_007063Homosapiens          CTGAAGTGAAGGTGTTTGAAGATATTTCAGCCAACACAGTTAACATGGCT   1742
AY027496Ovis                  CCGAACCAAAGATTTTCGAAGACATCTCCCCCAACACAGTCAGCATGGCT   1822
U13707Oryctolaguscunic        CCCAAGTGACGGAGTTTGAAGATATTCCGCCCAACACAATGAACATGGCT   1747
SequencetosubmitGenbak        CTGAATTGCATATGTTTGAAGATATTTCACCCAACACAGTTAACATGGCT   1705
AY029615Gallusgallus          CTCAATTAAGATACATTGAAGATATCCAACCCAATACAGTCCATATGGCT   1833
                                 **          * ***** **     **** **  *    *****

D50306Rat                     CTGCAGATCCCACAGTACTTCCTCCTCACCTGCGGCGAGGTGGTCTTCTC   1851
NM_053079Musmusculus          CTGCAGATCCCACAGTACTTCCTTCTCACCTGCGGCGAGGTGGTCTTCTC   1830
XM_007063Homosapiens          CTGCAAATCCCGCAGTATTTTCTTCTCACCTGTGGCGAAGTGGTCTTCTC   1792
AY027496Ovis                  CTGCAGATCCCCCAGTACTTCCTCCTCACCTGTGGCGAGGTGGTCTTCTC   1872
U13707Oryctolaguscunic        TGGCAAATCCCACAGTACTTCCTCATCACCTCTGGCGAGGTGGTCTTCTC   1797
SequencetosubmitGenbak        CTGCAGATCCCGCAGTACTTCCTCATCACCTGCGGCGAGGTGGTTTTCTC   1755
AY029615Gallusgallus          TGGCAGATCCCTCAGTATTTCATACTTACATGTGGAGAAGTAGTCTTCTC   1883
                                *** ***** ***** **  *  * ** *  ** ** ** ** *****

D50306Rat                     TGTCACAGGACTGGAGTTCTCCTATTCCCAGGCCCCGTCTAACATGAAGT   1901
NM_053079Musmusculus          TGTCACAGGACTGGAGTTCTCTTATTCCCAGGCTCCGTCTAACATGAAGT   1880
XM_007063Homosapiens          TGTCACGGGATTGGAATTCTCATATTCTCAGGCTCCTTCCAACATGAAGT   1842
AY027496Ovis                  CATCACCGGCCTGGAGTTCTCCTATTCTCAGGCTCCTTCCAACATGAAGT   1922
U13707Oryctolaguscunic        CATCACGGGCCTGGAGTTCTCCTATTCTCAGGCTCCTTCCAACATGAAGT   1847
SequencetosubmitGenbak        TGTCACAGGACTGGAGTTCTCATATTCTCAGGCCCCCTCCAACATGAAGT   1805
AY029615Gallusgallus          TGTCACTGGGCTGGAGTTTTCATACTCACAGGCACCATCTAATATGAAGT   1933
                                **** **  **** ** ** ** ** ***** ** ** ** *******

D50306Rat                     CCGTGCTTCAGGCAGgATGGCTTCTAACCGTGGCCATCGGTAATATCATT   1951
NM_053079Musmusculus          CCGTGCTTCAGGCAGGCTGGCTTCTAACTGTGGCGGTCGGCAATATCATT   1930
XM_007063Homosapiens          CGGTGCTTCAGGCAGGATGGCTGCTGACCGTGGCTGTTGGCAACATCATT   1892
AY027496Ovis                  CGGTACTTCAGGCAGGATGGCTGTTGACCGTGGCCGTTGGCAACATCATC   1972
U13707Oryctolaguscunic        CGGTGCTGCAGGACCGGTGGCTGCTGACGGTGGCTGTGGGCAACATCATT   1897
SequencetosubmitGenbak        CGGTGCTTCAGGCGGGATGGCTGCTGACAGTGGCT---------------   1840
AY029615Gallusgallus          CAGTGCTGCAAGCAGGATGGCTGCTAACAGTGGCTGTCGGTAACATAATT   1983
                              * ** ** ** *   * *****  * ** *****

D50306Rat                     GTCCTCATTGTGGCTGAGGCAGGCCACTTCGACAAACAGTGGGCTGAGTA   2001
NM_053079Musmusculus          GTGCTCATCGTGGCAGGGGCGGGGCACTTCCCCAAACAGTGGGCTGAGTA   1980
XM_007063Homosapiens          GTGCTCATCGTGGCAGGGGCAGGCCAGTTCAGCAAACAGTGGGCCGAGTA   1942
AY027496Ovis                  GTGCTTATTGTGGCAGGAGCAGGCCAGTTCAGTGAACAGTGGGCCGAGTA   2022
U13707Oryctolaguscunic        GTGCTCATCGTGGCCGGCGCGGGCCAGATCAACAAGCAGTGGGCCGAGTA   1947
SequencetosubmitGenbak        --------------------------------------------------
AY029615Gallusgallus          GTCCTTATCGTGGCTGGAGCATCCAAACTCAGTGAGCAGTGGGCAGAATA   2033

D50306Rat                     TGTTCTGTTCGCCTCCTTGCTCCTGGTCGTCTGCATCATATTTGCCATTA   2051
NM_053079Musmusculus          CATTCTGTTTGCCTCATTGCTTCTGGTTGTCTGCGTGATATTCGCCATCA   2030
XM_007063Homosapiens          CATTCTATTTGCCGCGTTGCTTCTGGTCGTCTGTGTAATTTTTGCCATCA   1992
AY027496Ovis                  CGTTCTGTTTGCGGCATTGCTTCTGGTCGTCTGCATAATATTTGCCATCA   2072
U13707Oryctolaguscunic        CATCCTCTTTGCCGCCCTGCTCCTGGTCGTCTGTGTCATATTTGCCATCA   1997
SequencetosubmitGenbak        --------------------------------------------------
AY029615Gallusgallus          TGTTCTCTTTGCTGCCTTGCTTTTTGCAGTTTGCATTATTTTTGCTGTCA   2083

D50306Rat                     TGGCCCGATTCTACACCTACATCAACCCAGCAGAGATCGAGGCACAGTTC   2101
NM_053079Musmusculus          TGGCTCGATTCTACACCTACATCAACCCAGCAGAGATTGAAGCACAGTTT   2080
XM_007063Homosapiens          TGGCTCGGTTCTATACTTACATCAACCCAGCGGAGATCGAAGCTCAATTT   2042
AY027496Ovis                  TGGCTCGATTCTATACGTATGTCAACCCCGCAGAGATTGAAGCTCAGTTT   2122
U13707Oryctolaguscunic        TGGCTCGATTCTATACGTATGTCAACCCGGCCGAGATCGAGGCTCAGTTT   2047
SequencetosubmitGenbak        --------------------------------------------------
AY029615Gallusgallus          TGGCATATTTTTATACATATACTGATCCAAATGAGGTTGAAGCCCAACTT   2133

D50306Rat                     GATGAGGATGAGAAGAAAAAGGGCGTAGGGAAGGAA---AACCCGTATTC   2148
NM_053079Musmusculus          GATGAGGATGAGAAGAAAAAGGGCATAGGAAAGGAA---AACCCGTATTC   2127
XM_007063Homosapiens          GATGAGGATGAAAAGAAAAACAGACTGGAAAAGAGT---AACCCATATTT   2089
AY027496Ovis                  GATGAGGATGACAAGGAGGATGACCTGGAAAAGAGT---AACCCATACGC   2169
U13707Oryctolaguscunic        GAAGAAGATGAGAAGAAAAAGAACCCAGAAAAGAAC---GACCTCTACCC   2094
SequencetosubmitGenbak        --------------------------------------------------
AY029615Gallusgallus          GATGAAGAAGAAAAGAAGAAACAAATAAAACAGGATCCAGACTTGCACGG   2183

D50306Rat                     CTCG---TTGGAACCTGTCTCACAGACAAACATGTGAAGATCAGAAAGCA   2195
NM_053079Musmusculus          TTCA---TTGGAACCAGTCTCACAGACAAATATGTGAAGGGCAGAAGGCA   2174
XM_007063Homosapiens          CATG---TCAGGGGCCAATTCACAGAAACAGATGTGAAGGTCAGGAGGCA   2136
AY027496Ovis                  CAAG---CTGGACTTCGTCTCACAGACACAAATGTGAATGTCAGGAAGCA   2216
U13707Oryctolaguscunic        CTCC---GTGGCGCCCGTCTCACAGACACAGATGTGA--GTCTGGAGGCG   2139
SequencetosubmitGenbak        --------------------------------------------------
AY029615Gallusgallus          AAAAGAATCTGAAGCTGTCTCTCAGATGTAGAAG-GTGTATTCAAGAGCA   2232

D50306Rat                     AGTGGAGAACATACCAAGTC--CAGCATTCACCATGACCTCTGCCC--AA   2241
NM_053079Musmusculus          AATTGGAGAAAGATCAAGTT--CAACATGAGCCCTGACCTCTGTCC--AA   2220
XM_007063Homosapiens          AGTGGAGGATGGACTGGGCC--C-GCAGATGCCCTGACCTCTGCCCCCAG   2183
AY027496Ovis                  AGCGGACGC-GGGGCTGGGC--CAGGGTGTGCCCAGGGGTCTGTCCCATG   2263
U13707Oryctolaguscunic        -GTGTAGGA-GGCCCACGCC--TGGCGTGCACTGTGACCTCTGTCCGA-G   2184
SequencetosubmitGenbak        --------------------------------------------------
```

-continued

| | | |
|---|---|---|
| AY029615Gallusgallus | TTTGTAAATCATGGTAGCCTGTTAACTGTCCCTGCAATAACAGGAATCAG | 2282 |
| | | |
| D50306Rat | GGGACAGGACCCTCCACCACAGAGTCCTTGCTGGAGAAAGACTTCAGACA | 2291 |
| NM_053079Musmusculus | GGGACAGGACACTCCACCACAGAGTCCCTGATGGAGAAAGACCTCAGAAG | 2270 |
| XM_007063Homosapiens | GTAGCAGGACACTCCATTGGATGGCCCCTGATG-AGGAAGACTTCAGAAT | 2232 |
| AY027496Ovis | GGGGCAGGACACTCTGTTGGGTGGCCTCTGATG-GGGAAGACTTCAGAAC | 2312 |
| U13707Oryctolaguscunic | GGCGCAGGACGTACCCCTGGGCAGCCCCGGAAG-GGGAGGACTTGAGAAC | 2233 |
| SequencetosubmitGenbak | -------------------------------------------------- | |
| AY029615Gallusgallus | GGTATTGCTGACATCACTGGGTAATATACCTTGTGGGAGAGACTAAGAAA | 2332 |
| | | |
| D50306Rat | TGTGAGCCAAAATAATAACAAAGCAGGTTTTCAGGCTGACGGCTGTGAAT | 2341 |
| NM_053079Musmusculus | TGTGAGCCAGAATAATAACAAAGCAGGTTTTCTAACCAACAGCTGTGAAC | 2320 |
| XM_007063Homosapiens | TGGGAACTAAACCATGAATGC--TATTTTCTTTTTTCTTTTTCTTTTCTT | 2280 |
| AY027496Ovis | TGTGGACCAAACCAAGACAGC--TGCTTTCTC-AGCAGCCGGCAATGAAC | 2359 |
| U13707Oryctolaguscunic | TGTGAACCAGACCACGAAAGC--TATGTTCTG-AGCAGCCAGTGATGAGT | 2280 |
| SequencetosubmitGenbak | -------------------------------------------------- | |
| AY029615Gallusgallus | CACTGTTCTGACTTAACATAC---AGCCTCTTGGGAAGCAAGACGAAATG | 2379 |
| | | |
| D50306Rat | CTGAAACTCTAGGGGAGCCTTTTT-------------------------- | 2365 |
| NM_053079Musmusculus | CTGAAACTCTAGGGGAGCCTTTTTATTTAAAAAAATTTTTTTTTTAATT | 2370 |
| XM_007063Homosapiens | TTTTTTTTTT-------TTTTTTTTTTGAGACAGAGTTTTGCTCTTGTT | 2323 |
| AY027496Ovis | CTGAAACTCCAAAAGACGTCCTTTT------------------------- | 2384 |
| U13707Oryctolaguscunic | CCAAAACTCTGAAAGAAATCTTGTT------------------------- | 2305 |
| SequencetosubmitGenbak | -------------------------------------------------- | |
| AY029615Gallusgallus | ATTAATCTCTTGTACAGAAGCTGGC------------------------- | 2404 |
| | | |
| D50306Rat | -------------------------------------------------- | |
| NM_053079Musmusculus | TTTTAAATTTTTTTATTTTTTATTTTTTTTGCTTGTTTGTTTGTTTCGA | 2420 |
| XM_007063Homosapiens | GTCCAGGCTGGAGTGCAATGGCACGATCTCAGCTCACTGC---------A | 2364 |
| AY027496Ovis | -------------------------------------------------- | |
| U13707Oryctolaguscunic | -------------------------------------------------- | |
| SequencetosubmitGenbak | -------------------------------------------------- | |
| AY029615Gallusgallus | -------------------------------------------------- | |
| | | |
| D50306Rat | -------------------------------------------------- | |
| NM_053079Musmusculus | GACAGGGTTTCTCGTGTGTAGCCCTTGGTTGTCCTGGAACTCACTCTGTA | 2470 |
| XM_007063Homosapiens | ACCTCCGCCTCCCAGGTTCAAGTAATTCTCCTGCCTCAGCCTCCCGAGTG | 2414 |
| AY027496Ovis | -------------------------------------------------- | |
| U13707Oryctolaguscunic | -------------------------------------------------- | |
| SequencetosubmitGenbak | -------------------------------------------------- | |
| AY029615Gallusgallus | -------------------------------------------------- | |
| | | |
| D50306Rat | -------------------------------------------------- | |
| NM_053079Musmusculus | GACCAGACTGGCCTCAAACTCAGAAATCCACCTGCCCCTGCCCCTGCCCC | 2520 |
| XM_007063Homosapiens | GCTGGGATTAGCGGCA---------------------------------- | 2430 |
| AY027496Ovis | -------------------------------------------------- | |
| U13707Oryctolaguscunic | -------------------------------------------------- | |
| SequencetosubmitGenbak | -------------------------------------------------- | |
| AY029615Gallusgallus | -------------------------------------------------- | |
| | | |
| D50306Rat | -------------------------------------------------- | |
| NM_053079Musmusculus | TGCCCCTGCCCCTGCCCCTGCCTCTGCCTCTGCCTCCCAAGTGCTGGATT | 2570 |
| XM_007063Homosapiens | ------TGCACCACCACGCCCAGCTATTTTTGTATTTTTAGTAGAGAT-- | 2472 |
| AY027496Ovis | -------------------------------------------------- | |
| U13707Oryctolaguscunic | -------------------------------------------------- | |
| SequencetosubmitGenbak | -------------------------------------------------- | |
| AY029615Gallusgallus | -------------------------------------------------- | |
| | | |
| D50306Rat | -----------------------------AATTTGTTTTTCTTGAGACAA | 2386 |
| NM_053079Musmusculus | TGGAGGCATGCACCACCATGCCCAGCTATAATTTTTTTTTTTTAAGACAG | 2620 |
| XM_007063Homosapiens | ---GGGGTTTCACCATGTTGGCCAGG-ATGGTCTCGATCTCTTGACCTGG | 2518 |
| AY027496Ovis | -------------------------------------------------- | |
| U13707Oryctolaguscunic | -------------------------------------------------- | |
| SequencetosubmitGenbak | -------------------------------------------------- | |
| AY029615Gallusgallus | -------------------------------------------------- | |
| | | |
| D50306Rat | GGTATCTCTGTGTAACCCTGGCTATCCTGGAACTCACTCTATAGACCAGG | 2436 |
| NM_053079Musmusculus | GGATTCTCTGTATAAGCCTGACTGCCCTGGAACTTGCTCTATAGACCAGG | 2670 |
| XM_007063Homosapiens | TGA---TCTGCCCACCTCGGCCTGCCAAAGTGCTGGGATTACAGGCTTGA | 2565 |
| AY027496Ovis | -------------------------------------------------- | |
| U13707Oryctolaguscunic | -------------------------------------------------- | |
| SequencetosubmitGenbak | -------------------------------------------------- | |
| AY029615Gallusgallus | -----------------------ATCCTGAGGAAACTCCTGCAGAATTTG | 2431 |
| | | |
| D50306Rat | CTGGCCTCGAACTCACAGATATCTGTCTGCCTCTGCCTCCTAAGTACTGG | 2486 |
| NM_053079Musmusculus | CTGGCCTTGAACTCACAGAGATCTGCCTGCCTCTTCCTCCTAAGTACTGG | 2720 |
| XM_007063Homosapiens | GCTACCGCGCCCGGCCGTGAACGCTATTTTCTAAGCAGCC--AGCAGTGA | 2613 |
| AY027496Ovis | ------------------------GTTTGTTTGTTTTTAG--AGAAGTCT | 2408 |
| U13707Oryctolaguscunic | ------------------------G------------------AAAGTCT | 2313 |
| SequencetosubmitGenbak | -------------------------------------------------- | |

-continued

```
AY029615Gallusgallus        CACTCTTAAAATGTACCTCAAGCTCAATACCATAGCATTA-AAATATTGA   2480

D50306Rat                   GATTCAAGGCATGTACGGCAACTGCCCAGCTAAAATATTATTTATAACAT   2536
NM_053079Musmusculus        GATTTCAGGCATGCACCACAACTGCCCAGCTAAAATATTATTTATAATAT   2770
XM_007063Homosapiens        ATCTAAAACTCTGGAAGAAGTCTTCTGTTTGAAAGGCTTATTTAAGCCAC   2663
AY027496Ovis                TATTTAAAGCGCACAC-ACACGCACACGCACACA-------------CAT   2444
U13707Oryctolaguscunic      TATTTAAAACACACAC-ACACACACACACACACA-------------CAC   2349
SequencetosubmitGenbak      --------------------------------------------------
AY029615Gallusgallus        AATTGCACTTGGCACTATTAGACACTCTAAAAAGATGTATTTT----TAT   2526

D50306Rat                   GCACTTTCTGGGTTTTTTGTTTTTAAAACATACTTTTTTTTTTAACACTG   2586
NM_053079Musmusculus        GCACTTTCTGG----TTTGTTTTTG--------TTTTTCTTTTAA-ACTG   2807
XM_007063Homosapiens        ACGTACACACA-----CTGTCTTAGA-------GTACTGTGAGCCCACCC   2701
AY027496Ovis                GCACACACACA------CACTTTTAT----------AAGAGTCCATACTC   2478
U13707Oryctolaguscunic      ACACACTTTTC------CAACACTG------------ACAGCCTAC---C   2378
SequencetosubmitGenbak      --------------------------------------------------
AY029615Gallusgallus        ACTGTATTTCAATTTTATAATGTGGAGGGGTGGGGAAAAAGGTGTTGCCA   2576

D50306Rat                   GGCCATTTCTAACATTTCTGCCACAGAAGTGGATTTAGCTCAGATTAA--   2634
NM_053079Musmusculus        GGCTGTATCTTACATTTCTGCCACAGAAATGAACTTAGCTCAGATTAACT   2857
XM_007063Homosapiens        CACATTGGTCATCTTCCCTATCACACAAATGATGTTATTTTGGACTAGCT   2751
AY027496Ovis                TGCCTGAACTCCTTTTCCTAACACACAAATAAAGTTATTTTGGACTAACT   2528
U13707Oryctolaguscunic      CATGTTAACTCCTTCTCTACCAATGCAAATGCTGTTATTTTGGACTAACT   2428
SequencetosubmitGenbak      --------------------------------------------------
AY029615Gallusgallus        AGAAATAGTAATTGAAGCCAAACTGTCTGCGTGACCCTTCTAGCCTCACT   2626

D50306Rat                   -----TTTTGAAAAGGTAACAGTACTGTTTTTTT-----------TCCTT   2668
NM_053079Musmusculus        T--AATTTTGAAAAGGCAATAGTATTGTTTTTT---------------CT   2890
XM_007063Homosapiens        T--AATTTTGAAATGGTAACAAAGTTTCCTATTCCATACTGTTCATTTCT   2799
AY027496Ovis                TGAATTTTTGAAATGGTGGCCAAGCTCCATACGT-----------GCATT   2567
U13707Oryctolaguscunic      T-AATTTTGAACACTGTT-CTATGTTGCTTGTAT-----------TC--T   2463
SequencetosubmitGenbak      --------------------------------------------------
AY029615Gallusgallus        GTTACTTGAAAGCAGGTCAC-ATGTGCCTTAAATT---------CTTTTC   2666

D50306Rat                   AATGCTCTTA-TGAAAACAATGTTGAA-----------------TTTACA   2700
NM_053079Musmusculus        AACAGTTTTA-TGAAAACAATATTGAA-----------------TTTACA   2922
XM_007063Homosapiens        AATACTCTTA-CGAAACTATTCTAAAGGAGGCAGGAGCCAAGGCCAAAA   2848
AY027496Ovis                CGCACACTCTGTGCAAACAATGTTAAAGGAGGCAAAAAGTGA----ATGG   2613
U13707Oryctolaguscunic      AACATCCTTAGGAAAGGCAATGTTAAGAGAGGCAGGAGGCAATGCCAAAG   2513
SequencetosubmitGenbak      --------------------------------------------------
AY029615Gallusgallus        TATGTCCTTA---AGAATAATAGGAGAAAG----------------GTTC   2697

D50306Rat                   GAGGGCTT-------TTTTAGCAGTGTGTAGTGAGTGTCAGCTGATTCGA   2743
NM_053079Musmusculus        GAGGGCTT-------TTTTAATAGTGTGTAATGAGTATCAACTGATTCAA   2965
XM_007063Homosapiens        GTGAACGTACAGG--TTTGAAATGGCTGTGATAAGGACCAGCTGGTATTA   2896
AY027496Ovis                TTGGGGCTTTTGA-ATAGTACGTGTTCATAATAAGGACCGGCTGGTATTA   2662
U13707Oryctolaguscunic      TTGAATATGTAGGTGTCAGAATGGTATATACCACATATTACTTAGTATTA   2563
SequencetosubmitGenbak      --------------------------------------------------
AY029615Gallusgallus        TTAGATTTC------TCAGATTAAAATGT-CTCTGCTCCACATAGCAGGA   2740

D50306Rat                   GCTAATAACCTTACCTCGGGGTTTTT----------------------GT   2771
NM_053079Musmusculus        GCTAATTGCTTTACCTTGGGGTTTTTTTGTTTGTTTGTTTGTTTGTTTGT   3015
XM_007063Homosapiens        ACTGATAACTTTACCTTTGGGTTTTT----------------------GT   2924
AY027496Ovis                ACTGATAACTCTACCTTCTGTTTTTA------------------------   2688
U13707Oryctolaguscunic      ACTGAAAACCTCAACTTTGAGGTTTT------------------------   2589
SequencetosubmitGenbak      --------------------------------------------------
AY029615Gallusgallus        ACTTGGACATGCACTGTGATGTGCTT----------------------T    2767

D50306Rat                   TTCTTTGTTTTCCTGGTCTCCTTTGCCTGACCTCTTTTTAAATTATGTGT   2821
NM_053079Musmusculus        TTGTTTGTTTTTCTAGTCTCCTTTGCCTTACCTCTTTTTAAATTATGTGT   3065
XM_007063Homosapiens        TATTTTGTTTTTCTAGTCCCT--------ACCTGTGTTTAAATTATGGAT   2966
AY027496Ovis                -GTTCTGTTTTT-CCATTCCCT-------ACCTCTTTGTAAATTATGGAT   2729
U13707Oryctolaguscunic      -GTTCTATTTTTTCCACTCCTT-------ACCTCTTTTTAACCTGTGGAC   2631
SequencetosubmitGenbak      --------------------------------------------------
AY029615Gallusgallus        ATGTGCCTATTATTAACTGCCCATTGGTATGTTCTTAATTAATTGTGT-T   2816

D50306Rat                   AA---TTCAAAAGACTATTCAAGTGAT-GGTTAGTCATGAGTCGT--GAC   2865
NM_053079Musmusculus        AA---TTCAAAAGACTA----------------GTCATGAGTTGT--GAA   3094
XM_007063Homosapiens        AA---CTCGAAAGACAGCTCAGGTGAA-GGCCAGTAATGATTTTTTTGAA   3012
AY027496Ovis                TAACCTTTGAAAAACCACTCAGGTAAA-GGCAAGTCATGATTTTT--GGA   2776
U13707Oryctolaguscunic      AA--CTCAAAAGGACCACTCAGATAAA-GGCCAGTAAAGATTTTT--TTT   2676
SequencetosubmitGenbak      --------------------------------------------------
AY029615Gallusgallus        AA----TGGGATGTCCACTGAGGTGAACAGACAATGGCAAATTATATTTT   2862

D50306Rat                   GTTTGACTGGTGTGAAGTAAATTCTTGTTCTTAAG---------------   2900
NM_053079Musmusculus        GTTTCACTGGTCTGAAATAAATTCTAGTTCTTAA----------------   3128
XM_007063Homosapiens        GTTTCAATGGTGTGAAATAAATTTCTGTTCTTA-----------------   3045
AY027496Ovis                GTCTCAACGGTATGAAATAAACTCTCATTCTCAAGAAAAAAAAAAAAAAA   2826
U13707Oryctolaguscunic      GCCGTTTTG--ATGAAATAAAATAATGTTCCTAAG---------------   2709
SequencetosubmitGenbak      --------------------------------------------------
```

-continued

```
AY029615Gallusgallus          GAATAACCACCAAGAATAAAACTTGTGTTGTAACAAAAAAAAAAAAAAA    2912

D50306Rat                     ---
NM_053079Musmusculus          ---
XM_007063Homosapiens          ---
AY027496Ovis                  AAA                                                  2829
U13707Oryctolaguscunic        ---
SequencetosubmitGenbak        ---
AY029615Gallusgallus          AA-                                                  2914
```

Alignment of Nucleotide Full Length Sequence of Canine and Human

Sequence 1: SequencetosubmitGenbank  1840 bp

Sequence 2: XM_007063Homosapiens     3045 bp

Start of Pairwise alignments

Aligning. . .

Sequences (1:2) Aligned. Score: 85

Guide tree file created:

[/net/nfs0/vol1/production/w3nobody/tmp/305133.88341-239044.dnd]

Start of Multiple Alignment

There are 1 groups

Aligning. . .

Group 1: Sequences: 2 Score:31290

Alignment Score 10725

CLUSTAL-Alignment file created

[/net/nfs0/vol1/production/w3nobody/tmp/305133.88341-239044.aln]

Your Multiple Sequence Alignment:

305133.88341-239044.aln

CLUSTAL W (1.81) multiple sequence alignment

```
                                                                                   (SEQ ID NO:7)
SequencetosubmitGenbank       ----------------------------------------CATCTTCTTC  10

                                                                                   (SEQ ID NO:1)
XM_007063Homosapiens          GAATGTCCAAATCACACAGTTTCTTTGGTTATCCCCTGAGCATCTTCTTC  50
                                                                      **********

SequencetosubmitGenbank       ATCGTGGTCAATGAGTTCTGTGAAAGATTTTCCTACTATGGAATGAGAGC  60
XM_007063Homosapiens          ATCGTGGTCAATGAGTTTTGCGAAAGATTTTCCTACTATGGAATGCGAGC  100
                              ***************** ** ************************ ****

SequencetosubmitGenbank       ACTCCTGATTCTGTACTTCAGACGGTTCATCGGGTGGGACGATAATCTGT  110
XM_007063Homosapiens          AATCCTGATTCTGTACTTCACAAATTTCATCAGCTGGGATGATAACCTGT  150
                              * ****************** *   ****** * ***** ***** ****

SequencetosubmitGenbank       CCACGGCCATCTACCACACGTTTGTGGCTCTGTGCTACCTGACGCCGATC  160
XM_007063Homosapiens          CCACCGCCATCTACCATACGTTTGTGGCTCTGTGCTACCTGACGCCAATT  200
                              **** *********** ***************************** **

SequencetosubmitGenbank       CTCGGCGCACTGATCGCAGACTCCTGGCTGGGAAAGTTCAAGACAATCGT  210
XM_007063Homosapiens          CTCGGAGCTCTTATCGCCGACTCGTGGCTGGGAAAGTTCAAGACCATTGT  250
                              ***** ** ** ***** ***** ******************** ** **

SequencetosubmitGenbank       GTCACTCTCCATTGTCTACACAATTGGACAGGCGGTCACTGCAGTAAGCT  260
XM_007063Homosapiens          GTCGCTCTCCATTGTCTACACAATTGGACAAGCAGTCACCTCAGTAAGCT  300
                              *** ************************** ** *****  *********

SequencetosubmitGenbank       CAATTAATGACCTCACAGACTATAACAAAGATGGAACTCCTGACAATCTG  310
XM_007063Homosapiens          CCATTAATGACCTCACAGACCACAACCATGATGGCACCCCCGACAGCCTT  350
                              * ****************** * *** * ***** ** ** ****  **

SequencetosubmitGenbank       TCCGTGCATGTGGCACTGTCCATGATTGGCCTGGCCCTGATAGCTCTGGG  360
XM_007063Homosapiens          CCTGTGCACGTGGTGCTGTCCTTGATCGGCCTGGCCCTGATAGCTCTCGG  400
                               * ***** ****  ****** **** ******************** **
```

-continued

```
SequencetosubmitGenbank        AACTGGAGGAATAAAGCCCTGTGTGTCTGCATTTGGTGGAGACCAGTTTG  410
XM_007063Homosapiens           GACTGGAGGAATCAAACCCTGTGTGTCTGCGTTTGGTGGAGATCAGTTTG  450
                                *********** ** ************** *********** *******

SequencetosubmitGenbank        AAGAGGGCCAGGAAAAACAAAGAAACAGATTCTTTTCCATCTTTTATTTG  460
XM_007063Homosapiens           AAGAGGGCCAGGAGAAACAAAGAAACAGATTTTTTTCCATCTTTTACTTG  500
                               ************* ***************** ************** ***

SequencetosubmitGenbank        GCCATTAATGCTGGAAGCTTGATTTCCACTATTGTCACTCCCATGCTCAG  510
XM_007063Homosapiens           GCTATTAATGCTGGAAGTTTGCTTTCCACAATCATCACACCCATGCTCAG  550
                               ** ************** *** ******* **  **** ***********

SequencetosubmitGenbank        AGTTCACGAATGTGGAATTTACAGTCAGAAAGCTTGTTACCCACTGGCAT  560
XM_007063Homosapiens           AGTTCAACAATGTGGAATTCACAGTAAACAAGCTTGTTACCCACTGGCCT  600
                               ******  *********** ***** *  ******************* *

SequencetosubmitGenbank        TTGGGGTTCCTGCTGCTCTCATGGCCGTATCTCTGATTGTATTTGTCATT  610
XM_007063Homosapiens           TTGGGGTTCCTGCTGCTCTCATGGCTGTAGCCCTGATTGTGTTTGTCCTT  650
                               ************************* *** * ******** ****** **

SequencetosubmitGenbank        GGCAGTGGAATGTACAAGAAGTTTCAGCCCCAGGGTAATGTCATGGGTAA  660
XM_007063Homosapiens           GGCAGTGGGATGTACAAGAAGTTCAAGCCACAGGGCAACATCATGGGTAA  700
                               ******** **************  **** ***** **  **********

SequencetosubmitGenbank        AGTTGTCAAGTGCATTGGTTTTGCCCTCAAAAATAGGTTTAGGCACCGGA  710
XM_007063Homosapiens           AGTGGCCAAGTGCATCGGTTTTGCCATCAAAAATAGATTTAGGCATCGGA  750
                               *** * ********* ********* ********** ******** ****

SequencetosubmitGenbank        GTAAGCAGTTTCCCAAGAGGGAGCACTGGCTGGACTGGGCTAAAGAGAAA  760
XM_007063Homosapiens           GTAAGGCATTTCCCAAGAGGGAGCACTGGCTGGACTGGGCTAAAGAGAAA  800
                               *****   ******************************************

SequencetosubmitGenbank        TACGATGAGCGGCTCATCTCTCAAATTAAGATGGTCACAAAAGTGATGTT  810
XM_007063Homosapiens           TACGATGAGCGGCTCATCTCCCAAATTAAGATGGTTACGAGGGTGATGTT  850
                               ******************** ************** ** *  ********

SequencetosubmitGenbank        CTTGTACATCCCACTCCCAATGTTCTGGGCCCTGTTTGACCAGCAGGGCT  860
XM_007063Homosapiens           CCTGTATATTCCACTCCCAATGTTCTGGGCCTTGTTTGACCAGCAGGGCT  900
                               * **** ** ********************* ******************

SequencetosubmitGenbank        CCAGGTGGACACTGCAAGCAACAGCTATGAGTGGGAAAATTGGACTTCTT  910
XM_007063Homosapiens           CCAGGTGGACACTGCAGGCAACAACTATGTCCGGGAAAATCGGAGCTCTT  950
                               **************** ****** *****   ******** ***  ****

SequencetosubmitGenbank        GAAGTTCAGCCAGATCAGATGCAGACTGTGAATGCCATCTTGATTGTCGT  960
XM_007063Homosapiens           GAAATTCAGCCCGATCAGATGCAGACCGTGAACGCCATCCTGATCGTGAT  1000
                               *** ******* ************** ***** ****** **** **  *

SequencetosubmitGenbank        CATGGTCCCCATCATGGATGCCGTGGTGTACCCTCTGATTGCAAAATGTG  1010
XM_007063Homosapiens           CATGGTCCCGATCTTCGATGCTGTGCTGTACCCTCTCATTGCAAAATGTG  1050
                               ********* *** * ***** *** ********** *************

SequencetosubmitGenbank        GCTTCAATTTCACCTCCTTGAAGAGGATGACAGTTGGAATGTTCCTGGCT  1060
XM_007063Homosapiens           GCTTCAATTTCACCTCCTTGAAGAAGATGGCAGTTGGCATGGTCCTGGCC  1100
                               ************************ **** ******* *** ******* 

SequencetosubmitGenbank        TCCATGGCCTTCGTGATGGCGGCGATTGTTCAGCTGGAAATTGATAAAAC  1110
XM_007063Homosapiens           TCCATGGCCTTTGTGGTGGCTGCCATCGTGCAGGTGGAAATCGATAAAAC  1150
                               *********** *** **** ** ** ** *** ******* ********

SequencetosubmitGenbank        TCTTCCAGTCTTCCCCAAACAAAATGAAGTCCAAATCAAAGTACTGAATA  1160
XM_007063Homosapiens           TCTTCCAGTCTTCCCCAAAGGAAACGAAGTCCAAATTAAAGTTTTGAATA  1200
                               *******************  *** *********** *****  ******

SequencetosubmitGenbank        TAGGAAATGGTGCCATGAATGTATCTTTTCCTGGAGCGGTGGTGACAGTT  1210
XM_007063Homosapiens           TAGGAAACAATACCATGAATATATCTCTTCCTGGAGAGATGGTGACACTT  1250
                               *******   * ******** ***** ********* * ******** **

SequencetosubmitGenbank        AGCCAAATGAGTCAATCAGATGGATTTATGACTTTTGATGTAGACAAACT  1260
XM_007063Homosapiens           GGCCCAATGTCTCAAACAAATGCATTTATGACTTTTGATGTAAACAAACT  1300
                                *** ****  **** ** *** ******************* *******

SequencetosubmitGenbank        GACAAGTATAAACATTTCTTCCACTGGATCACCAGTCATTCCAGTGACTT  1310
XM_007063Homosapiens           GACAAGGATAAACATTTCTTCTCCTGGATCACCAGTCACTGCTGTAACTG  1350
                               ****** **************  *************** * * ** ***

SequencetosubmitGenbank        ATAACTTTGAGCAGGGCCATCGCCATACCCTTCTAGTATGGGCCCCCAAT  1360
XM_007063Homosapiens           ACGACTTCAAGCAGGGCCAACGCCACACGCTTCTAGTGTGGGCCCCCAAT  1400
                               *  ****  ********** ***** ** ******** ************
```

-continued

```
SequencetosubmitGenbank    AATTACCGAGTGGTAAAGGATGGCCTTAACCAGAAGCCAGAAAAAGGAGA  1410
XM_007063Homosapiens       CACTACCAGGTGGTAAAGGATGGTCTTAACCAGAAGCCAGAAAAAGGGGA  1450
                            * ****  ************** *********************** **

SequencetosubmitGenbank    AAATGGAATCAGATTTATAAATAGTCTTAATGAGAGCCTCAACATCACCA  1460
XM_007063Homosapiens       AAATGGAATCAGATTTGTAAATACTTTTAACGAGCTCATCACCATCACAA  1500
                           **************** ****** * **** ***  * *** ****** *

SequencetosubmitGenbank    TGGGCGACAAAGTTTATGTGAATGTCACCAGTCACAATGCCAGCGAGTAT  1510
XM_007063Homosapiens       TGAGTGGGAAAGTTTATGCAAACATCAGCAGCTACAATGCCAGCACATAC  1550
                           ** * *  **********  **  *** ***  ***********   **

SequencetosubmitGenbank    CAGTTCTTTTCTTTGGGCACAAAAAACATTACAATAAGTTCAACACAACA  1560
XM_007063Homosapiens       CAGTTTTTTCCTTCTGGCATAAAAGGCTTCACAATAAGCTCAACAG---A  1597
                           ***** *** ***  **** ****  * * ******** ******    *

SequencetosubmitGenbank    GATCTCACAAAATTGTACAAAAGTTCTCCAATCATCCAACCTTGAATTTG  1610
XM_007063Homosapiens       GATTCCGCCACAATGTCAACCTAATTTCAATACTTTCTACCTTGAATTTG  1647
                           ***  * * * * ***  *     * ** *  * * * ************

SequencetosubmitGenbank    GTAGTGCATATACCTATGTAATCGGAACGCAGAGCACTGGCTGCCCTGAA  1660
XM_007063Homosapiens       GTAGTGCTTATACCTATATAGTCCAAAGGAAGAATGACAGCTGCCCTGAA  1697
                           ******* ********* ** **  ** * ***      ***********

SequencetosubmitGenbank    TTGCATATGTTTGAAGATATTTCACCCAACACAGTTAACATGGCTCTGCA  1710
XM_007063Homosapiens       GTGAAGGTGTTTGAAGATATTTCAGCCAACACAGTTAACATGGCTCTGCA  1747
                            ** *  ***************** *************************

SequencetosubmitGenbank    GATCCCGCAGTACTTCCTCATCACCTGCGGCGAGGTGGTTTTCTCTGTCA  1760
XM_007063Homosapiens       AATCCCGCAGTATTTTCTTCTCACCTGTGGCGAAGTGGTCTTCTCTGTCA  1797
                            *********** ** **  ******* ***** ***** **********

SequencetosubmitGenbank    CAGGACTGGAGTTCTCATATTCTCAGGCCCCCTCCAACATGAAGTCGGTG  1810
XM_007063Homosapiens       CGGGATTGGAATTCTCATATTCTCAGGCTCCTTCCAACATGAAGTCGGTG  1847
                           * *** **** ***************** ** ******************

SequencetosubmitGenbank    CTTCAGGCGGGATGGCTGCTGACAGTGGCT--------------------  1840
XM_007063Homosapiens       CTTCAGGCAGGATGGCTGCTGACCGTGGCTGTTGGCAACATCATTGTGCT  1897
                           ******** ************** ******

SequencetosubmitGenbank    --------------------------------------------------
XM_007063Homosapiens       CATCGTGGCAGGGGCAGGCCAGTTCAGCAAACAGTGGGCCGAGTACATTC  1947

SequencetosubmitGenbank    --------------------------------------------------
XM_007063Homosapiens       TATTTGCCGCGTTGCTTCTGGTCGTCTGTGTAATTTTTGCCATCATGGCT  1997

SequencetosubmitGenbank    --------------------------------------------------
XM_007063Homosapiens       CGGTTCTATACTTACATCAACCCAGCGGAGATCGAAGCTCAATTTGATGA  2047

SequencetosubmitGenbank    --------------------------------------------------
XM_007063Homosapiens       GGATGAAAAGAAAAACAGACTGGAAAAGAGTAACCCATATTTCATGTCAG  2097

SequencetosubmitGenbank    --------------------------------------------------
XM_007063Homosapiens       GGGCCAATTCACAGAAACAGATGTGAAGGTCAGGAGGCAAGTGGAGGATG  2147

SequencetosubmitGenbank    --------------------------------------------------
XM_007063Homosapiens       GACTGGGCCCGCAGATGCCCTGACCTCTGCCCCCAGGTAGCAGGACACTC  2197

SequencetosubmitGenbank    --------------------------------------------------
XM_007063Homosapiens       CATTGGATGGCCCCTGATGAGGAAGACTTCAGAATTGGGAACTAAACCAT  2247

SequencetosubmitGenbank    --------------------------------------------------
XM_007063Homosapiens       GAATGCTATTTTCTTTTTTCTTTTTCTTTTCTTTTTTTTTTTTTTTTTTT  2297

SequencetosubmitGenbank    --------------------------------------------------
XM_007063Homosapiens       TTTTGAGACAGAGTTTTGCTCTTGTTGTCCAGGCTGGAGTGCAATGGCAC  2347

SequencetosubmitGenbank    --------------------------------------------------
XM_007063Homosapiens       GATCTCAGCTCACTGCAACCTCCGCCTCCCAGGTTCAAGTAATTCTCCTG  2397

SequencetosubmitGenbank    --------------------------------------------------
XM_007063Homosapiens       CCTCAGCCTCCCGAGTGGCTGGGATTAGCGGCATGCACCACCACGCCCAG  2447

SequencetosubmitGenbank    --------------------------------------------------
XM_007063Homosapiens       CTATTTTTGTATTTTTAGTAGAGATGGGGTTTCACCATGTTGGCCAGGAT  2497

SequencetosubmitGenbank    --------------------------------------------------
XM_007063Homosapiens       GGTCTCGATCTCTTGACCTGGTGATCTGCCCACCTCGGCCTGCCAAAGTG  2547
```

-continued

```
SequencetosubmitGenbank      --------------------------------------------------
XM_007063Homosapiens         CTGGGATTACAGGCTTGAGCTACCGCGCCCGGCCGTGAACGCTATTTTCT  2597

SequencetosubmitGenbank      --------------------------------------------------
XM_007063Homosapiens         AAGCAGCCAGCAGTGAATCTAAAACTCTGGAAGAAGTCTTCTGTTTGAAA  2647

SequencetosubmitGenbank      --------------------------------------------------
XM_007063Homosapiens         GGCTTATTTAAGCCACACGTACACACACTGTCTTAGAGTACTGTGAGCCC  2697

SequencetosubmitGenbank      --------------------------------------------------
XM_007063Homosapiens         ACCCCACATTGGTCATCTTCCCTATCACACAAATGATGTTATTTTGGACT  2747

SequencetosubmitGenbank      --------------------------------------------------
XM_007063Homosapiens         AGCTTAATTTTGAAATGGTAACAAAGTTTCCTATTCCATACTGTTGATTT  2797

SequencetosubmitGenbank      --------------------------------------------------
XM_007063Homosapiens         CTAATACTCTTACGAAAACTATTCTAAAGGAGGCAGGAGCCAAGGCCAAA  2847

SequencetosubmitGenbank      --------------------------------------------------
XM_007063Homosapiens         AGTGAACGTACAGGTTTGAAATGGCTGTGATAAGGACCAGCTGGTATTAA  2897

SequencetosubmitGenbank      --------------------------------------------------
XM_007063Homosapiens         CTGATAACTTTACCTTTGGGTTTTTGTTATTTTGTTTTTCTAGTCCCTAC  2947

SequencetosubmitGenbank      --------------------------------------------------
XM_007063Homosapiens         CTGTGTTTAAATTATGGATAACTCGAAAGACAGCTCAGGTGAAGGCCAGT  2997

SequencetosubmitGenbank      ------------------------------------------------
XM_007063Homosapiens         AATGATTTTTTTGAAGTTTCAATGGTGTGAAATAAATTTCTGTTCTTA    3045
```

Protein Sequence of Canine

5'3' Frame 2

```
catcttcttcatcgtggtcaatgagttctgtgaaagattttcctactatggaatgagagca  (SEQ ID NO:8)
  I  F  F  I  V  V  N  E  F  C  E  R  F  S  Y  Y  G  M  R  A   (SEQ ID NO:13)

ctcctgattctgtacttcagacggttcatcgggtgggacgataatctgtccacggccatc
 L  L  I  L  Y  F  R  R  F  I  G  W  D  D  N  L  S  T  A  I

taccacacgtttgtggctctgtgctacctgacgccgatcctcggcgcactgatcgcagac
 Y  H  T  F  V  A  L  C  Y  L  T  P  I  L  G  A  L  I  A  D

tcctggctgggaaagttcaagacaatcgtgtcactctccattgtctacacaattggacag
 S  W  L  G  K  F  K  T  I  V  S  L  S  I  V  Y  T  I  G  Q

gcggtcactgcagtaagctcaattaatgacctcacagactataacaaagatggaactcct
 A  V  T  A  V  S  S  I  N  D  L  T  D  Y  N  K  D  G  T  P

gacaatctgtccgtgcatgtggcactgtccatgattggcctggccctgatagctctggga
 D  N  L  S  V  H  V  A  L  S  M  I  G  L  A  L  I  A  L  G

actggaggaataaagccctgtgtgtctgcatttggtggagaccagtttgaagagggccag
 T  G  G  I  K  P  C  V  S  A  F  G  G  D  Q  F  E  E  G  Q

gaaaaacaaagaaacagattcttttccatcttttatttggccattaatgctggaagcttg
 E  K  Q  R  N  R  F  F  S  I  F  Y  L  A  I  N  A  G  S  L

atttccactattgtcactcccatgctcagagttcacgaatgtggaatttacagtcagaaa
 I  S  T  I  V  T  P  M  L  R  V  H  E  C  G  I  Y  S  Q  K

gcttgttacccactggcatttggggttcctgctgctctcatggccgtatctctgattgta
 A  C  Y  P  L  A  F  G  V  P  A  A  L  M  A  V  S  L  I  V

tttgtcattggcagtggaatgtacaagaagtttcagccccagggtaatgtcatgggtaaa
 F  V  I  G  S  G  M  Y  K  K  F  Q  P  Q  G  N  V  M  G  K

gttgtcaagtgcattggttttgccctcaaaaataggtttaggcaccggagtaagcagttt
 V  V  K  C  I  G  F  A  L  K  N  R  F  R  H  R  S  K  Q  F

cccaagagggagcactggctggactgggctaaagagaaatacgatgagcggctcatctct
 P  K  R  E  H  W  L  D  W  A  K  E  K  Y  D  E  R  L  I  S

caaattaagatggtcacaaaagtgatgttcttgtacatcccactcccaatgttctgggcc
 Q  I  K  M  V  T  K  V  M  F  L  Y  I  P  L  P  M  F  W  A

ctgtttgaccagcagggctccaggtggacactgcaagcaacagctatgagtgggaaaatt
 L  F  D  Q  Q  G  S  R  W  T  L  Q  A  T  A  M  S  G  K  I
```

-continued

```
ggacttcttgaagttcagccagatcagatgcagactgtgaatgccatcttgattgtcgtc
 G  L  L  E  V  Q  P  D  Q  M  Q  T  V  N  A  I  L  I  V  V

atggtccccatcatggatgccgtggtgtaccctctgattgcaaaatgtggcttcaatttc
 M  V  P  I  M  D  A  V  V  Y  P  L  I  A  K  C  G  F  N  F

acctccttgaagaggatgacagttggaatgttcctggcttccatggccttcgtgatggcg
 T  S  L  K  R  M  T  V  G  M  F  L  A  S  M  A  F  V  M  A

gcgattgttcagctggaaattgataaaactcttccagtcttccccaaacaaaatgaagtc
 A  I  V  Q  L  E  I  D  K  T  L  P  V  F  P  K  Q  N  E  V

caaatcaaagtactgaatataggaaatggtgccatgaatgtatcttttcctggagcggtg
 Q  I  K  V  L  N  I  G  N  G  A  M  N  V  S  F  P  G  A  V

gtgacagttagccaaatgagtcaatcagatggatttatgacttttgatgtagacaaactg
 V  T  V  S  Q  M  S  Q  S  D  G  F  M  T  F  D  V  D  K  L

acaagtataaacatttcttccactggatcaccagtcattccagtgacttataactttgag
 T  S  I  N  I  S  S  T  G  S  P  V  I  P  V  T  Y  N  F  E

cagggccatcgccataccctttctagtatgggcccccaataattaccgagtggtaaaggat
 Q  G  H  R  H  T  L  L  V  W  A  P  N  N  Y  R  V  V  K  D

ggccttaaccagaagccagaaaaaggagaaaatggaatcagatttataaatagtcttaat
 G  L  N  Q  K  P  E  K  G  E  N  G  I  R  F  I  N  S  L  N

gagagcctcaacatcaccatgggcgacaaagtttatgtgaatgtcaccagtcacaatgcc
 E  S  L  N  I  T  M  G  D  K  V  Y  V  N  V  T  S  H  N  A

agcgagtatcagttcttttctttgggcacaaaaaacattacaataagttcaacacaacag
 S  E  Y  Q  F  F  S  L  G  T  K  N  I  T  I  S  S  T  Q  Q

atctcacaaaattgtacaaaagttctccaatcatccaaccttgaatttggtagtgcatat
 I  S  Q  N  C  T  K  V  L  Q  S  S  N  L  E  F  G  S  A  Y

acctatgtaatcggaacgcagagcactggctgccctgaattgcatatgtttgaagatatt
 T  Y  V  I  G  T  Q  S  T  G  C  P  E  L  H  M  F  E  D  I

tcacccaacacagttaacatggctctgcagatcccgcagtacttcctcatcacctgcggc
 S  P  N  T  V  N  M  A  L  Q  I  P  Q  Y  F  L  I  T  C  G

gaggtggttttctctgtcacaggactggagttctcatattctcaggccccctccaacatg
 E  V  V  F  S  V  T  G  L  E  F  S  Y  S  Q  A  P  S  N  M

aagtcggtgcttcaggcgggatggctgctgacagtggcttgttggcaacatcattgtgct
 K  S  V  L  Q  A  G  W  L  L  T  V  A  C  W  Q  H  H  C  A

cattgtggcaggagcaggccagttcagtgaacagtgggctgaatacatcctatttgcggc
 H  C  G  R  S  R  P  V  Q  -  T  V  G  -  I  H  P  I  C  G

attgcttctggttgtctgtgtaatatttgccatcatggcccggttttacacttacgtcaa
 I  A  S  G  C  L  C  N  I  C  H  H  G  P  V  L  H  L  R  Q

tccagcagagattg
 S  S  R  D
```

5'3' Frame 2 (SEQ ID NO:13)

```
IFFIVVNEFCERFSYYGMRALLILYFRRFIGWDDNLSTAIYHTFVALCYLTPILGALIAD

SWLGKFKTIVSLSIVYTIGQAVTAVSSINDLTDYNKDGTPDNLSVHVALSMIGLALIALG

TGGIKPCVSAFGGDQFEEGQEKQRNRFFSIFYLAINAGSLISTIVTPMLRVHECGIYSQK

ACYPLAFGVPAALMAVSLIVFVIGSGMYKKFQPQGNVMGKVVKCIGFALKNRFRHRSKQF

PKREHWLDWAKEKYDERLISQIKMVTKVMFLYIPLPMFWALFDQQGSRWTLQATAMSGKI

GLLEVQPDQMQTVNAILIVVMVPIMDAVVYPLIAKCGFNFTSLKRMTVGMFLASMAFVMA

AIVQLEIDKTLPVFPKQNEVQIKVLNIGNGAMNVSFPGAVVTVSQMSQSDGFMTFDVDKL

TSINISSTGSPVIPVTYNFEQGHRHTLLVWAPNNYRVVKDGLNQKPEKGENGIRFINSLN

ESLNITMGDKVYVNVTSHNASEYQFFSLGTKNITISSTQQISQNCTKVLQSSNLEFGSAY

TYVIGTQSTGCPELHMFEDISPNTVNMALQIPQYFLITCGEVVFSVTGLEFSYSQAPSNM
```

-continued

KSVLQAGWLLTVACWQHHCAHCGRSRPVQ-TVG-IHPICGIASGCLCNICHHGPVLHLRQ

SSRD

Multiple Alignment of Amino-Acid Sequences

Sequence 1: Caninesubmitted 662 aa

Sequence 2: XM_007063HomosapiensProteinSeq 706 aa

Sequence 3: DS0306RatProteinSequence 710 aa

Sequence 4: NM_053079MusmusculusProteinSeq 709 aa

Sequence 5: AY027496Ovis 707 aa

Sequence 6: U13707OryctolaguscunicProteinS 707 aa

Sequence 7: AY029615GallusgallusProteinSeq 714 aa

Start of Pairwise alignments

Aligning . . .

Sequences (1:2) Aligned. Score: 76

Sequences (2:3) Aligned. Score: 84

Sequences (3:4) Aligned. Score: 91

Sequences (4:5) Aligned. Score: 80

Sequences (1:3) Aligned. Score: 77

Sequences (2:4) Aligned. Score: 83

Sequences (3:5) Aligned. Score: 82

Sequences (4:6) Aligned. Score: 76

Sequences (1:4) Aligned. Score: 75

Sequences (2:5) Aligned. Score: 82

Sequences (3:6) Aligned. Score: 77

Sequences (4:7) Aligned. Score: 63

Sequences (1:5) Aligned. Score: 77

Sequences (2:6) Aligned. Score: 80

Sequences (1:6) Aligned. Score: 72

Sequences (3:7) Aligned. Score: 64

Sequences (5:6) Aligned. Score: 77

Sequences (1:7) Aligned. Score: 60

Sequences (2:7) Aligned. Score: 63

Sequences (6:7) Aligned. Score: 61

Sequences (5:7) Aligned. Score: 64

Guide tree file created:

[/net/nfs0/vol1/production/w3nobody/tmp/936042.678539-441485.dnd]

Start of Multiple Alignment

There are 6 groups

Aligning. . .

Group 1: Sequences: 2 Score:14016

Group 2: Sequences: 2 Score:14858

-continued

Group 3: Sequences: 4 Score:13893

Group 4: Sequences: 5 Score:14022

Group 5: Sequences: 6 Score:12718

Group 6: Sequences: 7 Score:12338

Alignment Score 68091

CLUSTAL-Alignment file created

[/net/nfs0/vol1/production/w3nobody/tmp/936042.678539-441485.aln]

Your Multiple Sequence Alignment:

936042.678539-441485.aln

CLUSTAL W (1.81) multiple sequence alignment

```
                                                                                       (SEQ ID NO:14)
XM_007063HomosapiensProteinSeq  ---MSKSHS-----FFGYPLSIFFIVVNEFCERFSYYGMRAILILYFTNF  42

                                                                                       (SEQ ID NO:18)
U13707OryctolaguscunicProteinS  -MGMSKSLS-----CFGYPLSIFFIVVNEFCERFSYYGMRALLILYFRNF  44

                                                                                       (SEQ ID NO:15)
D50306RatProteinSequence        -MGMSKSRG-----CFGYPLSIFFIVVNEFCERFSYYGMRALLVLYFRNF  44

                                                                                       (SEQ ID NO:16)
NM_053079MusmusculusProteinSeq  -MGMSKSRG-----CFGYPLSIFFIVVNEFCERFSYYGMRALLVLYFRNF  44

                                                                                       (SEQ ID NO:17)
AY027496Ovis                    -MGMSVPKS-----CFGYPLSIFFIVVNEFCERFSYYGMRALLILYFQRF  44

                                                                                       (SEQ ID NO:13)
Caninesubmitted                 --------------------IFFIVVNEFCERFSYYGMRALLILYFRRF  29

                                                                                       (SEQ ID NO:19)
Ay029615GallusgallusProteinSeq  MAAKSKSKGRSVPNCFGYPLSIFFIVINEFCERFSYYGMRAVLVLYFKYF  50
                                                     *****:*             :*:*

XM_007063HomosapiensProteinSeq  ISWDDNLSTAIYHTFVALCYLTPILGALIADSWLGKFKTIVSLSIVYTIG  92
U13707OryctolaguscunicProteinS  IGWDDNLSTVIYHTFVALCYLTPILGALIADAWLGKFKTIVWLSIVYTIG  94
D50306RatProteinSequence        LGWDDDLSTAIYHTFVALCYLTPILGALIADSWLGKFKTIVSLSIVYTIG  94
NM_053079MusmusculusProteinSeq  LGWDDNLSTAIYHTFVALCYLTPILGALIADSWLGKFKTIVSLSIVYTIG  94
AY027496Ovis                    LGWNDNLGTAIYHTFVALCYLTPILGALIADSWLGKFKTIVSLSIVYTIG  94
Caninesubmitted                 IGWDDNLSTAIYHTFVALCYLTPILGALIADSWLGKFKTIVSLSIVYTIG  79
AY029615GallusgallusProteinSeq  LRWDDNFSTATYHIFVALCYLTPILGALIADSWLGKFKTIVSLSIVYTIG  100
                                : *:*::.*.*********************:********* ********

XM_007063HomosapiensProteinSeq  QAVTSVSSINDLTDHNHDGTPDSLPVHVVLSLIGLALIALGTGGIKPCVS  142
U13707OryctolaguscunicProteinS  QAVTSLSSVNELTDNNHDGTPDSLPVHVAVCMIGLLLIALGTGGIKPCVS  144
D50306RatProteinSequence        QAVTSVSSINDLTDHDHDGSPNNLPLHVALSMIGLALIALGTGGIKPCVS  144
NM_053079MusmusculusProteinSeq  QAVISVSSINDLTDHDHNGSPDSLPVHVALSMVGLALIALGTGGIKPCVS  144
AY027496Ovis                    QVVTAVSSINDLTDFNHDGTPNNISVHVALSMIGLVLIALGTGGIKPCVS  144
Caninesubmitted                 QAVTAVSSTNDLTDYNKDGTPDNLSVHLALSMIGLALIALGTGGIKPCVS  129
AY029615GallusgallusProteinSeq  QAVMAVSSINDMTDQNRDGNPDNIAVHIALSMTGLILIALGTGGIKPCVS  150
                                *.* ::**:*::** :::*.*:.:.:*:.:.: ** **************

XM_007063HomosapiensProteinSeq  AFGGDQFEEGQEKQRNRFFSIFYLAINAGSLLSTIITPMLRVQQCGIHSK  192
U13707OryctolaguscunicProteinS  AFGGDQFEEGQEKQRNRFFSTFYLAINAGSLLSTIITPMLRVQQCGIHSK  194
D50306RatProteinSequence        AFGGDQFEEGQEKQRNRFFSIFYLAINAGSLLSTIITPILRVQQCGIHSQ  194
NM_053079MusmusculusProteinSeq  AFGGDQFEEGQEKQRNRFFSIFYLAINGGSLLSTIITPILRVQQCGIHSQ  194
AY027496Ovis                    AFGGDQFEEGQEKQRNRFFSIFYLAINAGSLLSTIITPMLRVQVCGIHSK  194
Caninesubmitted                 AFGGDQFEEGQEKQRNRFFSTFYLAINAGSLISTIVTPMLRVHECGIYSQ  179
AY029615GallusgallusProteinSeq  AFGGDQFEEHQEKQRSRFFSIFYLSINAGSLISTIITPILRAQECGIHSR  200
                                ********* *****.********:**.***:***:**::*.: ***: :

XM_007063HomosapiensProteinSeq  QACYPLAFGVPAALMAVALTVFVLGSGMYKKFKPQGNIMGKVAKCIGFAI  242
U13707OryctolaguscunicProteinS  QACYPLAFGIPAILMAVSLIVFIIGSGMYKKFKPQGNILSKVVKCICFAI  244
D50306RatProteinSequence        QACYPLAFGVPAALMAVALIVFVLGSGMYKKFQPGNIMGKVAKRCIGFAI  244
NM_053079MusmusculusProteinSeq  QACYPLAFGVPAALMAVALIVFVLGSGMYKKFQPQGNIMGKVAKCIGFAI  244
AY027496Ovis                    QACYPLAFGVPAALMAVSLIVEVIGSGMYKKFQPGNIMSKVARKCIGFAI  244
Caninesubmitted                 KACYPLAFGVPAALMAVSLIVFVIGSGMYKKFQPQGNVMGKVVKCIGFAL  229
AY029615GallusgallusProteinSeq  QQCYPLAFGVPAALMAVSLVVFIAGSGMYKKVQPQGNIMVRVCKCIGFAI  250
                                : *******:** ****:*:**: *******.:****:: :* :** **:

XM_007063HomosapiensProteinSeq  KNRFRHRSKAFPKREHWLDWAKEKYDERLISQIKMVTRVMFLYIPLPMFW  292
```

-continued

```
U13707OryctolaguscunicProteinS  KNRFRHRSKQFPKRAHWLDWAKEKYDERLIAQIKMVTRVLFLYIPLPMFW  294
D50306RatProteinSequence        KNRFRHRSKAFPKREHWLDWAKEKYDERLISQIKMVTKVMFLYIPLPMFW  294
NM_053079MusmusculusProteinSeq  KNRFRHRSKAYPKREHWLDWAKEKYDERLISQIKMVTKVMFLFIPLPMFW  294
AY027496Ovis                    KNRISHRSKKFPKREHWLDWASEKYDERLISQIKMVTRVMFLYIPLPMFW  294
Caninesubmitted                 KNRFRHRSKQFPKREHWLDWAKEKYDERLISQIKMVTKVMFLYIPLPMFW  279
AY029615GallusgallusProteinSeq  KNRFRHRSKEYPKREHWLDWASEKYDKRLIAQTKMVLKVLFLYIPLPMFW  300
                                ***: **** :*** ******.****:***:* *** :*:**:*******

XM_007063HomosapiensProteinSeq  ALFDQQGSRWTLQATTMSGKTGALEIQPDQMQTVNAILIVIMVPIFDAVL  342
U13707OryctolaguscunicProteinS  ALFDQQGSRWTLQATTMSGRIGILEIQPDQMQTVNTILIIILVPIMDAVV  344
D50306RatProteinSequence        ALFDQQGSRWTLQATTMTGKIGTTEIQPDQMQTVNAILIVIMVPIVDAVV  344
NM_053079MusmusculusProteinSeq  GLFDQQGSRWTLQATTMNGKIGANEIQPDQMQTVNAILNVNNGPNVDAVV  344
AY027496Ovis                    ALFDQQGSRWTLQATTMSGKIGIIEIQPDQMQTVNAILIVVMVPIVDAVV  344
Caninesubmitted                 ALFDQQGSRWTLQATANSGKIGLLEVQPDQMQTVNAILIVVMVPIMDAVV  329
AY029615GallusgallusProteinSeq  ALFDQQGSRWTLQATTMDGDFGAMQIQPDQMQTVNPILIIIMVPVVDAVI  350
                                .*************:* * :*  ::*********.** :   * .***:

XM_007063HomosapiensProteinSeq  YPLTAKCGFNFTSLKKMAVGMVLASMAFVVAAIVQVEIDKTLPVFPKGNE  392
U13707OryctolaguscunicProteinS  YPLIAKCGLNFTSLKKMTIGMFLASMAFVAAAILQVEIDKTLPVFPKANE  394
D50306RatProteinSequence        YPLIAKCGFNFTSLKKMTVGMFLASMAFVVAAIVQVEIDKTLPVFPSGNQ  394
NM_053079MusmusculusProteinSeq  YRSTAKCGFNFTSLKKMTVGMFLASMAFVVAAIVQVWIDKTLPVEPGGNQ  394
AY027496Ovis                    YPLIAKCGLNFTSLKKMTVGMFLASMAFVAAAIVQVDIDKTLPVFPKGNE  394
Caninesubmitted                 YPLIAKCGFNFTSLKRMTVGMFLASMAFVMAAIVQLEIDKTLPVFPKQNE  379
AY029615GallusgallusProteinSeq  YPLIQKCKINFTPLRRITVGMFLAGLAFVAAALLQVQIDKTLPVFPAAGQ  400
                                *  * ** :***.*:::::**.**.:*** **::*::*********  .:

XM_007063HomosapiensProteinSeq  VQIKVLNIGNNTMNISLPG--EMVTLGPMSQTNAFMTFDVNKLTRINISS  440
U13707OryctolaguscunicProteinS  VQIKVLNVGSENMIISLPG--QTVTLNQMSQTNEFMTFNEDTLTSINITS  442
D50306RatProteinSequence        VQIKVLNIGNNDMAVYFPG--KNVTVAQMSQTDTFMTFDVDQLTSINVSS  442
NM_053079MusmusculusProteinSeq  VQIKVLNIGNNNMTVHFPG--NSVTLAQMSQTDTFMTFDIDKLTSINISS  442
AY027496Ovis                    VQIKVLNIGNNSMTVSFPG--TTVTCDQMSQTNGFLTFNVDNLS-INISS  441
Caninesubmitted                 VQIKVLNIGNGAMNVSFPG--AVVTVSQMSQSDGFMTFDVDKLTSINISS  427
AY029615GallusgallusProteinSeq  AQIKTINLGDSNANVTFLPNLQNVTVLPMESTG-YRMFESSQLKSVMVNF  449
                                .***::*:*.    : :      **    *..:. :  *: . *. : :.

XM_007063HomosapiensProteinSeq  PGSP-VTAVTDDFKQGQRHTLLVWAPNHYQVVK-DGLNQKPEKGENGIRF  488
U13707OryctolaguscunicProteins  -GSQ-VTMITPSLEAGQRHTLLVWAPNNYRVVN-DGLTQKSDKGENGIRF  489
D50306RatProteinSequence        PGSPGVTTVAHEFEPGHRHTLLVWGPNLYRVVK-DGLNQKPEKGENGIRF  491
NM_053079MusmusculusProteinSeq  SGSPGVTTVAHDFEQGHRHNLLVWEPSQYRVVK-DGPNQKPEKGRNGIRF  491
AY027496Ovis                    TGTP-VTPVTHNFESGHRHTLLVWAPSNYQVVK-DGLNQKPEKGRNGIRF  489
Caninesubmitted                 TGSP-VIPVTYNFEQGHRHTLLVWAPNNYRVVK-DGLNQKPEKGENGIRF  475
AY029615GallusgallusProteinSeq  GSESRSENTDSISSNTHTVTTKNAAAGIVSSLRSDNFTSKPEEGKNLVRF  499
                                 .      :    .  :  .:    ..    :. *. ..*.::*.* :**

XM_007063HomosapiensProteinSeq  VNTFNELTTITMSGKVYANISSYNASTYQFFPSGIKGFTISSTE-IPPQC  537
U13707OryctolaguscunicProteinS  VNTYSQPTNVTMSGKVYEHIASYNASEYQFFTSGVKGFTVSSAG-ISEQC  538
D50306RatProteinSequence        VSTLNEMITTKMSGKVYENVTSHSASNYQFFPSGQKDYTINTTE-IAPNC  540
NM_053079MusmusculusProteinSeq  VNTLNEMVTNKMSGKVYEKFTSHNASGYKFLPSGEKQYTINTTA-VAPTC  540
AY027496Ovis                    VNAFGESFGVTMDGEVYNNVSGHNASEYLFFSSGVKSFTINSPE-ISQQC  538
Caninesubmitted                 INSLNESLNITMGDKVYVNVTSHNASEYQFFSLGTKNITISSTQQISQNC  525
AY029615GallusgallusProteinSeq  VNNLPQTVNITMGDTTFGILEETSISNYSPFSGGRTYDIVITAG--STNC  547
                                :.   : .  .*.. .:  .   . * *  :. * .   : :.   .  *

XM_007063HomosapiensProteinSeq  QPNFNTFYLEFGSAYTYTVQ-RKNDSCPEVKVFEDISANTVNMALQIPQY  586
U13707OryctolaguscunicProteinS  RRDFESPYLEFGSAYTYLIT-SQATGCPQVTEFEDIPPNTMNMAWQIPQY  587
D50306RatProteinSequence        SSDFKSSNLDFGSAYTYVVTRSRASDGCLEVKEFEDIPPNTVNMALQIPQY  590
NM_053079MusmusculusProteinSeq  LTDFKSSNLDFGSAYTYVIR-RASDGCLEVKEFEDIPPNTVNMALQIPQY  589
AY027496Ovis                    EKQFKTSYLEFGSAFTYVIS-RKSDGCPEPKIFEDISPNTVSMALQIPQY  587
Caninesubmitted                 TKVLQSSNLEFGSAYTYVIG-TQSTGCPELHMFEDISPNTVNMALQIPQY  574
AY029615GallusgallusProteinSeq  KP--TSEKLGYGGAYTTVTN-ECSGDCTQLRYIEDIQPNTVHMAWQIPQY  594
                                     :  * :*.*:* ::      .  :   :*** .**: ** *****

XM_007063HomosapiensProteinSeq  FLLTCGEVVFSVTGLEFSYSQAPSNMKSVLQAGWLLTVAVGNIIVLIVAG  636
U13707OryctolaguscunicProteinS  FLITSGEVVFSITGLEFSYSQAPSNMKSVLQDRWLLTVAVGNIIVLIVAG  637
D50306RatProteinSequence        FLLTCGEVVFSVTGLEFSYSQAPSNMKSVLQAGWLLTVAIGNIIVLIVAE  640
NM_053079MusmusculusProteinSeq  FLLTCGEVVFSVTGLEFSYSQAPSNMKSVLQAGWLLTVAIGNIIVLIVAG  639
AY027496Ovis                    FLLTCGEVVFSITGLEFSYSQAPSNMKSVLQAGWLLTVAVGNIIVLIVAG  637
Caninesubmitted                 FLITCGEVVFSVTGLEFSYSQAPSNMKSVLQAGWLLTVACWQHHCAHCGR  624
AY029615GallusgallusProteinSeq  FILTCCEVVFSVTGLEFSYSQAPSNMKSVLQAGWLLTVAVGNIIVLIVAG  644
                                *::*.******:*******************  ******  :       .

XM_007063HomosapiensProteinSeq  AGQFSKQWAEYILFAALLLVVCVIFAIMARFYTYINPAEIEAQFDEDEKK  686
U13707OryctolaguscunicProteinS  AGQINKQWAEYILFAALLLVVCVIFAIMARFYTYVNPAEIEAQFEEDEKK  687
D50306RatProteinSequence        AGHFDKQWAEYVLFASLLLVVCIIFAIMARFYTYINPAEIEAQFDEDEKK  690
NM_053079MusmusculusProteinSeq  AGHFPKQWAEYILFASLLLVVCVIFAIMARFYTYINPAEIEAQFDEDEKK  689
AY027496Ovis                    AGQFPKQWAEYVLFAALLLVVCIIFAIMARFYTYVNPAEIEAQFDEDDKE  687
Caninesubmitted                 SRPVQ-TVG-----------IHPICGIASGCLCNICHHGPVLHLRQSSRD  662
AY029615GallusgallusProteinSeq  ASKLSEQWAEYVLFAALLFAVCIIFAVMAYFYTYTDPNEVEAQLDEEEKK  694
                                :  .    .            :  * .: :             :: :..:.
```

-continued

```
XM_007063HomosapiensProteinSeq  NRLEKSNPYFMSGANSQKQM                     706
U13707OryctolaguscunicProteinS  KNPEKNDLYPSVAPVSQTQM                     707
D50306RatProteinSequence        KGVGKENPYSSLEPVSQTNM                     710
NM_053079MusmusculusProteinSeq  KGIGKENPYSSLEPVSQTQM                     709
AY027496Ovis                    DDLEKSNPYAKLDFVSQTQM                     707
Caninesubmitted                 --------------------
AY029615GallusgallusProteinSeq  KQIKQDPDLHGKESEAVSQM                     714
```

Alignment of Amino-Acid Sequences for Canine and Human

Sequence format is Pearson

Sequence 1: XM_007063HomosapiensProteinSeq 706 aa

Sequence 2: Caninesubmittedclone37 662 aa

Start of Pairwise alignments

Aligning. . .

Sequences (1:2) Aligned. Score: 76

Guide tree file created:

[/net/nfs0/vol1/production/w3nobody/tmp/789481.229198-238519.dnd]

Start of Multiple Alignment

There are 1 groups

Aligning. . .

Group 1: Sequences: 2 Score:12826

Alignment Score 3129

CLUSTAL-Alignment file created

[/net/nfs0/vol1/production/w3nobody/tmp/789481.229198-238519.aln]

Your Multiple Sequence Alignment:

789481.229198-238519.aln

CLUSTAL W (1.81) multiple sequence alignment

```
                                                                                   (SEQ ID NO:14)
XM_007063HomosapiensProteinSeq  MSKSHSFFGYPLSIFFIVVNEFCERFSYYGMRAILILYFTNFISWDDNLS 50

                                                                                   (SEQ ID NO:13)
Caninesubmittedclone37          -------------IFFIVVNEFCERFSYYGMRALLILYFRRFIGWDDNLS 37
                                             ********************:***** .**.******

XM_007063HomosapiensProteinSeq  TAIYHTFVALCYLTPILGALIADSWLGKFKTIVSLSIVYTIGQAVTSVSS 100
Caninesubmittedclone37          TAIYHTFVALCYLTPILGALIADSWLGKFKTIVSLSIVYTIGQAVTAVSS 87
                                **********************************************:***

XM_007063HomosapiensProteinSeq  INDLTDHNHDGTPDSLPVHVVLSLIGLALIALGTGGIKPCVSAFGGDQFE 150
Caninesubmittedclone37          INDLTDYNKDGTPDNLSVHVALSMIGLALIALGTGGIKPCVSAFGGDQFE 137
                                ******:*:*****.*.***.**:**************************

XM_007063HomosapiensProteinSeq  EGQEKQRNRFFSIFYLAINAGSLLSTIITPMLRVQQCGIHSKQACYPLAF 200
Caninesubmittedclone37          EGQEKQRNRFFSIFYLAINAGSLISTIVTPMLRVHECGIYSQKACYPLAF 187
                                ***********************:***:******::***:*::*******

XM_007063HomosapiensProteinSeq  GVPAALMAVALIVFVLGSGMYKKFKPQGNIMGKVAKCIGFAIKNRFRHRS 250
Caninesubmittedclone37          GVPAALMAVSLIVFVIGSGMYKKFQPQGNVMGKVVKCIGFALKNRFRHRS 237
                                *********:*****:********:****:****.******:********

XM_007063HomosapiensProteinSeq  KAFPKREHWLDWAKEKYDERLISQIKMVTRVMFLYIPLPMFWALFDQQGS 300
Caninesubmittedclone37          KQFPKREHWLDWAKEKYDERLISQIKMVTKVMFLYIPLPMFWALFDQQGS 287
                                * ***************************:********************

XM_007063HomosapiensProteinSeq  RWTLQATTMSGKIGALEIQPDQMQTVNAILIVIMVPIFDAVLYPLIAKCG 350
Caninesubmittedclone37          RWTLQATAMSGKIGLLEVQPDQMQTVNAILIVVMVPIMDAVVYPLIAKCG 337
                                *******:****** **:**************:****:***:********

XM_007063HomosapiensProteinSeq  FNFTSLKKMAVGMVLASMAFVVAAIVQVEIDKTLPVFPKGNEVQIKVLNI 400
Caninesubmittedclone37          FNFTSLKRMTVGMFLASMAFVMAAIVQLEIDKTLPVFPKQNEVQIKVLNI 387
```

-continued

```
                                      *******:*:***.*******:*****:*********** **********

XM_007063HomosapiensProteinSeq        GNNTMNISLPGEMVTLGPMSQTNAFMTFDVNKLTRINISSPGSPVTAVTD  450
Caninesubmittedclone37                GNGAMNVSFPGAVVTVSQMSQSDGFMTFDVDKLTSINISSTGSPVIPVTY  437
                                      **.:**:*:** :**:. ***::.*****:*** *****.**** .**

XM_007063HomosapiensProteinSeq        DFKQGQRHTLLVWAPNHYQVVKDGLNQKPEKGENGIRFVNTFNELITITM  500
Caninesubmittedclone37                NFEQGHRHTLLVWAPNNYRVVKDGLNQKPEKGENGIRFINSLNESLNITM  487
                                      :*:**:*********:*:*****************:*::** :.***

XM_007063HomosapiensProteinSeq        SGKVYANISSYNASTYQFFPSGIKGFTISST-EIPPQCQPNFNTFYLEFG  549
Caninesubmittedclone37                GDKVYVNVTSHNASEYQFFSLGTKNITISSTQQISQNCTKVLQSSNLEFG  537
                                      ..***.*::*:*** ****. * *.:***** :*. :*   :::  ****

XM_007063HomosapiensProteinSeq        SAYTYIVQRKNDSCPEVKVFEDISANTVNMALQIPQYFLLTCGEVVFSVT  599
Caninesubmittedclone37                SAYTYVIGTQSTGCPELHMFEDISPNTVNMALQIPQYFLITCGEVVFSVT  587
                                      *****::  :. .***:::*****.*************:**********

XM_007063HomosapiensProteinSeq        GLEFSYSQAPSNMKSVLQAGWLLTVAVGNIIVLIVAGAGQFSKQWAEYIL  649
Caninesubmittedclone37                GLEFSYSQAPSNMKSVLQAGWLLTVACWQHHCAHCGRSRPVQ-TVG----  632
                                      **************************  :      . :  ..   .

XM_007063HomosapiensProteinSeq        FAALLLVVCVIFAIMARFYTYINPAEIEAQFDEDEKKNRLEKSNPYFMSG  699
Caninesubmittedclone37                -------IHPICGIASGCLCNICHHGPVLHLRQSSRD-------------  662
                                             :  * .* :     *       :: :..:.

XM_007063HomosapiensProteinSeq        ANSQKQM                                             706
Caninesubmittedclone37                -------
```

After analyzing the protein sequence and performing alignment with other species, the underlined, italicized was removed for submission to Genbank.

Sequence to Submit to Genbank (SEQ ID NO:7)

catcttcttcatcgtggtcaatgagttctgtgaaa gattttcctactatggaat-
gagagca ctcctgattctgtacttcagacgg ttcatcgggtgggacgataatct-
gtcca cggccatctaccacacgtttgtggctct gtgctacctgacgccgatc-
ctcggc gcactgatcgcagactcctggctgggaa
agttcaagacaatcgtgtcactct ccattgtctacacaattggacaggcggtc act-
gcagtaagctcaattaatga cctcacagactataacaaagatgg aactcctga-
caatctgtccgtgcatgtggcactgt ccatgattggcctggccctgatag ctctgg-
gaaactggaggaataaag ccctgtgtgtctgcatttggtggagaccagtttg
aagagggccaggaaaaacaaag aaacagattcttttccatcttttattt ggccat-
taatgctggaagcttgatttccacctattg tcactcccatgctcagagttcacgaat
gtggaatttacagtcagaaagcttgtt acccactggcatttggggttcctgctgct
ctcatggccgtatctctgattgtattt gtcattggcagtggaatgtacaagaag
tttcagccccagggtaatgtcatgggtaa agttgtcaagtgcattggttttgccct
caaaaataggtttaggcaccggagtaa gcagtttcccaagagggagcactggct
ggactgggctaaagagaaatacgatga gcggctcatctctcaaattaagatggt
cacaaaagtgatgttcttgtacatccc actcccaatgttctgggccctgtttga
ccagcagggctccaggtggacactgc aagcaacagctatgagtgggaaaattg
gacttcttgaagttcagccagatc agatgcagactgtgaatgccatcttgat-
tgtcgtcatggtccccatcatggatgccgt ggtgtaccctctgattgcaaaatgt
ggcttcaatttcacctccttgaaga ggatgacagttggaatgttcctggcttccatgg
ccttcgtgatggcggcgattgttca gctggaaattgataaaactcttcc agtcttc-
cccaaacaaaatgaagtccaaatcaa agtactgaatataggaaatggtgcc
atgaatgtatcttttcctggagcgg tggtgacagttagccaaatgagtcaatcagat
ggatttatgacttttgatgtagaca aactgacaagtataaacatttcttcc actggat-
caccagtcattccagtgacttataact ttgagcagggccatcgccatacccttct
agtatgggcccccaataattaccgagt ggtaaaggatggccttaaccagaag
ccagaaaaaggagaaaatggaatcaga tttataaatagtcttaatgagagcctc
aacatcaccatgggcgacaaagtttat gtgaatgtcaccagtcacaatgccag
cgagtatcagttcttttctttgggcac aaaaaacattacaataagttcaacacaac
agatctcacaaaattgtacaaaagttct ccaatcatccaaccttgaatttggtagt
gcatatacctatgtaatcggaacgcag agcactggctgccctgaattgcatatgttt
gaagatatttcacccaacacagttaa catggctctgcagatcccgcagtactt cct-
catcacctgcggcgaggtggtttt ctctgtcacaggactggagttct catattct-
caggccccctccaacatgaagtcg gtgcttcaggcgggatggctgctga-
cagtggcts Canine PepT1 Nucleotide Sequence (SEQ ID NO:20)

atgggcatgtccaagtcatatggttgc tttggttaccccttgagcatcttcttcat
cgtggtcaatgagttctgtgaaagatttt cctactatggaatgagagcactcctgatt
ctgtacttcagacggttcatcgggt gggacgataatctgtccacggccatcta
ccacacgtttgtggctctgtgctacct gacgccgatcctcggcgcactgat cgca-
gactcctggctgggaaagttcaaga caatcgtgtcactctccattgtct acacaat-
tggacaggcggtcact gcagtaagctcaattaatgacctcacagactataa caaa-
gatggaactcctgacaatct gtccgtgcatgtggcactgtccat
gattggcctggccctgatagctctgggaactgg aggaataaagccctgtgtgtctg
catttggtggagaccagtttgaa gagggccaggaaaaacaaagaaacagat-
tctttt ccatcttttatttggccattaatgctgg aagcttgatttccactattgtcactccc
atgctcagagttcacgaatgtggaatttac agtcagaaagcttgttacccactggca
tttggggttcctgctgctctcatggcc gtatctctgattgtatttgtcattggcagt
ggaatgtacaagaagtttcagcccca gggtaatgtcatgggtaaagttgtca agt-
gcattggttttgccctcaaaaataggt ttaggcaccggagtaagcagtttcccaag
agggagcactggctggactgggctaaa gagaaatacgatgagcggctca
tctctcaaattaagatggtcacaaaagt gatgttcttgtacatcccactcccaatg
ttctgggccctgtttgaccagcagggc tccaggtggacactgcaagcaacagctat
gagtgggaaaattggacttcttgaagtt cagccagatcagatgcagactgt gaat-
gccatcttgattgtcgtcatggt cccatcatggatgccgtggtgtaccc tctGattg-
caaaatgtggcttcaatttca cctccttgaagaggatgacagttggaat gttcctg-
gcttccatggccttcgtgat ggcggcgattgttcagctggaaattga
taaaactcttccagtcttccccaaac aaaatgaagtccaaatcaaagtactg aatat-
aggaaatggtgccatgaatgtatctt ttcctggagcggtggtgacagttagcc
aaatgagtcaatcagatggatttatga cttttgatgtagacaaactgacaagtat
aaacatttcttccactggatcaccagt cattccagtgacttataactttgagc
agggccatcgccatacccttctagtatggg cccccaataattaccgagtggtaaa
ggatggccttaaccagaagccagaa aaaggagaaaatggaatcagatttataaat
agtcttaatgagagcctcaacatca ccatgggcgacaaagtttatgtg aatgtcac-
cagtcacaatgccagcgagtatcag ttctttctttgggcacaaaaaaca tta-
caataagttcaacacaacaga tctcacaaaattgtacaaaagttctccaatcatcc
aaccttgaatttggtagtgcatat acctatgtaatcggaacgcagag cactggct-
gccctgaattgcatatgtttgaagatat ttcacccaacacagttaacat ggctctg-
cagatcccgcagtactt cctcatcacctgcggcgaggtggttttctctgtcaca
ggactggagttatcatattctca ggccccctccaacatgaagtcggt gcttcag-
gcgggatggctgctgacagtggctgtt ggcaacatcattgtgctcattgtg gcag-
gagcaggccagttcagtgaa cagtgggctgaatacatcctatttgcggcattg
cttctggttgtctgtgtaatattt gccatcatggcccggttttacactt acgtcaatc-
cagcagagattgaagctcagtttgacg acgatgagaaaaagaacctggaaaa
gatgaatgtatattccacggtaactccggtctcacagacacagatg Canine PepT1 Amino Acid Sequence (SEQ ID NO:21)

MGMSKSYGCFGYPLSIFFIVVNEF CERFSYYGMRAL-LILYFRRFIGWDDNLS TAIYHTFVALCYLTPILGALI-ADS WLGKFKTIVSLSIVYTIGQAVTAVSSINDL TDYNKDGTPDNLSVHVALSMIG LALIALGTGGIK-PCVSAFGGDQFEEGQEK QRNRFFSIFYLAIN-AGSLISTI VTPMLRVHECGIYSQKACYPLAFGV-PAALMA VSLIVFVIGSGMYKKFQPQGN VMGKVVKCIGFALKNRFRHRSKQFPKREH WLD-WAKEKYDERLISQIKMV TKVMFLYIPLPMF-WALFDQQGSRWTLQATA MSGKIGLLEVQPDQM-QTVNAI LIVVMVPIMDAVVYPLIAKCGFNFTSLKRM TVGMFLASMAFVMAAIVQL EIDKTLPVFPKQNEV-QIK VLNIGNGAMNVSFP GAVVTVSQMSQSDG-FMIFDVDKLTS INISSTGSPVIPVTYNFEQGHRHTLLV WAPNNYRVVKDGLNQKPEKGENG IRFINSL-NESLNITMGDKVYVNVTSHN ASEYQFFSLGT-KNITISSTQQIS QNCTKVLQSSNLEFGSAY-TYVIGTQSTGCPE LHMFEDISPNTVNMALQIPQYFLI TCGEVVFSVTGLEFSYSQAPSNMKSVLQ AGWLLTVAVGNIIVLIVAGAGQF SEQWAEYIL-FAALLLVVCVIFAIMARFYT YVNPAEIEAQFDDDE-KKNLEKMNVYSTVTPVSQTQM

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

What is claimed is:

1. A method for determining canine PepT1-transportability of a peptide comprising:

(a) providing an immortalized kidney distal tubule epithelial (Madin-Darby Canine Kidney (MDCK)) cell and a peptide having about 2 to about 4 amino acids, and (b) determining the amount of the peptide transported into the cell, wherein the amount correlates with the canine PepT1-transportability of the peptide.

2. A method for identifying a peptide with a beneficial nutritional property for an animal comprising:

(a) providing an immortalized kidney distal tubule epithelial (Madin-Darby Canine Kidney (MDCK)) cell and a peptide having about 2 to about 4 amino acids, and (b) determining the amount of the peptide transported into the cell, wherein the amount correlates with the beneficial nutritional property.

3. The method of claim 1 or 2, which further comprises the step of incubating the MDCK cell in medium containing lactalbumin hydrolysate prior to determining the amount of peptide transport into the cell.

4. The method claim 1 or 2, wherein the peptide is a dipeptide, tripeptide, or tetrapeptide.

5. The method claim 1 or 2, wherein the cell is in medium at a pH of between about 5 and 8.

6. The method of claim 1 or 2, wherein the peptide is present in a concentration of about 10 nM to about 50 mM.

7. A dietary composition for an animal comprising a peptide identified by the method of claim 1 or 2.

8. The composition of claim 7, wherein the peptide is a dipeptide, tripeptide, or tetrapeptide.

9. A dietary composition comprising at least about 10 nm of dipeptide, tripeptide, or tetrapeptide identified by the method claim 1 or 2.

10. A process for altering the absorption of essential amino acids in an animal comprising the steps of:

(a) feeding the animal a diet containing the composition of claim 9; and (b) maintaining the animal on the diet for a sufficient period of time to allow the composition to be absorbed by the digestive system of the animal.

11. The process of claim 10, wherein the animal is a dog.

12. The process of claim 10 in which the diet comprises about 20 to about 30% crude protein, about 10 to about 20% fat, and about 3 to about 10% dietary fiber.

13. A method of stimulating $H^+$-dependent peptide transport in cells comprising contacting the cells in vitro or in vivo with a PepT1 substrate.

14. The method of claim 13, wherein the PepT1 substrate is GlySar or carnosine.

15. The method of claim 13, wherein the PepT1 substrate is GlySar.

16. The method of claim 13, wherein the PepT1 substrate is carnosine.

17. The method of claim 13, wherein the PepT1 substrate is a peptide identified in claim 1 or 2.

18. The method of claim 13, wherein the contacting is carried out by administering the PepT1 substrate to an animal.

19. A composition comprising an isolated nucleic acid encoding or complementary to, a canine PepT1.

20. The composition of claim 19, wherein the nucleic acid is DNA.

21. The composition of claim 19 that hybridizes under moderate hybridization conditions to any one of SEQ ID NOS.7–9 or 20, or the complement thereof.

22. The composition of claim 19 that hybridizes under stringent hybridization conditions to any one of SEQ ID NOS:7–9 or 20, or the complement thereof.

23. The composition of claim 19, wherein the nucleic acid is SEQ ID NO:7–9 or 20.

24. The composition of claim 19, wherein the nucleic acid is RNA.

25. A peptide having an amino acid sequence encoded by the nucleic acid of SEQ ID NO:7–9 or 20.

26. A peptide having an amino acid sequence encoded by SEQ ID NO:13 or SEQ ID NO:21.

* * * * *

SEQUENCE LISTING

```
<160> NUMBER OF SEQ ID NOS: 21

<210> SEQ ID NO 1
<211> LENGTH: 3045
<212> TYPE: DNA
<213> ORGANISM: Homo sapiens

<400> SEQUENCE: 1

gaatgtccaa atcacacagt ttctttggtt atcccctgag catcttcttc atcgtggtca      60

atgagttttg cgaaagattt tcctactatg gaatgcgagc aatcctgatt ctgtacttca     120

caaatttcat cagctgggat gataacctgt ccaccgccat ctaccatacg tttgtggctc     180

tgtgctacct gacgccaatt ctcggagctc ttatcgccga ctcgtggctg ggaaagttca     240

agaccattgt gtcgctctcc attgtctaca caattggaca agcagtcacc tcagtaagct     300

ccattaatga cctcacagac cacaaccatg atggcacccc cgacagcctt cctgtgcacg     360

tggtgctgtc cttgatcggc ctggccctga tagctctcgg gactggagga atcaaaccct     420

gtgtgtctgc gtttggtgga gatcagtttg aagagggcca ggagaaacaa agaaacagat     480

ttttttccat cttttacttg gctattaatg ctggaagttt gctttccaca atcatcacac     540

ccatgctcag agttcaacaa tgtggaattc acagtaaaca agcttgttac ccactggcct     600

ttggggttcc tgctgctctc atggctgtag ccctgattgt gtttgtcctt ggcagtggga     660

tgtacaagaa gttcaagcca cagggcaaca tcatgggtaa agtggccaag tgcatcggtt     720

ttgccatcaa aaatagattt aggcatcgga gtaaggcatt tcccaagagg gagcactggc     780

tggactgggc taaagagaaa tacgatgagc ggctcatctc ccaaattaag atggttacga     840

gggtgatgtt cctgtatatt ccactcccaa tgttctgggc cttgtttgac cagcagggct     900

ccaggtggac actgcaggca acaactatgt ccgggaaaat cggagctctt gaaattcagc     960

ccgatcagat gcagaccgtg aacgccatcc tgatcgtgat catggtcccg atcttcgatg    1020

ctgtgctgta ccctctcatt gcaaaatgtg gcttcaattt cacctccttg aagaagatgg    1080

cagttggcat ggtcctggcc tccatggcct ttgtggtggc tgccatcgtg caggtggaaa    1140

tcgataaaac tcttccagtc ttccccaaag gaaacgaagt ccaaattaaa gttttgaata    1200

taggaaacaa taccatgaat atatctcttc ctggagagat ggtgacactt ggcccaatgt    1260

ctcaaacaaa tgcatttatg acttttgatg taaacaaact gacaaggata aacatttctt    1320

ctcctggatc accagtcact gctgtaactg acgacttcaa gcagggccaa cgccacacgc    1380
```

-continued

```
ttctagtgtg ggcccccaat cactaccagg tggtaaagga tggtcttaac cagaagccag   1440

aaaaagggga aaatggaatc agatttgtaa atacttttaa cgagctcatc accatcacaa   1500

tgagtgggaa agtttatgca aacatcagca gctacaatgc cagcacatac cagtttttc   1560

cttctggcat aaaaggcttc acaataagct caacagagat tccgccacaa tgtcaaccta   1620

atttcaatac tttctacctt gaatttggta gtgcttatac ctatatagtc caaaggaaga   1680

atgacagctg ccctgaagtg aaggtgtttg aagatatttc agccaacaca gttaacatgg   1740

ctctgcaaat cccgcagtat tttcttctca cctgtggcga agtggtcttc tctgtcacgg   1800

gattggaatt ctcatattct caggctcctt ccaacatgaa gtcggtgctt caggcaggat   1860

ggctgctgac cgtggctgtt ggcaacatca ttgtgctcat cgtggcaggg gcaggccagt   1920

tcagcaaaca gtgggccgag tacattctat ttgccgcgtt gcttctggtc gtctgtgtaa   1980

tttttgccat catggctcgg ttctatactt acatcaaccc agcggagatc gaagctcaat   2040

ttgatgagga tgaaaagaaa aacagactgg aaaagagtaa cccatatttc atgtcagggg   2100

ccaattcaca gaaacagatg tgaaggtcag gaggcaagtg gaggatggac tgggcccgca   2160

gatgccctga cctctgcccc caggtagcag gacactccat tggatggccc ctgatgagga   2220

agacttcaga attgggaact aaaccatgaa tgctattttc tttttcttt ttcttttctt   2280

ttttttttt ttttttttt tgagacagag ttttgctctt gttgtccagg ctggagtgca   2340

atggcacgat ctcagctcac tgcaacctcc gcctcccagg ttcaagtaat tctcctgcct   2400

cagcctcccg agtggctggg attagcggca tgcaccacca cgcccagcta tttttgtatt   2460

tttagtagag atggggtttc accatgttgg ccaggatggt ctcgatctct tgacctggtg   2520

atctgcccac ctcggcctgc caaagtgctg ggattacagg cttgagctac cgcgcccggc   2580

cgtgaacgct attttctaag cagccagcag tgaatctaaa actctggaag aagtcttctg   2640

tttgaaaggc ttatttaagc cacacgtaca cacactgtct tagagtactg tgagcccacc   2700

ccacattggt catcttccct atcacacaaa tgatgttatt ttggactagc ttaattttga   2760

aatggtaaca aagtttccta ttccatactg ttcatttcta atactcttac gaaaactatt   2820

ctaaaggagg caggagccaa ggccaaaagt gaacgtacag gtttgaaatg gctgtgataa   2880

ggaccagctg gtattaactg ataactttac ctttgggttt ttgttatttt gtttttctag   2940

tccctacctg tgtttaaatt atggataact cgaaagacag ctcaggtgaa ggccagtaat   3000

gatttttttg aagtttcaat ggtgtgaaat aaatttctgt tctta                   3045
```

<210> SEQ ID NO 2
<211> LENGTH: 2829
<212> TYPE: DNA
<213> ORGANISM: Ovis aries

<400> SEQUENCE: 2

```
gaaacaacat ctttagcacg gattcctccc acctggactc ctcgctcgcc agtcgcaggg     60

agccctcgga gccgccagca tgggaatgtc cgtgccgaag agctgcttcg gttacccctt    120

aagcatcttc ttcatcgtgg tcaatgagtt ctgcgaaagg ttctcttact atggaatgag    180

agcactcctg atcctgtact tccaacgttt cctgggctgg aacgacaacc tgggcaccgc    240

catctatcac acgttcgtcg ccctgtgcta cctgacgccc atcctcggag ctctcatcgc    300

cgactcctgg ctggggaagt tcaagacgat cgtgtcgctg tccatcgtct acaccattgg    360

gcaggtagtc atcgctgtga gctcaattaa tgacctcact gacttcaacc atgatggaac    420

cccaaacaat atttctgtgc acgtggcact ctccatgatt ggcctggtcc tgatagctct    480
```

-continued

```
gggtaccgga gggataaagc cttgcgtgtc tgcatttggc ggagatcagt ttgaagaggg    540
ccaggaaaag caaaggaaca gattttttttc catcttttat ttggccatta atgctggaag    600
tttgctttct actatcatca cccccatgct cagagttcag gtatgcggaa ttcacagtaa    660
gcaagcttgt taccccctgg cctttggggt tcctgctgca ctcatggctg tatctctgat    720
cgtgtttgtc attggcagtg gaatgtacaa gaaggtccag ccccagggta acatcatgtc    780
taaagttgcc aggtgcattg ggtttgccat caaaaatagg attagccatc ggagtaagaa    840
atttcctaag agggagcact ggctggactg ggctagcgag aaatatgatg agcggctcat    900
ctctcaaatt aagatggtta caagggtgat gttcctgtac attcctctcc ccatgttctg    960
ggccttgttt gatcagcagg gctccaggtg gacactgcaa gcaacgacca tgagtgggaa   1020
gattggaatc attgaaatcc agccggatca gatgcagacg gtgaacgcca tcctgatcgt   1080
cgtcatggtc cccatcgtgg atgccgtggt atatcctctg atcgcaaagt gtggtttaaa   1140
tttcacctcc ctgaagaaga tgaccgtcgg catgtttctg gcctccatgg ctttcgtggc   1200
agctgccatc gtgcaggtgg acattgacaa aactctgccc gtcttcccca aaggaaatga   1260
agtccaaatc aaagtcctga atataggaaa taatagcatg accgtgtctt ttcccggaac   1320
gacagtgaca tgtgaccaga tgtctcaaac aaacggattt ctgactttca acgtagacaa   1380
cctaagtata aacatttctt ctactggaac accagtcact ccagtaactc ataactttga   1440
gtccggccat cgccataccc ttctcgtctg ggccccaagt aactaccaag tggtaaaaga   1500
tggccttaac cagaagccag aaaaagggag aaatggaatc agattcgtta atgcttttgg   1560
cgagagcttc ggcgtcacaa tggatgggga agtttacaac aatgtctccg gtcacaatgc   1620
cagtgaatat cttttttttct cttctggcgt aaagagcttc acaataaact caccagagat   1680
ttcacaacag tgtgaaaaac agttcaaaac atcctacctt gaatttggta gtgcgtttac   1740
ctatgtaatc agcagaaaga gtgacggttg ccccgaacca aagattttcg aagacatctc   1800
ccccaacaca gtcagcatgg ctctgcagat cccccagtac ttcctcctca cctgtggcga   1860
ggtggtcttc tccatcaccg gcctggagtt ctcctattct caggctcctt ccaacatgaa   1920
gtcggtactt caggcaggat ggctgttgac cgtggccgtt ggcaacatca tcgtgcttat   1980
tgtggcagga gcaggccagt tcagtgaaca gtgggccgag tacgttctgt ttgcggcatt   2040
gcttctggtc gtctgcataa tatttgccat catggctcga ttctatacgt atgtcaaccc   2100
cgcagagatt gaagctcagt ttgatgagga tgacaaggag gatgacctgg aaaagagtaa   2160
cccatacgcc aagctggact tcgtctcaca gacacaaatg tgaatgtcag gaagcaagcg   2220
gacgcggggc tgggccaggg tgtgcccagg ggtctgtccc atgggggcag gacactctgt   2280
tgggtggcct ctgatgggga agacttcaga actgtggacc aaaccaagac agctgctttc   2340
tcagcagccg gcaatgaacc tgaaactcca aaagacgtcc ttttgtttgt ttgtttttag   2400
agaagtctta tttaaagcgc acacacacgc acacgcacac acatgcacac acacacactt   2460
ttataagagt ccatactctg cctgaactcc ttttcctaac acacaaataa agttattttg   2520
gactaacttg aatttttgaa atggtggcca agctccatac gtgcattcgc acactctgtg   2580
caaacaatgt taaaggaggc aaaaagtgaa tggttggggc ttttgaatag tacgtgttca   2640
taataaggac cggctggtat taactgataa ctctaccttc tgtttttagt tctgtttttc   2700
cattccctac ctctttgtaa attatggatt aacctttgaa aaaccactca ggtaaaggca   2760
agtcatgatt tttggagtct caacggtatg aaataaactc tcattctcaa gaaaaaaaaa   2820
```

-continued aaaaaaaaa 2829

<210> SEQ ID NO 3
<211> LENGTH: 2900
<212> TYPE: DNA
<213> ORGANISM: Rattus norvegicus

<400> SEQUENCE: 3
ctgaactcct gcttgccagt cgccggtcag gagcctcgga gccgccacaa tggggatgtc 60
caagtctcgg ggttgctttg gctacccatt gagcatcttc ttcatcgtgg tcaatgaatt 120
ctgtgaaaga ttctcctact atgggatgcg agctctcctg gttctgtact tcaggaactt 180
ccttggctgg gatgatgacc tctccacggc catctaccat acgtttgttg ccctctgcta 240
cctgactcca attcttggag ctctgatcgc agactcgtgg ctggggaagt tcaagacaat 300
tgtctcacta tccatcgtct acacgatcgg acaggccgtc atctcagtga gctcaattaa 360
tgaccttaca gaccatgacc acgacggcag tcctaacaac cttcctttgc acgtagcact 420
gtccatgatc ggcctggccc tgatagccct tggtacagga ggaatcaagc cctgtgtgtc 480
tgcatttggt ggcgatcagt ttgaagaggg tcaggaaaaa cagcgaaacc ggttcttttc 540
catcttttat ttggctatca acgcaggaag cctgctctcc acgatcatca ctcccatact 600
cagagttcag cagtgcggaa tccacagcca acaagcttgt tacccactgg cctttggggt 660
tccggcagct ctcatggctg ttgccctaat tgtgtttgtc ctcggcagtg gaatgtacaa 720
gaagtttcag ccccagggca acatcatggg caaagtggcc aagtgcattg gctttgccat 780
caaaaacagg tttcggcacc gaagtaaggc atttcccaag agggaacact ggctggactg 840
ggctaaagag aaatacgatg agaggctcat ctcgcagatt aagatggtga cgaaggtgat 900
gttcctgtac attcccctcc ccatgttttg ggccttgttt gaccagcagg gttccaggtg 960
gacactgcaa gcaacgacca tgactgggaa aattggaaca attgagattc agccggacca 1020
gatgcagacg gtgaacgcca tcttgattgt catcatggtc cccattgtgg acgccgtggt 1080
gtatccgctc attgcaaaat gtggtttcaa cttcacctcc ctgaagaaga tgaccgttgg 1140
gatgttcctg gcatccatgg cctttgtggt ggctgcaatt gtgcaggtgg aaatcgataa 1200
aactcttcca gtcttcccca gcggaaatca agttcaaatt aaggtcttga acattggaaa 1260
caatgacatg gccgtgtatt ttcctggaaa gaatgtgaca gttgcccaaa tgtctcagac 1320
agacacattc atgactttcg atgtagacca gctgacaagc ataaacgtgt cttctcccgg 1380
atctccaggc gtcaccacgg tagctcatga gtttgagccg ggtcaccggc acacccttct 1440
agtgtggggc cccaatctat accgtgtggt aaaagacggt cttaaccaaa agccagagaa 1500
aggggagaac ggaatcagat tcgtcagcac ccttaacgag atgatcacca tcaaaatgag 1560
tggaaaagtg tacgaaaatg tcaccagtca cagcgccagc aactatcagt tttcccttc 1620 tggccaaaaa gactacacaa taaacaccac agagattgca ccaaactgtt catctgattt 1680
taaatcttcc aaccttgact tcggcagcgc gtacacctac gtgatcagaa gtagggcgag 1740
tgatggctgc ctggaagtga aggaattcga agacatccca cccaacacgg tgaacatggc 1800
cctgcagatc ccacagtact tcctcctcac ctgcggcgag gtggtcttct ctgtcacagg 1860
actggagttc tcctattccc aggccccgtc taacatgaag tccgtgcttc aggcaggatg 1920
gcttctaacc gtggccatcg gtaatatcat tgtcctcatt gtggctgagg caggccactt 1980
cgacaaacag tgggctgagt atgttctgtt cgcctccttg ctcctggtcg tctgcatcat 2040
atttgccatt atggcccgat tctacaccta catcaaccca gcagagatcg aggcacagtt 2100

-continued cgatgaggat gagaagaaaa agggcgtagg gaaggaaaac ccgtattcct cgttggaacc 2160
tgtctcacag acaaacatgt gaagatcaga aagcaagtgg agaacatacc aagtccagca 2220
ttcaccatga cctctgccca agggacagga ccctccacca cagagtcctt gctggagaaa 2280
gacttcagac atgtgagcca aaataataac aaagcaggtt ttcaggctga cggctgtgaa 2340
tctgaaactc taggggagcc tttttaattt gtttttcttg agacaaggta tctctgtgta 2400
accctggcta tcctggaact cactctatag accaggctgg cctcgaactc acagatatct 2460
gtctgcctct gcctcctaag tactgggatt caaggcatgt acggcaactg cccagctaaa 2520
atattattta taacatgcac tttctgggtt ttttgttttt aaaacatact ttttttttta 2580
acactgggcc atttctaaca tttctgccac agaagtggat ttagctcaga ttaattttga 2640
aaaggtaaca gtactgtttt ttttccttaa tgctcttatg aaaacaatgt tgaatttaca 2700
gagggctttt ttagcagtgt gtagtgagtg tcagctgatt cgagctaata accttacctc 2760
ggggtttttg tttctttgtt ttcctggtct cctttgcctg acctcttttt aaattatgtg 2820
taattcaaaa gactattcaa gtgatggtta gtcatgagtc gtgacgtttg actggtgtga 2880
agtaaattct tgttcttaag 2900

<210> SEQ ID NO 4
<211> LENGTH: 3128
<212> TYPE: DNA
<213> ORGANISM: Mus musculus

<400> SEQUENCE: 4
gtcgcccgtc cggagccttg gagccaccac aatggggatg tccaagtctc ggggttgctt 60
cggttacccg ttgagcatct tcttcatcgt ggtcaatgaa ttctgtgaaa gattctccta 120
ctatggcatg cgagcactcc tggttctgta cttcaggaac ttcctcggct gggacgacaa 180
tctctccacg gccatttacc atacgttcgt tgccctctgc tacctgactc caattcttgg 240
agctctgatc gcagactcgt ggctggggaa gttcaagaca attgtttcac tatccatcgt 300
ctacacgatt ggacaagcag tcatctcggt gagctcaatt aatgacctca cagaccacga 360
ccacaatggc agtcctgaca gccttcccgt gcacgtagca ctgtccatgg ttggcctggc 420
cctgatagcc cttggtacag gaggaatcaa gccctgtgtg tctgcgtttg gtggcgatca 480
gtttgaagag ggtcaggaaa aacagcgaaa ccggttcttt tccatctttt atttggctat 540 caacgggggga agcctgctct ccacgatcat cactcccata ctcagagttc aacagtgcgg 600
aatccacagt caacaagctt gttacccact ggccttcggg gttccagcgg ctctcatggc 660
tgttgcccta attgtgtttg tccttggcag tggaatgtac aagaagttcc agccccaggg 720
caacatcatg ggcaaagtgg ccaagtgcat tggttttgcc atcaaaaaca ggtttcggca 780
ccgaagtaag gcatatccca agagggagca ctggctggac tgggctaaag agaaatacga 840
cgagcggctc atctcacaga ttaagatggt cacgaaggtg atgttcctgt tcatcccact 900
ccccatgttc tggggcctgt ttgaccaaca agggtccaga tggacactgc aagcaacgac 960
catgaatggg aaaattggag caaatgaaat tcagccggac cagatgcaga cggtgaatgc 1020
catcctgaat gtcaacaatg gccccaatgt ggacgccgtt gtgtaccgct caattgcaaa 1080
atgtggtttc aacttcacat ccctgaagaa gatgactgtt gggatgttcc tggcgtccat 1140
ggcctttgtg gtggctgcaa ttgtgcaggt ggaaatcgat aaaactcttc cagtcttccc 1200
tggtggaaat caagtccaaa ttaaggtctt gaacatcgga aacaataaca tgaccgtgca 1260

-continued

```
ttttcctgga aatagtgtga cgcttgccca aatgtctcag acagacacgt tcatgacttt   1320
cgatatagac aagctgacaa gcataaacat atcttcctct ggatccccag gagtcaccac   1380
agtagctcat gattttgagc agggtcaccg gcacaacctt ctagtgtggg aacccagtca   1440
ataccgtgtg gtaaaagatg gtcctaacca aaagccagag aaaggggaga acggaatcag   1500
gtttgtcaac acccttaacg agatggtcac caacaaaatg agtgggaaag tatatgaaaa   1560
attcacaagt cacaacgcca gcggctacaa gttcctccct tctggcgaaa agcagtacac   1620
aataaacacc acggcggtgg caccaacctg tctaactgat tttaaatctt ccaaccttga   1680
ctttggcagc gcgtatacct acgtgatccg aagggcgagt gatggctgcc tggaagtgaa   1740
ggaatttgaa gacatcccac ccaacactgt gaacatggct ctgcagatcc cacagtactt   1800
ccttctcacc tgcggcgagg tggtcttctc tgtcacagga ctggagttct cttattccca   1860
ggctccgtct aacatgaagt ccgtgcttca ggcaggctgg cttctaactg tggcggtcgg   1920
caatatcatt gtgctcatcg tggcaggggc ggggcacttc cccaaacagt gggctgagta   1980
cattctgttt gcctcattgc ttctggttgt ctgcgtgata ttcgccatca tggctcgatt   2040
ctacacctac atcaacccag cagagattga agcacagttt gatgaggatg agaagaaaaa   2100
gggcatagga aaggaaaacc cgtattcttc attggaacca gtctcacaga caaatatgtg   2160
aagggcagaa ggcaaattgg agaaagatca agttcaacat gagccctgac ctctgtccaa   2220
gggacaggac actccaccac agagtccctg atggagaaag acctcagaag tgtgagccag   2280
aataataaca aagcaggttt tctaaccaac agctgtgaac ctgaaactct aggggagcct   2340
tttttattta aaaaaatttt ttttttaatt ttttaaattt tttttatttt ttattttttt   2400
tgcttgtttg tttgtttcga gacagggttt ctcgtgtgta gcccttggtt gtcctggaac   2460
tcactctgta gaccagactg gcctcaaact cagaaatcca cctgcccctg cccctgcccc   2520
tgcccctgcc cctgcccctg cctctgcctc tgcctcccaa gtgctggatt tggaggcatg   2580
caccaccatg cccagctata attttttttt tttaagacag ggattctctg tataagcctg   2640
actgccctgg aacttgctct atagaccagg ctggccttga actcacagag atctgcctgc   2700
ctcttcctcc taagtactgg gatttcaggc atgcaccaca actgcccagc taaaatatta   2760
tttataatat gcactttctg gtttgttttt gtttttcttt taaactgggc tgtatcttac   2820
atttctgcca cagaaatgaa cttagctcag attaacttaa ttttgaaaag gcaatagtat   2880
tgttttttct aacagtttta tgaaaacaat attgaattta cagagggctt ttttaatagt   2940
gtgtaatgag tatcaactga ttcaagctaa ttgctttacc ttggggtttt tttgtttgtt   3000
tgtttgtttg tttgtttgtt tgtttttcta gtctcctttg ccttacctct ttttaaatta   3060
tgtgtaattc aaaagactag tcatgagttg tgaagtttca ctggtctgaa ataaattcta   3120
gttcttaa                                                            3128
```

```
<210> SEQ ID NO 5
<211> LENGTH: 2709
<212> TYPE: DNA
<213> ORGANISM: Oryctolagus cuniculus

<400> SEQUENCE: 5

caccatggga atgtctaagt cactgagctg cttcggctat cccctgagca tcttcttcat     60
cgtggtcaat gagttctgcg aaaggttctc ctactatggg atgagagcac tcctgattct    120
gtacttcaga aacttcatcg gctgggacga caacctgtcc acggtcatct accacacgtt    180
cgtcgcgctg tgctacctca cgcccattct cggagctctc atcgccgacg cgtggctggg    240
```

-continued

```
gaagttcaag accatcgtgt ggctgtccat cgtctacacc atcggacaag cagtcacctc    300
cctcagctcc gtcaatgagc tcacagacaa caaccatgac gggacccccg acagcctccc    360
tgtgcacgtg gcggtgtgca tgatcggcct gctcctgata gccctcggga caggaggaat    420
caagccctgt gtgtctgcct ttggcggcga tcagtttgag gagggccagg aaaagcaaag    480
aaaccggttt ttttccatct tttacttggc cattaacgct gggagtctgc tgtccacaat    540
catcaccccc atggtcagag ttcaacaatg tggaattcac gttaaacaag cttgctaccc    600
actggccttt gggattcctg ctatcctcat ggctgtatcc ctgatcgtgt tcatcatcgg    660
cagtgggatg tacaagaagt tcaagccgca ggggaacatc ctgagcaaag tggtgaagtg    720
catctgcttt gccatcaaaa ataggtttag gcaccgcagt aagcagtttc ccaagagggc    780
gcactggctg gactgggcta aggagaaata cgacgagcgg cttatcgcgc agatcaagat    840
ggttacgagg gtgctgttcc tgtacatccc actccccatg ttctgggcct tgtttgatca    900
gcagggttcc agatggacgc tgcaagcgac gaccatgtcc gggagaattg gaatccttga    960
aattcagccg gatcagatgc agactgtgaa caccatcttg attattatcc tggtccccat   1020
catggacgcc gtggtgtatc ctctgattgc aaagtgtggc ctcaacttca cctctctgaa   1080
gaagatgacg attgggatgt tcctggcttc catggccttc gtggcagctg caatcctgca   1140
ggtggaaatc gataaaactc ttcctgtctt ccccaaagcc aatgaagtcc aaattaaagt   1200
tctgaatgta ggaagtgaga acatgatcat ctctcttcct gggcagacgg tgacgctcaa   1260
ccagatgtct caaacgaatg aattcatgac tttcaatgaa gacacactga caagcataaa   1320
catcacttcc ggatcacaag tcaccatgat cacacccagc cttgaggcag gccagcgcca   1380
caccctgctg gtgtgggccc ccaataacta ccgagtggtc aatgacggcc tgacccagaa   1440
gtcagacaaa ggagaaaatg gaatcaggtt tgtgaacact tacagccagc ccatcaacgt   1500
cacgatgagc gggaaagttt acgaacacat cgccagctac aatgccagcg agtatcagtt   1560
tttcacttct ggagtaaagg gcttcaccgt cagctcggca ggcatctcgg agcagtgcag   1620
gcgggacttt gagtctccgt acctggagtt tggcagcgcg tacacgtacc tgatcacgag   1680
ccaggctact ggctgccccc aagtgacgga gtttgaagat attccgccca acacaatgaa   1740
catggcttgg caaatcccac agtacttcct catcacctct ggcgaggtgg tcttctccat   1800
cacgggcctg gagttctcct attctcaggc tccttccaac atgaagtcgg tgctgcagga   1860
ccggtggctg ctgacggtgg ctgtgggcaa catcattgtg ctcatcgtgg ccggcgcggg   1920
ccagatcaac aagcagtggg ccgagtacat cctctttgcc gccctgctcc tggtcgtctg   1980
tgtcatattt gccatcatgg ctcgattcta tacgtatgtc aacccggccg agatcgaggc   2040
tcagtttgaa gaagatgaga agaaaaagaa cccagaaaag aacgacctct accccctccgt   2100
ggcgcccgtc tcacagacac agatgtgagt ctggaggcgg tgtaggaggc ccacgcctgg   2160
cgtgcactgt gacctctgtc cgagggcgca ggacgtaccc ctgggcagcc ccggaagggg   2220
aggacttgag aactgtgaac cagaccacga aagctatgtt ctgagcagcc agtgatgagt   2280
ccaaaactct gaaagaaatc ttgttgaaag tcttatttaa aacacacaca cacacacaca   2340
cacacacaca cacacttttc caacactgac agcctaccca tgttaactcc ttctctacca   2400
atgcaaatgc tgttattttg gactaactta attttgaaca ctgttctatg ttgcttgtat   2460
tctaacatcc ttaggaaagg caatgttaag agaggcagga ggcaatgcca aagttgaata   2520
tgtaggtgtc agaatggtat ataccacata ttacttagta ttaactgaaa acctcaactt   2580
```

-continued

```
tgaggttttg ttctattttt tccactcctt acctcttttt aacctgtgga caactcaaaa   2640

ggaccactca gataaaggcc agtaaagatt ttttttgccg ttttgatgaa ataaaataat   2700

gttcctaag                                                           2709
```

<210> SEQ ID NO 6
<211> LENGTH: 2914
<212> TYPE: DNA
<213> ORGANISM: Gallus gallus

<400> SEQUENCE: 6

```
gctctctgtc cgtccctcgg tccctccgtc cctccgtccc cgcgcggccg ccagcagcgt     60

gccggcccca tggctgcaaa aagtaagagt aagggccgat cagtgccgaa ctgctttggc    120

taccccttga gcatcttctt catcgtcatc aatgagttct gcgagaggtt ctcctactat    180

ggcatgcgag ctgtgctcgt attgtatttc aagtacttcc tgcggtggga tgacaacttt    240

tctacagcca tctaccacac gtttgttgct ctgtgctact tgacgcccat cctgggagcg    300

ctcattgcag actcatggct gggaaagttt aagaccattg tctccctgtc cattgtctat    360

acaattgggc aggcagtcat ggctgtaagc tccataaacg acatgacaga tcaaaacaga    420

gatggcaatc ctgataatat tgcggtgcac attgccctgt ctatgactgg cttgattctc    480

atcgcgcttg gaactggtgg gatcaaacct tgtgtctcag catttggtgg ggatcagttt    540

gaagaacatc aggaaaaaca aagaagtaga ttcttctcta tcttttattt gtccattaat    600

gctggaagtc tcatatccac tataatcacc ccaattctca gagctcaaga atgtggcatt    660

cacagcagac agcagtgcta cccgctggca tttggagttc ccgctgccct catggctgtt    720

tcattagttg tgttcatagc tggaagtgga atgtacaaaa aagttcaacc gcaaggcaat    780

ataatggttc gagtttgtaa atgcattgga tttgccatta aaaacaggtt tcggcatcgc    840

agcaaagagt atcccaaaag agagcactgg ctagactggg caagcgagaa gtatgataaa    900

cgactgattg ctcagaccaa gatggtgttg aaggtgcttt tcctttacat ccctctcccg    960

atgttctggg cactttttga ccagcaggga tcgagatgga cactgcaagc cacaactatg   1020

gatggggact ttggagctat gcagattcag ccagaccaaa tgcagactgt caatccaatc   1080

ctgattataa taatggtccc agttgtagat gctgtgattt atcctttaat ccagaaatgc   1140

aagatcaatt ttacgcccct gaggaggatc actgttggca tgttccttgc tggtctggct   1200

ttcgttgctg ctgctctttt gcaagtgcaa atagataaaa ctcttccagt tttccctgca   1260

gctggacagg cccaaatcaa aataataaat ctaggtgata gcaatgcgaa tgttacattt   1320

ctgcctaatc ttcagaacgt gactgtcctt cccatggagt caacaggcta caggatgttt   1380

gagtcttccc agctaaaatc tgtaatggta aattttggga gtgagagtag aagtgaaaat   1440

atcgactcaa taagcagcaa tacgcatact gtcaccatca agaatgcagc agccggcatt   1500

gtttctagct tgcggtctga taatttcaca tcaaaaccag aagaaggaaa gaatctagtc   1560

aggtttgtaa ataatttgcc tcagacagtc aacatcacta tgggtgacac gacttttgga   1620

atactggaag agacaagtat cagtaattac agtccgttct caggaggaag aacatatgat   1680

atagtgataa ctgcaggttc aactaattgc aaaccaactt cagagaaatt aggatatggt   1740

ggtgcttata cgatcgtaat taatgagtgt tctggagatg tgactcaatt aagatacatt   1800

gaagatatcc aacccaatac agtccatatg gcttggcaga tccctcagta tttcatactt   1860

acatgtggag aagtagtctt ctctgtcact gggctggagt tttcatactc acaggcacca   1920

tctaatatga agtcagtgct gcaagcagga tggctgctaa cagtggctgt cggtaacata   1980
```

-continued

```
attgtcctta tcgtggctgg agcatccaaa ctcagtgagc agtgggcaga atatgttctc   2040
tttgctgcct tgctttttgc agtttgcatt atttttgctg tcatggcata tttttataca   2100
tatactgatc caaatgaggt tgaagcccaa cttgatgaag aagaaaagaa gaaacaaata   2160
aaacaggatc cagacttgca cggaaaagaa tctgaagctg tctctcagat gtagaaggtg   2220
tattcaagag catttgtaaa tcatggtagc ctgttaactg tccctgcaat aacaggaatc   2280
agggtattgc tgacatcact gggtaatata ccttgtggga gagactaaga aacactgttc   2340
tgacttaaca tacagcctct tgggaagcaa gacgaaatga ttaatctctt gtacagaagc   2400
tggcatcctg aggaaactcc tgcagaattt gcactcttaa aatgtacctc aagctcaata   2460
ccatagcatt aaaatattga aattgcactt ggcactatta gacactctaa aaagatgtat   2520
ttttatactg tatttcaatt ttataatgtg gaggggtggg gaaaaaggtg ttgccaagaa   2580
atagtaattg aagccaaact gtctgcgtga cccttctagc ctcactgtta cttgaaagca   2640
ggtcacatgt gccttaaatt cttttctatg tccttaagaa taataggaga aaggttctta   2700
gatttctcag attaaaatgt ctctgctcca catagcagga acttggacat gcactgtgat   2760
gtgctttatg tgcctattat taactgccca ttggtatgtt cttaattaat tgtgttaatg   2820
ggatgtccac tgaggtgaac agacaatggc aaattatatt ttgaataacc accaagaata   2880
aaacttgtgt tgtaacaaaa aaaaaaaaaa aaaa                              2914
```

<210> SEQ ID NO 7
<211> LENGTH: 1840
<212> TYPE: DNA
<213> ORGANISM: Canis familiaris

<400> SEQUENCE: 7

```
catcttcttc atcgtggtca atgagttctg tgaaagattt tcctactatg gaatgagagc     60
actcctgatt ctgtacttca gacggttcat cgggtgggac gataatctgt ccacggccat    120
ctaccacacg tttgtggctc tgtgctacct gacgccgatc ctcggcgcac tgatcgcaga    180
ctcctggctg ggaaagttca agacaatcgt gtcactctcc attgtctaca caattggaca    240
ggcggtcact gcagtaagct caattaatga cctcacagac tataacaaag atggaactcc    300
tgacaatctg tccgtgcatg tggcactgtc catgattggc ctggccctga tagctctggg    360
aactggagga ataaagccct gtgtgtctgc atttggtgga gaccagtttg aagagggcca    420
ggaaaaacaa agaaacagat tcttttccat cttttatttg gccattaatg ctggaagctt    480
gatttccact attgtcactc ccatgctcag agttcacgaa tgtggaattt acagtcagaa    540
agcttgttac ccactggcat ttggggttcc tgctgctctc atggccgtat ctctgattgt    600
atttgtcatt ggcagtggaa tgtacaagaa gtttcagccc cagggtaatg tcatgggtaa    660
agttgtcaag tgcattggtt ttgccctcaa aaataggttt aggcaccgga gtaagcagtt    720
tcccaagagg gagcactggc tggactgggc taaagagaaa tacgatgagc ggctcatctc    780
tcaaattaag atggtcacaa aagtgatgtt cttgtacatc ccactcccaa tgttctgggc    840
cctgtttgac cagcagggct ccaggtggac actgcaagca acagctatga gtgggaaaat    900
tggacttctt gaagttcagc cagatcagat gcagactgtg aatgccatct tgattgtcgt    960
catggtcccc atcatggatg ccgtggtgta ccctctgatt gcaaaatgtg gcttcaattt   1020
cacctccttg aagaggatga cagttggaat gttcctggct tccatggcct tcgtgatggc   1080
ggcgattgtt cagctggaaa ttgataaaac tcttccagtc ttccccaaac aaaatgaagt   1140
```

-continued

```
ccaaatcaaa gtactgaata taggaaatgg tgccatgaat gtatcttttc ctggagcggt   1200

ggtgacagtt agccaaatga gtcaatcaga tggatttatg acttttgatg tagacaaact   1260

gacaagtata aacatttctt ccactggatc accagtcatt ccagtgactt ataactttga   1320

gcagggccat cgccataccc ttctagtatg ggcccccaat aattaccgag tggtaaagga   1380

tggccttaac cagaagccag aaaaaggaga aaatggaatc agatttataa atagtcttaa   1440

tgagagcctc aacatcacca tgggcgacaa agtttatgtg aatgtcacca gtcacaatgc   1500

cagcgagtat cagttctttt ctttgggcac aaaaaacatt acaataagtt caacacaaca   1560

gatctcacaa aattgtacaa aagttctcca atcatccaac cttgaatttg gtagtgcata   1620

tacctatgta atcggaacgc agagcactgg ctgccctgaa ttgcatatgt ttgaagatat   1680

ttcacccaac acagttaaca tggctctgca gatcccgcag tacttcctca tcacctgcgg   1740

cgaggtggtt ttctctgtca caggactgga gttctcatat tctcaggccc cctccaacat   1800

gaagtcggtg cttcaggcgg gatggctgct gacagtggct                         1840
```

<210> SEQ ID NO 8
<211> LENGTH: 1995
<212> TYPE: DNA
<213> ORGANISM: Canis familiaris

<400> SEQUENCE: 8

```
catcttcttc atcgtggtca atgagttctg tgaaagattt tcctactatg gaatgagagc     60

actcctgatt ctgtacttca gacggttcat cgggtgggac gataatctgt ccacggccat    120

ctaccacacg tttgtggctc tgtgctacct gacgccgatc ctcggcgcac tgatcgcaga    180

ctcctggctg ggaaagttca agacaatcgt gtcactctcc attgtctaca caattggaca    240

ggcggtcact gcagtaagct caattaatga cctcacagac tataacaaag atggaactcc    300

tgacaatctg tccgtgcatg tggcactgtc catgattggc ctggccctga tagctctggg    360

aactggagga ataaagccct gtgtgtctgc atttggtgga gaccagtttg aagagggcca    420

ggaaaaacaa agaaacagat tcttttccat cttttatttg gccattaatg ctggaagctt    480

gatttccact attgtcactc ccatgctcag agttcacgaa tgtggaattt acagtcagaa    540

agcttgttac ccactggcat ttggggttcc tgctgctctc atggccgtat ctctgattgt    600

atttgtcatt ggcagtggaa tgtacaagaa gtttcagccc cagggtaatg tcatgggtaa    660

agttgtcaag tgcattggtt ttgccctcaa aaataggttt aggcaccgga gtaagcagtt    720

tcccaagagg gagcactggc tggactgggc taaagagaaa tacgatgagc ggctcatctc    780

tcaaattaag atggtcacaa aagtgatgtt cttgtacatc ccactcccaa tgttctgggc    840

cctgtttgac cagcagggct ccaggtggac actgcaagca acagctatga gtgggaaaat    900

tggacttctt gaagttcagc cagatcagat gcagactgtg aatgccatct tgattgtcgt    960

catggtcccc atcatggatg ccgtggtgta ccctctgatt gcaaaatgtg gcttcaattt   1020

cacctccttg aagaggatga cagttggaat gttcctggct tccatggcct tcgtgatggc   1080

ggcgattgtt cagctggaaa ttgataaaac tcttccagtc ttccccaaac aaaatgaagt   1140

ccaaatcaaa gtactgaata taggaaatgg tgccatgaat gtatcttttc ctggagcggt   1200

ggtgacagtt agccaaatga gtcaatcaga tggatttatg acttttgatg tagacaaact   1260

gacaagtata aacatttctt ccactggatc accagtcatt ccagtgactt ataactttga   1320

gcagggccat cgccataccc ttctagtatg ggcccccaat aattaccgag tggtaaagga   1380

tggccttaac cagaagccag aaaaaggaga aaatggaatc agatttataa atagtcttaa   1440
```

-continued tgagagcctc aacatcacca tgggcgacaa agtttatgtg aatgtcacca gtcacaatgc 1500
cagcgagtat cagttctttt ctttgggcac aaaaaacatt acaataagtt caacacaaca 1560
gatctcacaa aattgtacaa aagttctcca atcatccaac cttgaatttg gtagtgcata 1620
tacctatgta atcggaacgc agagcactgg ctgccctgaa ttgcatatgt ttgaagatat 1680
ttcacccaac acagttaaca tggctctgca gatcccgcag tacttcctca tcacctgcgg 1740
cgaggtggtt ttctctgtca caggactgga gttctcatat tctcaggccc cctccaacat 1800
gaagtcggtg cttcaggcgg gatggctgct gacagtggct tgttggcaac atcattgtgc 1860
tcattgtggc aggagcaggc cagttcagtg aacagtgggc tgaatacatc ctatttgcgg 1920
cattgcttct ggttgtctgt gtaatatttg ccatcatggc ccggttttac acttacgtca 1980
atccagcaga gattg 1995

<210> SEQ ID NO 9
<211> LENGTH: 381
<212> TYPE: DNA
<213> ORGANISM: Canis familiaris

<400> SEQUENCE: 9
tggctgggga agttcaagac aatcgtgtca ctctccattg tctacacaat tggacaggcg 60
gtcactgcag taagctcaat taatgacctc acagactata acaaagatgg aactcctgac 120
aatctgtccg tgtatgtggc actgtccatg attggcctgg ccctgatagc tctgggaact 180
ggaggaataa agccctgtgt gtctgcattt ggtggagacc agtttgaaga gggccaggaa 240
aaacaaagaa acagattctt ttccatcttt tatttggcca ttaatgctgg aagcttgatt 300
tccactattg tcactcccat gctcagagtt cacgaatgtg gaatttacag tcagaaagct 360
tgctacccac tggcctttgg g 381

<210> SEQ ID NO 10
<211> LENGTH: 4
<212> TYPE: PRT
<213> ORGANISM: Artificial Sequence
<220> FEATURE:
<223> OTHER INFORMATION: tetrapeptide

<400> SEQUENCE: 10

Met Gly Met Met
1

<210> SEQ ID NO 11
<211> LENGTH: 1410
<212> TYPE: DNA
<213> ORGANISM: Canis familiaris

<400> SEQUENCE: 11
catcttcttc atcgtggtca atgagttctg tgaaagattt tcctactatg gaatgagagc 60
actcctgatt ctgtacttca gacggttcat cgggtgggac gataatctgt ccacggccat 120
ctaccacacg tttgtggctc tgtgctacct gacgccgatc ctcggcgcac tgatcgcaga 180
ctcctggctg ggaaagttca agacaatcgt gtcactctcc attgtctaca caattggaca 240
ggcggtcact gcagtaagct caattaatga cctcacagac tataacaaag atggaactcc 300
tgacaatctg tccgtgcatg tggcactgtc catgattggc ctggccctga tagctctggg 360
aactggagga ataaagccct gtgtgtctgc atttggtgga gaccagtttg aagagggcca 420
ggaaaaacaa agaaacagat tcttttccat cttttatttg gccattaatg ctggaagctt 480

-continued

```
gatttccact attgtcactc ccatgctcag agttcacgaa tgtggaattt acagtcagaa    540
agcttgttac ccactggcat ttggggttcc tgctgctctc atggccgtat ctctgattgt    600
atttgtcatt ggcagtggaa tgtacaagaa gtttcagccc cagggtaatg tcatgggtaa    660
agttgtcaag tgcattggtt ttgccctcaa aaataggttt aggcaccgga gtaagcagtt    720
tcccaagagg gagcactggc tggactgggc taaagagaaa tacgatgagc ggctcatctc    780
tcaaattaag atggtcacaa aagtgatgtt cttgtacatc ccactcccaa tgttctgggc    840
cctgtttgac cagcagggct ccaggtggac actgcaagca acagctatga gtgggaaaat    900
tggacttctt gaagttcagc cagatcagat gcagactgtg aatgccatct tgattgtcgt    960
catggtcccc atcatggatg ccgtggtgta ccctctgatt gcaaaatgtg gcttcaattt   1020
cacctccttg aagaggatga cagttggaat gttcctggct tccatggcct tcgtgatggc   1080
ggcgattgtt cagctggaaa ttgataaaac tcttccagtc ttccccaaac aaaatgaagt   1140
ccaaatcaaa gtactgaata taggaaatgg tgccatgaat gtatcttttc ctggagcggt   1200
ggtgacagtt agccaaatga gtcaatcaga tggatttatg acttttgatg tagacaaact   1260
gacaagtata aacatttctt ccactggatc accagtcatt ccagtgactt ataactttga   1320
gcagggccat cgccataccc ttctagtatg ggcccccaat aattaccgag tggtaaagga   1380
tggccttaac cagaagccag aaaaagggag                                    1410
```

```
<210> SEQ ID NO 12
<211> LENGTH: 670
<212> TYPE: DNA
<213> ORGANISM: Canis familiaris

<400> SEQUENCE: 12

gccatcgcca taccottcta gtatgggccc ccaataatta ccgagtggta aaggatggcc     60
ttaaccagaa gccagaaaaa ggagaaaatg gaatcagatt tataaatagt cttaatgaga    120
gcctcaacat caccatgggc gacaaagttt atgtgaatgt caccagtcac aatgccagcg    180
agtatcagtt cttttctttg ggcacaaaaa acattacaat aagttcaaca caacagatct    240
cacaaaattg tacaaaagtt ctccaatcat ccaaccttga atttggtagt gcatatacct    300
atgtaatcgg aacgcagagc actggctgcc ctgaattgca tatgtttgaa gatatttcac    360
ccaacacagt taacatggct ctgcagatcc cgcagtactt cctcatcacc tgcggcgagg    420
tggttttctc tgtcacagga ctggagttct catattctca ggccccctcc aacatgaagt    480
cggtgcttca ggcgggatgg ctgctgacag tggcttgttg gcaacatcat tgtgctcatt    540
gtggcaggag caggccagtt cagtgaacag tgggctgaat acatcctatt tgcggcattg    600
cttctggttg tctgtgtaat atttgccatc atggcccggt tttacactta cgtcaatcca    660
gcagagattg                                                          670

<210> SEQ ID NO 13
<211> LENGTH: 662
<212> TYPE: PRT
<213> ORGANISM: Canis familiaris

<400> SEQUENCE: 13

Ile Phe Phe Ile Val Val Asn Glu Phe Cys Glu Arg Phe Ser Tyr Tyr
 1               5                  10                  15

Gly Met Arg Ala Leu Leu Ile Leu Tyr Phe Arg Arg Phe Ile Gly Trp
            20                  25                  30
```

-continued

```
Asp Asp Asn Leu Ser Thr Ala Ile Tyr His Thr Phe Val Ala Leu Cys
        35                  40                  45

Tyr Leu Thr Pro Ile Leu Gly Ala Leu Ile Ala Asp Ser Trp Leu Gly
    50                  55                  60

Lys Phe Lys Thr Ile Val Ser Leu Ser Ile Val Tyr Thr Ile Gly Gln
65                  70                  75                  80

Ala Val Thr Ala Val Ser Ser Ile Asn Asp Leu Thr Asp Tyr Asn Lys
                85                  90                  95

Asp Gly Thr Pro Asp Asn Leu Ser Val His Val Ala Leu Ser Met Ile
            100                 105                 110

Gly Leu Ala Leu Ile Ala Leu Gly Thr Gly Gly Ile Lys Pro Cys Val
        115                 120                 125

Ser Ala Phe Gly Gly Asp Gln Phe Glu Glu Gly Gln Glu Lys Gln Arg
    130                 135                 140

Asn Arg Phe Phe Ser Ile Phe Tyr Leu Ala Ile Asn Ala Gly Ser Leu
145                 150                 155                 160

Ile Ser Thr Ile Val Thr Pro Met Leu Arg Val His Glu Cys Gly Ile
                165                 170                 175

Tyr Ser Gln Lys Ala Cys Tyr Pro Leu Ala Phe Gly Val Pro Ala Ala
            180                 185                 190

Leu Met Ala Val Ser Leu Ile Val Phe Val Ile Gly Ser Gly Met Tyr
        195                 200                 205

Lys Lys Phe Gln Pro Gln Gly Asn Val Met Gly Lys Val Val Lys Cys
    210                 215                 220

Ile Gly Phe Ala Leu Lys Asn Arg Phe Arg His Arg Ser Lys Gln Phe
225                 230                 235                 240

Pro Lys Arg Glu His Trp Leu Asp Trp Ala Lys Glu Lys Tyr Asp Glu
                245                 250                 255

Arg Leu Ile Ser Gln Ile Lys Met Val Thr Lys Val Met Phe Leu Tyr
            260                 265                 270

Ile Pro Leu Pro Met Phe Trp Ala Leu Phe Asp Gln Gln Gly Ser Arg
        275                 280                 285

Trp Thr Leu Gln Ala Thr Ala Met Ser Gly Lys Ile Gly Leu Leu Glu
    290                 295                 300

Val Gln Pro Asp Gln Met Gln Thr Val Asn Ala Ile Leu Ile Val Val
305                 310                 315                 320

Met Val Pro Ile Met Asp Ala Val Val Tyr Pro Leu Ile Ala Lys Cys
                325                 330                 335

Gly Phe Asn Phe Thr Ser Leu Lys Arg Met Thr Val Gly Met Phe Leu
            340                 345                 350

Ala Ser Met Ala Phe Val Met Ala Ala Ile Val Gln Leu Glu Ile Asp
        355                 360                 365

Lys Thr Leu Pro Val Phe Pro Lys Gln Asn Glu Val Gln Ile Lys Val
    370                 375                 380

Leu Asn Ile Gly Asn Gly Ala Met Asn Val Ser Phe Pro Gly Ala Val
385                 390                 395                 400

Val Thr Val Ser Gln Met Ser Gln Ser Asp Gly Phe Met Thr Phe Asp
                405                 410                 415

Val Asp Lys Leu Thr Ser Ile Asn Ile Ser Ser Thr Gly Ser Pro Val
            420                 425                 430

Ile Pro Val Thr Tyr Asn Phe Glu Gln Gly His Arg His Thr Leu Leu
        435                 440                 445

Val Trp Ala Pro Asn Asn Tyr Arg Val Val Lys Asp Gly Leu Asn Gln
```

-continued

```
    450                 455                 460

Lys Pro Glu Lys Gly Glu Asn Gly Ile Arg Phe Ile Asn Ser Leu Asn
465                 470                 475                 480

Glu Ser Leu Asn Ile Thr Met Gly Asp Lys Val Tyr Val Asn Val Thr
                485                 490                 495

Ser His Asn Ala Ser Glu Tyr Gln Phe Phe Ser Leu Gly Thr Lys Asn
            500                 505                 510

Ile Thr Ile Ser Ser Thr Gln Gln Ile Ser Gln Asn Cys Thr Lys Val
        515                 520                 525

Leu Gln Ser Ser Asn Leu Glu Phe Gly Ser Ala Tyr Thr Tyr Val Ile
    530                 535                 540

Gly Thr Gln Ser Thr Gly Cys Pro Glu Leu His Met Phe Glu Asp Ile
545                 550                 555                 560

Ser Pro Asn Thr Val Asn Met Ala Leu Gln Ile Pro Gln Tyr Phe Leu
                565                 570                 575

Ile Thr Cys Gly Glu Val Val Phe Ser Val Thr Gly Leu Glu Phe Ser
            580                 585                 590

Tyr Ser Gln Ala Pro Ser Asn Met Lys Ser Val Leu Gln Ala Gly Trp
        595                 600                 605

Leu Leu Thr Val Ala Cys Trp Gln His His Cys Ala His Cys Gly Arg
    610                 615                 620

Ser Arg Pro Val Gln Thr Val Gly Ile His Pro Ile Cys Gly Ile Ala
625                 630                 635                 640

Ser Gly Cys Leu Cys Asn Ile Cys His His Gly Pro Val Leu His Leu
                645                 650                 655

Arg Gln Ser Ser Arg Asp
            660


<210> SEQ ID NO 14
<211> LENGTH: 706
<212> TYPE: PRT
<213> ORGANISM: Homo sapien

<400> SEQUENCE: 14

Met Ser Lys Ser His Ser Phe Phe Gly Tyr Pro Leu Ser Ile Phe Phe
 1               5                  10                  15

Ile Val Val Asn Glu Phe Cys Glu Arg Phe Ser Tyr Tyr Gly Met Arg
            20                  25                  30

Ala Ile Leu Ile Leu Tyr Phe Thr Asn Phe Ile Ser Trp Asp Asp Asn
        35                  40                  45

Leu Ser Thr Ala Ile Tyr His Thr Phe Val Ala Leu Cys Tyr Leu Thr
    50                  55                  60

Pro Ile Leu Gly Ala Leu Ile Ala Asp Ser Trp Leu Gly Lys Phe Lys
65                  70                  75                  80

Thr Ile Val Ser Leu Ser Ile Val Tyr Thr Ile Gly Gln Ala Val Thr
                85                  90                  95

Ser Val Ser Ser Ile Asn Asp Leu Thr Asp His Asn His Asp Gly Thr
            100                 105                 110

Pro Asp Ser Leu Pro Val His Val Val Leu Ser Leu Ile Gly Leu Ala
        115                 120                 125

Leu Ile Ala Leu Gly Thr Gly Gly Ile Lys Pro Cys Val Ser Ala Phe
    130                 135                 140

Gly Gly Asp Gln Phe Glu Glu Gly Gln Glu Lys Gln Arg Asn Arg Phe
145                 150                 155                 160
```

-continued

```
Phe Ser Ile Phe Tyr Leu Ala Ile Asn Ala Gly Ser Leu Leu Ser Thr
                165                 170                 175

Ile Ile Thr Pro Met Leu Arg Val Gln Gln Cys Gly Ile His Ser Lys
            180                 185                 190

Gln Ala Cys Tyr Pro Leu Ala Phe Gly Val Pro Ala Ala Leu Met Ala
        195                 200                 205

Val Ala Leu Ile Val Phe Val Leu Gly Ser Gly Met Tyr Lys Lys Phe
    210                 215                 220

Lys Pro Gln Gly Asn Ile Met Gly Lys Val Ala Lys Cys Ile Gly Phe
225                 230                 235                 240

Ala Ile Lys Asn Arg Phe Arg His Arg Ser Lys Ala Phe Pro Lys Arg
                245                 250                 255

Glu His Trp Leu Asp Trp Ala Lys Glu Lys Tyr Asp Glu Arg Leu Ile
            260                 265                 270

Ser Gln Ile Lys Met Val Thr Arg Val Met Phe Leu Tyr Ile Pro Leu
        275                 280                 285

Pro Met Phe Trp Ala Leu Phe Asp Gln Gln Gly Ser Arg Trp Thr Leu
    290                 295                 300

Gln Ala Thr Thr Met Ser Gly Lys Ile Gly Ala Leu Glu Ile Gln Pro
305                 310                 315                 320

Asp Gln Met Gln Thr Val Asn Ala Ile Leu Ile Val Ile Met Val Pro
                325                 330                 335

Ile Phe Asp Ala Val Leu Tyr Pro Leu Ile Ala Lys Cys Gly Phe Asn
            340                 345                 350

Phe Thr Ser Leu Lys Lys Met Ala Val Gly Met Val Leu Ala Ser Met
        355                 360                 365

Ala Phe Val Val Ala Ala Ile Val Gln Val Glu Ile Asp Lys Thr Leu
    370                 375                 380

Pro Val Phe Pro Lys Gly Asn Glu Val Gln Ile Lys Val Leu Asn Ile
385                 390                 395                 400

Gly Asn Asn Thr Met Asn Ile Ser Leu Pro Gly Glu Met Val Thr Leu
                405                 410                 415

Gly Pro Met Ser Gln Thr Asn Ala Phe Met Thr Phe Asp Val Asn Lys
            420                 425                 430

Leu Thr Arg Ile Asn Ile Ser Ser Pro Gly Ser Pro Val Thr Ala Val
        435                 440                 445

Thr Asp Asp Phe Lys Gln Gly Gln Arg His Thr Leu Leu Val Trp Ala
    450                 455                 460

Pro Asn His Tyr Gln Val Val Lys Asp Gly Leu Asn Gln Lys Pro Glu
465                 470                 475                 480

Lys Gly Glu Asn Gly Ile Arg Phe Val Asn Thr Phe Asn Glu Leu Ile
                485                 490                 495

Thr Ile Thr Met Ser Gly Lys Val Tyr Ala Asn Ile Ser Ser Tyr Asn
            500                 505                 510

Ala Ser Thr Tyr Gln Phe Phe Pro Ser Gly Ile Lys Gly Phe Thr Ile
        515                 520                 525

Ser Ser Thr Glu Ile Pro Pro Gln Cys Gln Pro Asn Phe Asn Thr Phe
    530                 535                 540

Tyr Leu Glu Phe Gly Ser Ala Tyr Thr Tyr Ile Val Gln Arg Lys Asn
545                 550                 555                 560

Asp Ser Cys Pro Glu Val Lys Val Phe Glu Asp Ile Ser Ala Asn Thr
                565                 570                 575

Val Asn Met Ala Leu Gln Ile Pro Gln Tyr Phe Leu Leu Thr Cys Gly
```

-continued

```
            580                 585                 590

Glu Val Val Phe Ser Val Thr Gly Leu Glu Phe Ser Tyr Ser Gln Ala
        595                 600                 605

Pro Ser Asn Met Lys Ser Val Leu Gln Ala Gly Trp Leu Leu Thr Val
    610                 615                 620

Ala Val Gly Asn Ile Ile Val Leu Ile Val Ala Gly Ala Gly Gln Phe
625                 630                 635                 640

Ser Lys Gln Trp Ala Glu Tyr Ile Leu Phe Ala Ala Leu Leu Leu Val
                645                 650                 655

Val Cys Val Ile Phe Ala Ile Met Ala Arg Phe Tyr Thr Tyr Ile Asn
            660                 665                 670

Pro Ala Glu Ile Glu Ala Gln Phe Asp Glu Asp Glu Lys Lys Asn Arg
        675                 680                 685

Leu Glu Lys Ser Asn Pro Tyr Phe Met Ser Gly Ala Asn Ser Gln Lys
    690                 695                 700

Gln Met
705


<210> SEQ ID NO 15
<211> LENGTH: 710
<212> TYPE: PRT
<213> ORGANISM: Rattus norvegicus

<400> SEQUENCE: 15

Met Gly Met Ser Lys Ser Arg Gly Cys Phe Gly Tyr Pro Leu Ser Ile
 1               5                  10                  15

Phe Phe Ile Val Val Asn Glu Phe Cys Glu Arg Phe Ser Tyr Tyr Gly
            20                  25                  30

Met Arg Ala Leu Leu Val Leu Tyr Phe Arg Asn Phe Leu Gly Trp Asp
        35                  40                  45

Asp Asp Leu Ser Thr Ala Ile Tyr His Thr Phe Val Ala Leu Cys Tyr
    50                  55                  60

Leu Thr Pro Ile Leu Gly Ala Leu Ile Ala Asp Ser Trp Leu Gly Lys
65                  70                  75                  80

Phe Lys Thr Ile Val Ser Leu Ser Ile Val Tyr Thr Ile Gly Gln Ala
                85                  90                  95

Val Ile Ser Val Ser Ser Ile Asn Asp Leu Thr Asp His Asp His Asp
            100                 105                 110

Gly Ser Pro Asn Asn Leu Pro Leu His Val Ala Leu Ser Met Ile Gly
        115                 120                 125

Leu Ala Leu Ile Ala Leu Gly Thr Gly Gly Ile Lys Pro Cys Val Ser
    130                 135                 140

Ala Phe Gly Gly Asp Gln Phe Glu Glu Gly Gln Glu Lys Gln Arg Asn
145                 150                 155                 160

Arg Phe Phe Ser Ile Phe Tyr Leu Ala Ile Asn Ala Gly Ser Leu Leu
                165                 170                 175

Ser Thr Ile Ile Thr Pro Ile Leu Arg Val Gln Gln Cys Gly Ile His
            180                 185                 190

Ser Gln Gln Ala Cys Tyr Pro Leu Ala Phe Gly Val Pro Ala Ala Leu
        195                 200                 205

Met Ala Val Ala Leu Ile Val Phe Val Leu Gly Ser Gly Met Tyr Lys
    210                 215                 220

Lys Phe Gln Pro Gln Gly Asn Ile Met Gly Lys Val Ala Lys Cys Ile
225                 230                 235                 240
```

-continued

```
Gly Phe Ala Ile Lys Asn Arg Phe Arg His Arg Ser Lys Ala Phe Pro
                245                 250                 255

Lys Arg Glu His Trp Leu Asp Trp Ala Lys Glu Lys Tyr Asp Glu Arg
            260                 265                 270

Leu Ile Ser Gln Ile Lys Met Val Thr Lys Val Met Phe Leu Tyr Ile
        275                 280                 285

Pro Leu Pro Met Phe Trp Ala Leu Phe Asp Gln Gln Gly Ser Arg Trp
    290                 295                 300

Thr Leu Gln Ala Thr Thr Met Thr Gly Lys Ile Gly Thr Ile Glu Ile
305                 310                 315                 320

Gln Pro Asp Gln Met Gln Thr Val Asn Ala Ile Leu Ile Val Ile Met
                325                 330                 335

Val Pro Ile Val Asp Ala Val Val Tyr Pro Leu Ile Ala Lys Cys Gly
            340                 345                 350

Phe Asn Phe Thr Ser Leu Lys Lys Met Thr Val Gly Met Phe Leu Ala
        355                 360                 365

Ser Met Ala Phe Val Val Ala Ala Ile Val Gln Val Glu Ile Asp Lys
    370                 375                 380

Thr Leu Pro Val Phe Pro Ser Gly Asn Gln Val Gln Ile Lys Val Leu
385                 390                 395                 400

Asn Ile Gly Asn Asn Asp Met Ala Val Tyr Phe Pro Gly Lys Asn Val
                405                 410                 415

Thr Val Ala Gln Met Ser Gln Thr Asp Thr Phe Met Thr Phe Asp Val
            420                 425                 430

Asp Gln Leu Thr Ser Ile Asn Val Ser Ser Pro Gly Ser Pro Gly Val
        435                 440                 445

Thr Thr Val Ala His Glu Phe Glu Pro Gly His Arg His Thr Leu Leu
    450                 455                 460

Val Trp Gly Pro Asn Leu Tyr Arg Val Val Lys Asp Gly Leu Asn Gln
465                 470                 475                 480

Lys Pro Glu Lys Gly Glu Asn Gly Ile Arg Phe Val Ser Thr Leu Asn
                485                 490                 495

Glu Met Ile Thr Ile Lys Met Ser Gly Lys Val Tyr Glu Asn Val Thr
            500                 505                 510

Ser His Ser Ala Ser Asn Tyr Gln Phe Phe Pro Ser Gly Gln Lys Asp
        515                 520                 525

Tyr Thr Ile Asn Thr Thr Glu Ile Ala Pro Asn Cys Ser Ser Asp Phe
    530                 535                 540

Lys Ser Ser Asn Leu Asp Phe Gly Ser Ala Tyr Thr Tyr Val Ile Arg
545                 550                 555                 560

Ser Arg Ala Ser Asp Gly Cys Leu Glu Val Lys Glu Phe Glu Asp Ile
                565                 570                 575

Pro Pro Asn Thr Val Asn Met Ala Leu Gln Ile Pro Gln Tyr Phe Leu
            580                 585                 590

Leu Thr Cys Gly Glu Val Val Phe Ser Val Thr Gly Leu Glu Phe Ser
        595                 600                 605

Tyr Ser Gln Ala Pro Ser Asn Met Lys Ser Val Leu Gln Ala Gly Trp
    610                 615                 620

Leu Leu Thr Val Ala Ile Gly Asn Ile Ile Val Leu Ile Val Ala Glu
625                 630                 635                 640

Ala Gly His Phe Asp Lys Gln Trp Ala Glu Tyr Val Leu Phe Ala Ser
                645                 650                 655

Leu Leu Leu Val Val Cys Ile Ile Phe Ala Ile Met Ala Arg Phe Tyr
```

-continued

```
            660                 665                 670

Thr Tyr Ile Asn Pro Ala Glu Ile Glu Ala Gln Phe Asp Glu Asp Glu
        675                 680                 685

Lys Lys Lys Gly Val Gly Lys Glu Asn Pro Tyr Ser Ser Leu Glu Pro
    690                 695                 700

Val Ser Gln Thr Asn Met
705                 710


<210> SEQ ID NO 16
<211> LENGTH: 709
<212> TYPE: PRT
<213> ORGANISM: Mus musculus

<400> SEQUENCE: 16

Met Gly Met Ser Lys Ser Arg Gly Cys Phe Gly Tyr Pro Leu Ser Ile
 1               5                  10                  15

Phe Phe Ile Val Val Asn Glu Phe Cys Glu Arg Phe Ser Tyr Tyr Gly
            20                  25                  30

Met Arg Ala Leu Leu Val Leu Tyr Phe Arg Asn Phe Leu Gly Trp Asp
        35                  40                  45

Asp Asn Leu Ser Thr Ala Ile Tyr His Thr Phe Val Ala Leu Cys Tyr
    50                  55                  60

Leu Thr Pro Ile Leu Gly Ala Leu Ile Ala Asp Ser Trp Leu Gly Lys
65                  70                  75                  80

Phe Lys Thr Ile Val Ser Leu Ser Ile Val Tyr Thr Ile Gly Gln Ala
                85                  90                  95

Val Ile Ser Val Ser Ser Ile Asn Asp Leu Thr Asp His Asp His Asn
            100                 105                 110

Gly Ser Pro Asp Ser Leu Pro Val His Val Ala Leu Ser Met Val Gly
        115                 120                 125

Leu Ala Leu Ile Ala Leu Gly Thr Gly Gly Ile Lys Pro Cys Val Ser
    130                 135                 140

Ala Phe Gly Gly Asp Gln Phe Glu Glu Gly Gln Glu Lys Gln Arg Asn
145                 150                 155                 160

Arg Phe Phe Ser Ile Phe Tyr Leu Ala Ile Asn Gly Gly Ser Leu Leu
                165                 170                 175

Ser Thr Ile Ile Thr Pro Ile Leu Arg Val Gln Gln Cys Gly Ile His
            180                 185                 190

Ser Gln Gln Ala Cys Tyr Pro Leu Ala Phe Gly Val Pro Ala Ala Leu
        195                 200                 205

Met Ala Val Ala Leu Ile Val Phe Val Leu Gly Ser Gly Met Tyr Lys
    210                 215                 220

Lys Phe Gln Pro Gln Gly Asn Ile Met Gly Lys Val Ala Lys Cys Ile
225                 230                 235                 240

Gly Phe Ala Ile Lys Asn Arg Phe Arg His Arg Ser Lys Ala Tyr Pro
                245                 250                 255

Lys Arg Glu His Trp Leu Asp Trp Ala Lys Glu Lys Tyr Asp Glu Arg
            260                 265                 270

Leu Ile Ser Gln Ile Lys Met Val Thr Lys Val Met Phe Leu Phe Ile
        275                 280                 285

Pro Leu Pro Met Phe Trp Gly Leu Phe Asp Gln Gln Gly Ser Arg Trp
    290                 295                 300

Thr Leu Gln Ala Thr Thr Met Asn Gly Lys Ile Gly Ala Asn Glu Ile
305                 310                 315                 320
```

-continued

```
Gln Pro Asp Gln Met Gln Thr Val Asn Ala Ile Leu Asn Val Asn Asn
                325                 330                 335

Gly Pro Asn Val Asp Ala Val Val Tyr Arg Ser Ile Ala Lys Cys Gly
            340                 345                 350

Phe Asn Phe Thr Ser Leu Lys Lys Met Thr Val Gly Met Phe Leu Ala
        355                 360                 365

Ser Met Ala Phe Val Val Ala Ala Ile Val Gln Val Glu Ile Asp Lys
    370                 375                 380

Thr Leu Pro Val Phe Pro Gly Gly Asn Gln Val Gln Ile Lys Val Leu
385                 390                 395                 400

Asn Ile Gly Asn Asn Asn Met Thr Val His Phe Pro Gly Asn Ser Val
                405                 410                 415

Thr Leu Ala Gln Met Ser Gln Thr Asp Thr Phe Met Thr Phe Asp Ile
            420                 425                 430

Asp Lys Leu Thr Ser Ile Asn Ile Ser Ser Ser Gly Ser Pro Gly Val
        435                 440                 445

Thr Thr Val Ala His Asp Phe Glu Gln Gly His Arg His Asn Leu Leu
    450                 455                 460

Val Trp Glu Pro Ser Gln Tyr Arg Val Val Lys Asp Gly Pro Asn Gln
465                 470                 475                 480

Lys Pro Glu Lys Gly Glu Asn Gly Ile Arg Phe Val Asn Thr Leu Asn
                485                 490                 495

Glu Met Val Thr Asn Lys Met Ser Gly Lys Val Tyr Glu Lys Phe Thr
            500                 505                 510

Ser His Asn Ala Ser Gly Tyr Lys Phe Leu Pro Ser Gly Glu Lys Gln
        515                 520                 525

Tyr Thr Ile Asn Thr Thr Ala Val Ala Pro Thr Cys Leu Thr Asp Phe
    530                 535                 540

Lys Ser Ser Asn Leu Asp Phe Gly Ser Ala Tyr Thr Tyr Val Ile Arg
545                 550                 555                 560

Arg Ala Ser Asp Gly Cys Leu Glu Val Lys Glu Phe Glu Asp Ile Pro
                565                 570                 575

Pro Asn Thr Val Asn Met Ala Leu Gln Ile Pro Gln Tyr Phe Leu Leu
            580                 585                 590

Thr Cys Gly Glu Val Val Phe Ser Val Thr Gly Leu Glu Phe Ser Tyr
        595                 600                 605

Ser Gln Ala Pro Ser Asn Met Lys Ser Val Leu Gln Ala Gly Trp Leu
    610                 615                 620

Leu Thr Val Ala Val Gly Asn Ile Ile Val Leu Ile Val Ala Gly Ala
625                 630                 635                 640

Gly His Phe Pro Lys Gln Trp Ala Glu Tyr Ile Leu Phe Ala Ser Leu
                645                 650                 655

Leu Leu Val Val Cys Val Ile Phe Ala Ile Met Ala Arg Phe Tyr Thr
            660                 665                 670

Tyr Ile Asn Pro Ala Glu Ile Glu Ala Gln Phe Asp Glu Asp Glu Lys
        675                 680                 685

Lys Lys Gly Ile Gly Lys Glu Asn Pro Tyr Ser Ser Leu Glu Pro Val
    690                 695                 700

Ser Gln Thr Asn Met
705
```

<210> SEQ ID NO 17
<211> LENGTH: 707
<212> TYPE: PRT

-continued

<213> ORGANISM: Ovis aries

<400> SEQUENCE: 17

Met Gly Met Ser Val Pro Lys Ser Cys Phe Gly Tyr Pro Leu Ser Ile
1 5 10 15

Phe Phe Ile Val Val Asn Glu Phe Cys Glu Arg Phe Ser Tyr Tyr Gly
20 25 30

Met Arg Ala Leu Leu Ile Leu Tyr Phe Gln Arg Phe Leu Gly Trp Asn
35 40 45

Asp Asn Leu Gly Thr Ala Ile Tyr His Thr Phe Val Ala Leu Cys Tyr
50 55 60

Leu Thr Pro Ile Leu Gly Ala Leu Ile Ala Asp Ser Trp Leu Gly Lys
65 70 75 80

Phe Lys Thr Ile Val Ser Leu Ser Ile Val Tyr Thr Ile Gly Gln Val
85 90 95

Val Ile Ala Val Ser Ser Ile Asn Asp Leu Thr Asp Phe Asn His Asp
100 105 110

Gly Thr Pro Asn Asn Ile Ser Val His Val Ala Leu Ser Met Ile Gly
115 120 125

Leu Val Leu Ile Ala Leu Gly Thr Gly Gly Ile Lys Pro Cys Val Ser
130 135 140

Ala Phe Gly Gly Asp Gln Phe Glu Glu Gly Gln Glu Lys Gln Arg Asn
145 150 155 160

Arg Phe Phe Ser Ile Phe Tyr Leu Ala Ile Asn Ala Gly Ser Leu Leu
165 170 175

Ser Thr Ile Ile Thr Pro Met Leu Arg Val Gln Val Cys Gly Ile His
180 185 190

Ser Lys Gln Ala Cys Tyr Pro Leu Ala Phe Gly Val Pro Ala Ala Leu
195 200 205

Met Ala Val Ser Leu Ile Val Phe Val Ile Gly Ser Gly Met Tyr Lys
210 215 220

Lys Val Gln Pro Gln Gly Asn Ile Met Ser Lys Val Ala Arg Cys Ile
225 230 235 240

Gly Phe Ala Ile Lys Asn Arg Ile Ser His Arg Ser Lys Lys Phe Pro
245 250 255

Lys Arg Glu His Trp Leu Asp Trp Ala Ser Glu Lys Tyr Asp Glu Arg
260 265 270

Leu Ile Ser Gln Ile Lys Met Val Thr Arg Val Met Phe Leu Tyr Ile
275 280 285

Pro Leu Pro Met Phe Trp Ala Leu Phe Asp Gln Gln Gly Ser Arg Trp
290 295 300

Thr Leu Gln Ala Thr Thr Met Ser Gly Lys Ile Gly Ile Ile Glu Ile
305 310 315 320

Gln Pro Asp Gln Met Gln Thr Val Asn Ala Ile Leu Ile Val Val Met
325 330 335

Val Pro Ile Val Asp Ala Val Val Tyr Pro Leu Ile Ala Lys Cys Gly
340 345 350

Leu Asn Phe Thr Ser Leu Lys Lys Met Thr Val Gly Met Phe Leu Ala
355 360 365

Ser Met Ala Phe Val Ala Ala Ala Ile Val Gln Val Asp Ile Asp Lys
370 375 380

Thr Leu Pro Val Phe Pro Lys Gly Asn Glu Val Gln Ile Lys Val Leu
385 390 395 400

-continued

```
Asn Ile Gly Asn Asn Ser Met Thr Val Ser Phe Pro Gly Thr Thr Val
                405                 410                 415

Thr Cys Asp Gln Met Ser Gln Thr Asn Gly Phe Leu Thr Phe Asn Val
            420                 425                 430

Asp Asn Leu Ser Ile Asn Ile Ser Ser Thr Gly Thr Pro Val Thr Pro
        435                 440                 445

Val Thr His Asn Phe Glu Ser Gly His Arg His Thr Leu Leu Val Trp
    450                 455                 460

Ala Pro Ser Asn Tyr Gln Val Val Lys Asp Gly Leu Asn Gln Lys Pro
465                 470                 475                 480

Glu Lys Gly Arg Asn Gly Ile Arg Phe Val Asn Ala Phe Gly Glu Ser
                485                 490                 495

Phe Gly Val Thr Met Asp Gly Glu Val Tyr Asn Asn Val Ser Gly His
            500                 505                 510

Asn Ala Ser Glu Tyr Leu Phe Phe Ser Ser Gly Val Lys Ser Phe Thr
        515                 520                 525

Ile Asn Ser Pro Glu Ile Ser Gln Gln Cys Glu Lys Gln Phe Lys Thr
    530                 535                 540

Ser Tyr Leu Glu Phe Gly Ser Ala Phe Thr Tyr Val Ile Ser Arg Lys
545                 550                 555                 560

Ser Asp Gly Cys Pro Glu Pro Lys Ile Phe Glu Asp Ile Ser Pro Asn
                565                 570                 575

Thr Val Ser Met Ala Leu Gln Ile Pro Gln Tyr Phe Leu Leu Thr Cys
            580                 585                 590

Gly Glu Val Val Phe Ser Ile Thr Gly Leu Glu Phe Ser Tyr Ser Gln
        595                 600                 605

Ala Pro Ser Asn Met Lys Ser Val Leu Gln Ala Gly Trp Leu Leu Thr
    610                 615                 620

Val Ala Val Gly Asn Ile Ile Val Leu Ile Val Ala Gly Ala Gly Gln
625                 630                 635                 640

Phe Ser Glu Gln Trp Ala Glu Tyr Val Leu Phe Ala Ala Leu Leu Leu
                645                 650                 655

Val Val Cys Ile Ile Phe Ala Ile Met Ala Arg Phe Tyr Thr Tyr Val
            660                 665                 670

Asn Pro Ala Glu Ile Glu Ala Gln Phe Asp Glu Asp Asp Lys Glu Asp
        675                 680                 685

Asp Leu Glu Lys Ser Asn Pro Tyr Ala Lys Leu Asp Phe Val Ser Gln
    690                 695                 700

Thr Gln Met
705


<210> SEQ ID NO 18
<211> LENGTH: 707
<212> TYPE: PRT
<213> ORGANISM: Oryctolagus cuniculus

<400> SEQUENCE: 18

Met Gly Met Ser Lys Ser Leu Ser Cys Phe Gly Tyr Pro Leu Ser Ile
 1               5                  10                  15

Phe Phe Ile Val Val Asn Glu Phe Cys Glu Arg Phe Ser Tyr Tyr Gly
            20                  25                  30

Met Arg Ala Leu Leu Ile Leu Tyr Phe Arg Asn Phe Ile Gly Trp Asp
        35                  40                  45

Asp Asn Leu Ser Thr Val Ile Tyr His Thr Phe Val Ala Leu Cys Tyr
    50                  55                  60
```

-continued

```
Leu Thr Pro Ile Leu Gly Ala Leu Ile Ala Asp Ala Trp Leu Gly Lys
65                  70                  75                  80

Phe Lys Thr Ile Val Trp Leu Ser Ile Val Tyr Thr Ile Gly Gln Ala
                85                  90                  95

Val Thr Ser Leu Ser Ser Val Asn Glu Leu Thr Asp Asn Asn His Asp
            100                 105                 110

Gly Thr Pro Asp Ser Leu Pro Val His Val Ala Val Cys Met Ile Gly
        115                 120                 125

Leu Leu Leu Ile Ala Leu Gly Thr Gly Gly Ile Lys Pro Cys Val Ser
    130                 135                 140

Ala Phe Gly Gly Asp Gln Phe Glu Glu Gly Gln Glu Lys Gln Arg Asn
145                 150                 155                 160

Arg Phe Phe Ser Ile Phe Tyr Leu Ala Ile Asn Ala Gly Ser Leu Leu
                165                 170                 175

Ser Thr Ile Ile Thr Pro Met Val Arg Val Gln Gln Cys Gly Ile His
            180                 185                 190

Val Lys Gln Ala Cys Tyr Pro Leu Ala Phe Gly Ile Pro Ala Ile Leu
        195                 200                 205

Met Ala Val Ser Leu Ile Val Phe Ile Ile Gly Ser Gly Met Tyr Lys
    210                 215                 220

Lys Phe Lys Pro Gln Gly Asn Ile Leu Ser Lys Val Val Lys Cys Ile
225                 230                 235                 240

Cys Phe Ala Ile Lys Asn Arg Phe Arg His Arg Ser Lys Gln Phe Pro
                245                 250                 255

Lys Arg Ala His Trp Leu Asp Trp Ala Lys Glu Lys Tyr Asp Glu Arg
            260                 265                 270

Leu Ile Ala Gln Ile Lys Met Val Thr Arg Val Leu Phe Leu Tyr Ile
        275                 280                 285

Pro Leu Pro Met Phe Trp Ala Leu Phe Asp Gln Gln Gly Ser Arg Trp
    290                 295                 300

Thr Leu Gln Ala Thr Thr Met Ser Gly Arg Ile Gly Ile Leu Glu Ile
305                 310                 315                 320

Gln Pro Asp Gln Met Gln Thr Val Asn Thr Ile Leu Ile Ile Ile Leu
                325                 330                 335

Val Pro Ile Met Asp Ala Val Val Tyr Pro Leu Ile Ala Lys Cys Gly
            340                 345                 350

Leu Asn Phe Thr Ser Leu Lys Lys Met Thr Ile Gly Met Phe Leu Ala
        355                 360                 365

Ser Met Ala Phe Val Ala Ala Ala Ile Leu Gln Val Glu Ile Asp Lys
    370                 375                 380

Thr Leu Pro Val Phe Pro Lys Ala Asn Glu Val Gln Ile Lys Val Leu
385                 390                 395                 400

Asn Val Gly Ser Glu Asn Met Ile Ile Ser Leu Pro Gly Gln Thr Val
                405                 410                 415

Thr Leu Asn Gln Met Ser Gln Thr Asn Glu Phe Met Thr Phe Asn Glu
            420                 425                 430

Asp Thr Leu Thr Ser Ile Asn Ile Thr Ser Gly Ser Gln Val Thr Met
        435                 440                 445

Ile Thr Pro Ser Leu Glu Ala Gly Gln Arg His Thr Leu Leu Val Trp
    450                 455                 460

Ala Pro Asn Asn Tyr Arg Val Val Asn Asp Gly Leu Thr Gln Lys Ser
465                 470                 475                 480
```

-continued

```
Asp Lys Gly Glu Asn Gly Ile Arg Phe Val Asn Thr Tyr Ser Gln Pro
                485                 490                 495

Ile Asn Val Thr Met Ser Gly Lys Val Tyr Glu His Ile Ala Ser Tyr
            500                 505                 510

Asn Ala Ser Glu Tyr Gln Phe Phe Thr Ser Gly Val Lys Gly Phe Thr
        515                 520                 525

Val Ser Ser Ala Gly Ile Ser Glu Gln Cys Arg Arg Asp Phe Glu Ser
    530                 535                 540

Pro Tyr Leu Glu Phe Gly Ser Ala Tyr Thr Tyr Leu Ile Thr Ser Gln
545                 550                 555                 560

Ala Thr Gly Cys Pro Gln Val Thr Glu Phe Glu Asp Ile Pro Pro Asn
                565                 570                 575

Thr Met Asn Met Ala Trp Gln Ile Pro Gln Tyr Phe Leu Ile Thr Ser
            580                 585                 590

Gly Glu Val Val Phe Ser Ile Thr Gly Leu Glu Phe Ser Tyr Ser Gln
        595                 600                 605

Ala Pro Ser Asn Met Lys Ser Val Leu Gln Asp Arg Trp Leu Leu Thr
    610                 615                 620

Val Ala Val Gly Asn Ile Ile Val Leu Ile Val Ala Gly Ala Gly Gln
625                 630                 635                 640

Ile Asn Lys Gln Trp Ala Glu Tyr Ile Leu Phe Ala Ala Leu Leu Leu
                645                 650                 655

Val Val Cys Val Ile Phe Ala Ile Met Ala Arg Phe Tyr Thr Tyr Val
            660                 665                 670

Asn Pro Ala Glu Ile Glu Ala Gln Phe Glu Glu Asp Glu Lys Lys Lys
        675                 680                 685

Asn Pro Glu Lys Asn Asp Leu Tyr Pro Ser Val Ala Pro Val Ser Gln
    690                 695                 700

Thr Gln Met
705


<210> SEQ ID NO 19
<211> LENGTH: 714
<212> TYPE: PRT
<213> ORGANISM: Gallus gallus

<400> SEQUENCE: 19

Met Ala Ala Lys Ser Lys Ser Lys Gly Arg Ser Val Pro Asn Cys Phe
 1               5                  10                  15

Gly Tyr Pro Leu Ser Ile Phe Phe Ile Val Ile Asn Glu Phe Cys Glu
            20                  25                  30

Arg Phe Ser Tyr Tyr Gly Met Arg Ala Val Leu Val Leu Tyr Phe Lys
        35                  40                  45

Tyr Phe Leu Arg Trp Asp Asp Asn Phe Ser Thr Ala Ile Tyr His Thr
    50                  55                  60

Phe Val Ala Leu Cys Tyr Leu Thr Pro Ile Leu Gly Ala Leu Ile Ala
65                  70                  75                  80

Asp Ser Trp Leu Gly Lys Phe Lys Thr Ile Val Ser Leu Ser Ile Val
                85                  90                  95

Tyr Thr Ile Gly Gln Ala Val Met Ala Val Ser Ser Ile Asn Asp Met
            100                 105                 110

Thr Asp Gln Asn Arg Asp Gly Asn Pro Asp Asn Ile Ala Val His Ile
        115                 120                 125

Ala Leu Ser Met Thr Gly Leu Ile Leu Ile Ala Leu Gly Thr Gly Gly
    130                 135                 140
```

-continued

```
Ile Lys Pro Cys Val Ser Ala Phe Gly Gly Asp Gln Phe Glu Glu His
145                 150                 155                 160

Gln Glu Lys Gln Arg Ser Arg Phe Phe Ser Ile Phe Tyr Leu Ser Ile
                165                 170                 175

Asn Ala Gly Ser Leu Ile Ser Thr Ile Ile Thr Pro Ile Leu Arg Ala
            180                 185                 190

Gln Glu Cys Gly Ile His Ser Arg Gln Gln Cys Tyr Pro Leu Ala Phe
        195                 200                 205

Gly Val Pro Ala Ala Leu Met Ala Val Ser Leu Val Val Phe Ile Ala
    210                 215                 220

Gly Ser Gly Met Tyr Lys Lys Val Gln Pro Gln Gly Asn Ile Met Val
225                 230                 235                 240

Arg Val Cys Lys Cys Ile Gly Phe Ala Ile Lys Asn Arg Phe Arg His
                245                 250                 255

Arg Ser Lys Glu Tyr Pro Lys Arg Glu His Trp Leu Asp Trp Ala Ser
            260                 265                 270

Glu Lys Tyr Asp Lys Arg Leu Ile Ala Gln Thr Lys Met Val Leu Lys
        275                 280                 285

Val Leu Phe Leu Tyr Ile Pro Leu Pro Met Phe Trp Ala Leu Phe Asp
    290                 295                 300

Gln Gln Gly Ser Arg Trp Thr Leu Gln Ala Thr Thr Met Asp Gly Asp
305                 310                 315                 320

Phe Gly Ala Met Gln Ile Gln Pro Asp Gln Met Gln Thr Val Asn Pro
                325                 330                 335

Ile Leu Ile Ile Ile Met Val Pro Val Val Asp Ala Val Ile Tyr Pro
            340                 345                 350

Leu Ile Gln Lys Cys Lys Ile Asn Phe Thr Pro Leu Arg Arg Ile Thr
        355                 360                 365

Val Gly Met Phe Leu Ala Gly Leu Ala Phe Val Ala Ala Ala Leu Leu
    370                 375                 380

Gln Val Gln Ile Asp Lys Thr Leu Pro Val Phe Pro Ala Ala Gly Gln
385                 390                 395                 400

Ala Gln Ile Lys Ile Ile Asn Leu Gly Asp Ser Asn Ala Asn Val Thr
                405                 410                 415

Phe Leu Pro Asn Leu Gln Asn Val Thr Val Leu Pro Met Glu Ser Thr
            420                 425                 430

Gly Tyr Arg Met Phe Glu Ser Ser Gln Leu Lys Ser Val Met Val Asn
        435                 440                 445

Phe Gly Ser Glu Ser Arg Ser Glu Asn Ile Asp Ser Ile Ser Ser Asn
    450                 455                 460

Thr His Thr Val Thr Ile Lys Asn Ala Ala Ala Gly Ile Val Ser Ser
465                 470                 475                 480

Leu Arg Ser Asp Asn Phe Thr Ser Lys Pro Glu Glu Gly Lys Asn Leu
                485                 490                 495

Val Arg Phe Val Asn Asn Leu Pro Gln Thr Val Asn Ile Thr Met Gly
            500                 505                 510

Asp Thr Thr Phe Gly Ile Leu Glu Glu Thr Ser Ile Ser Asn Tyr Ser
        515                 520                 525

Pro Phe Ser Gly Gly Arg Thr Tyr Asp Ile Val Ile Thr Ala Gly Ser
    530                 535                 540

Thr Asn Cys Lys Pro Thr Ser Glu Lys Leu Gly Tyr Gly Gly Ala Tyr
545                 550                 555                 560
```

-continued

```
Thr Ile Val Ile Asn Glu Cys Ser Gly Asp Val Thr Gln Leu Arg Tyr
                565                 570                 575

Ile Glu Asp Ile Gln Pro Asn Thr Val His Met Ala Trp Gln Ile Pro
            580                 585                 590

Gln Tyr Phe Ile Leu Thr Cys Gly Glu Val Val Phe Ser Val Thr Gly
        595                 600                 605

Leu Glu Phe Ser Tyr Ser Gln Ala Pro Ser Asn Met Lys Ser Val Leu
    610                 615                 620

Gln Ala Gly Trp Leu Leu Thr Val Ala Val Gly Asn Ile Ile Val Leu
625                 630                 635                 640

Ile Val Ala Gly Ala Ser Lys Leu Ser Glu Gln Trp Ala Glu Tyr Val
                645                 650                 655

Leu Phe Ala Ala Leu Leu Phe Ala Val Cys Ile Ile Phe Ala Val Met
            660                 665                 670

Ala Tyr Phe Tyr Thr Tyr Thr Asp Pro Asn Glu Val Glu Ala Gln Leu
        675                 680                 685

Asp Glu Glu Glu Lys Lys Lys Gln Ile Lys Gln Asp Pro Asp Leu His
    690                 695                 700

Gly Lys Glu Ser Glu Ala Val Ser Gln Met
705                 710


<210> SEQ ID NO 20
<211> LENGTH: 2124
<212> TYPE: DNA
<213> ORGANISM: Canis familiaris

<400> SEQUENCE: 20

atgggcatgt ccaagtcata tggttgcttt ggttacccct tgagcatctt cttcatcgtg     60

gtcaatgagt tctgtgaaag attttcctac tatggaatga gagcactcct gattctgtac    120

ttcagacggt tcatcgggtg ggacgataat ctgtccacgg ccatctacca cacgtttgtg    180

gctctgtgct acctgacgcc gatcctcggc gcactgatcg cagactcctg gctgggaaag    240

ttcaagacaa tcgtgtcact ctccattgtc tacacaattg gacaggcggt cactgcagta    300

agctcaatta atgacctcac agactataac aaagatggaa ctcctgacaa tctgtccgtg    360

catgtggcac tgtccatgat tggcctggcc ctgatagctc tgggaactgg aggaataaag    420

ccctgtgtgt ctgcatttgg tggagaccag tttgaagagg gccaggaaaa acaaagaaac    480

agattctttt ccatctttta tttggccatt aatgctggaa gcttgatttc cactattgtc    540

actcccatgc tcagagttca cgaatgtgga atttacagtc agaaagcttg ttacccactg    600

gcatttgggg ttcctgctgc tctcatggcc gtatctctga ttgtatttgt cattggcagt    660

ggaatgtaca agaagtttca gccccagggt aatgtcatgg gtaaagttgt caagtgcatt    720

ggttttgccc tcaaaaatag gtttaggcac cggagtaagc agtttcccaa gagggagcac    780

tggctggact gggctaaaga gaaatacgat gagcggctca tctctcaaat taagatggtc    840

acaaaagtga tgttcttgta catcccactc ccaatgttct gggccctgtt tgaccagcag    900

ggctccaggt ggacactgca agcaacagct atgagtggga aaattggact tcttgaagtt    960

cagccagatc agatgcagac tgtgaatgcc atcttgattg tcgtcatggt ccccatcatg   1020

gatgccgtgg tgtaccctct gattgcaaaa tgtggcttca atttcacctc cttgaagagg   1080

atgacagttg gaatgttcct ggcttccatg gccttcgtga tggcggcgat tgttcagctg   1140

gaaattgata aaactcttcc agtcttcccc aaacaaaatg aagtccaaat caaagtactg   1200

aatataggaa atggtgccat gaatgtatct tttcctggag cggtggtgac agttagccaa   1260
```

-continued

```
atgagtcaat cagatggatt tatgactttt gatgtagaca aactgacaag tataaacatt   1320

tcttccactg gatcaccagt cattccagtg acttataact ttgagcaggg ccatcgccat   1380

acccttctag tatgggcccc caataattac cgagtggtaa aggatggcct taaccagaag   1440

ccagaaaaag gagaaaatgg aatcagattt ataaatagtc ttaatgagag cctcaacatc   1500

accatgggcg acaaagttta tgtgaatgtc accagtcaca atgccagcga gtatcagttc   1560

ttttctttgg gcacaaaaaa cattacaata agttcaacac aacagatctc acaaaattgt   1620

acaaaagttc tccaatcatc caaccttgaa tttggtagtg catataccta tgtaatcgga   1680

acgcagagca ctggctgccc tgaattgcat atgtttgaag atatttcacc caacacagtt   1740

aacatggctc tgcagatccc gcagtacttc ctcatcacct gcggcgaggt ggttttctct   1800

gtcacaggac tggagttctc atattctcag gccccctcca acatgaagtc ggtgcttcag   1860

gcgggatggc tgctgacagt ggctgttggc aacatcattg tgctcattgt ggcaggagca   1920

ggccagttca gtgaacagtg ggctgaatac atcctatttg cggcattgct tctggttgtc   1980

tgtgtaatat ttgccatcat ggcccggttt tacacttacg tcaatccagc agagattgaa   2040

gctcagtttg acgacgatga gaaaaagaac ctggaaaaga tgaatgtata ttccacggta   2100

actccggtct cacagacaca gatg                                          2124
```

<210> SEQ ID NO 21
<211> LENGTH: 708
<212> TYPE: PRT
<213> ORGANISM: Canis familiaris

<400> SEQUENCE: 21

```
Met Gly Met Ser Lys Ser Tyr Gly Cys Phe Gly Tyr Pro Leu Ser Ile
 1               5                  10                  15

Phe Phe Ile Val Val Asn Glu Phe Cys Glu Arg Phe Ser Tyr Tyr Gly
            20                  25                  30

Met Arg Ala Leu Leu Ile Leu Tyr Phe Arg Arg Phe Ile Gly Trp Asp
        35                  40                  45

Asp Asn Leu Ser Thr Ala Ile Tyr His Thr Phe Val Ala Leu Cys Tyr
    50                  55                  60

Leu Thr Pro Ile Leu Gly Ala Leu Ile Ala Asp Ser Trp Leu Gly Lys
65                  70                  75                  80

Phe Lys Thr Ile Val Ser Leu Ser Ile Val Tyr Thr Ile Gly Gln Ala
                85                  90                  95

Val Thr Ala Val Ser Ser Ile Asn Asp Leu Thr Asp Tyr Asn Lys Asp
            100                 105                 110

Gly Thr Pro Asp Asn Leu Ser Val His Val Ala Leu Ser Met Ile Gly
        115                 120                 125

Leu Ala Leu Ile Ala Leu Gly Thr Gly Gly Ile Lys Pro Cys Val Ser
    130                 135                 140

Ala Phe Gly Gly Asp Gln Phe Glu Glu Gly Gln Glu Lys Gln Arg Asn
145                 150                 155                 160

Arg Phe Phe Ser Ile Phe Tyr Leu Ala Ile Asn Ala Gly Ser Leu Ile
                165                 170                 175

Ser Thr Ile Val Thr Pro Met Leu Arg Val His Glu Cys Gly Ile Tyr
            180                 185                 190

Ser Gln Lys Ala Cys Tyr Pro Leu Ala Phe Gly Val Pro Ala Ala Leu
        195                 200                 205

Met Ala Val Ser Leu Ile Val Phe Val Ile Gly Ser Gly Met Tyr Lys
```

-continued

```
    210                 215                 220

Lys Phe Gln Pro Gln Gly Asn Val Met Gly Lys Val Val Lys Cys Ile
225                 230                 235                 240

Gly Phe Ala Leu Lys Asn Arg Phe Arg His Arg Ser Lys Gln Phe Pro
                245                 250                 255

Lys Arg Glu His Trp Leu Asp Trp Ala Lys Glu Lys Tyr Asp Glu Arg
            260                 265                 270

Leu Ile Ser Gln Ile Lys Met Val Thr Lys Val Met Phe Leu Tyr Ile
        275                 280                 285

Pro Leu Pro Met Phe Trp Ala Leu Phe Asp Gln Gln Gly Ser Arg Trp
    290                 295                 300

Thr Leu Gln Ala Thr Ala Met Ser Gly Lys Ile Gly Leu Leu Glu Val
305                 310                 315                 320

Gln Pro Asp Gln Met Gln Thr Val Asn Ala Ile Leu Ile Val Val Met
                325                 330                 335

Val Pro Ile Met Asp Ala Val Val Tyr Pro Leu Ile Ala Lys Cys Gly
            340                 345                 350

Phe Asn Phe Thr Ser Leu Lys Arg Met Thr Val Gly Met Phe Leu Ala
        355                 360                 365

Ser Met Ala Phe Val Met Ala Ala Ile Val Gln Leu Glu Ile Asp Lys
    370                 375                 380

Thr Leu Pro Val Phe Pro Lys Gln Asn Glu Val Gln Ile Lys Val Leu
385                 390                 395                 400

Asn Ile Gly Asn Gly Ala Met Asn Val Ser Phe Pro Gly Ala Val Val
                405                 410                 415

Thr Val Ser Gln Met Ser Gln Ser Asp Gly Phe Met Thr Phe Asp Val
            420                 425                 430

Asp Lys Leu Thr Ser Ile Asn Ile Ser Ser Thr Gly Ser Pro Val Ile
        435                 440                 445

Pro Val Thr Tyr Asn Phe Glu Gln Gly His Arg His Thr Leu Leu Val
    450                 455                 460

Trp Ala Pro Asn Asn Tyr Arg Val Val Lys Asp Gly Leu Asn Gln Lys
465                 470                 475                 480

Pro Glu Lys Gly Glu Asn Gly Ile Arg Phe Ile Asn Ser Leu Asn Glu
                485                 490                 495

Ser Leu Asn Ile Thr Met Gly Asp Lys Val Tyr Val Asn Val Thr Ser
            500                 505                 510

His Asn Ala Ser Glu Tyr Gln Phe Phe Ser Leu Gly Thr Lys Asn Ile
        515                 520                 525

Thr Ile Ser Ser Thr Gln Gln Ile Ser Gln Asn Cys Thr Lys Val Leu
    530                 535                 540

Gln Ser Ser Asn Leu Glu Phe Gly Ser Ala Tyr Thr Tyr Val Ile Gly
545                 550                 555                 560

Thr Gln Ser Thr Gly Cys Pro Glu Leu His Met Phe Glu Asp Ile Ser
                565                 570                 575

Pro Asn Thr Val Asn Met Ala Leu Gln Ile Pro Gln Tyr Phe Leu Ile
            580                 585                 590

Thr Cys Gly Glu Val Val Phe Ser Val Thr Gly Leu Glu Phe Ser Tyr
        595                 600                 605

Ser Gln Ala Pro Ser Asn Met Lys Ser Val Leu Gln Ala Gly Trp Leu
    610                 615                 620

Leu Thr Val Ala Val Gly Asn Ile Ile Val Leu Ile Val Ala Gly Ala
625                 630                 635                 640
```

-continued

```
Gly Gln Phe Ser Glu Gln Trp Ala Glu Tyr Ile Leu Phe Ala Ala Leu
                645                 650                 655

Leu Leu Val Val Cys Val Ile Phe Ala Ile Met Ala Arg Phe Tyr Thr
            660                 665                 670

Tyr Val Asn Pro Ala Glu Ile Glu Ala Gln Phe Asp Asp Asp Glu Lys
        675                 680                 685

Lys Asn Leu Glu Lys Met Asn Val Tyr Ser Thr Val Thr Pro Val Ser
    690                 695                 700

Gln Thr Gln Met
705
```